United States Patent
Khan et al.

(10) Patent No.: US 12,134,790 B2
(45) Date of Patent: Nov. 5, 2024

(54) METHODS OF IMPROVING CARDIOVASCULAR FUNCTION AND TREATING CARDIOVASCULAR DISEASE USING A RECOMBINANT ECTONUCLEOTIDE PYROPHOSPHATASE PHOSPHODIESTERASE (NPP1)

(71) Applicant: Inozyme Pharma, Inc., Boston, MA (US)

(72) Inventors: Tayeba Khan, Lexington, MA (US); Andre Marozsan, Killingworth, CT (US); Kim Askew, Lincoln, MA (US)

(73) Assignee: Inozyme Pharma, Inc., Boston, MA (US)

( * ) Notice: Subject to any disclaimer, the term of this patent is extended or adjusted under 35 U.S.C. 154(b) by 245 days.

(21) Appl. No.: 16/648,388

(22) PCT Filed: Sep. 26, 2018

(86) PCT No.: PCT/US2018/052795
§ 371 (c)(1),
(2) Date: Mar. 18, 2020

(87) PCT Pub. No.: WO2019/067502
PCT Pub. Date: Apr. 4, 2019

(65) Prior Publication Data
US 2020/0263153 A1    Aug. 20, 2020

Related U.S. Application Data

(60) Provisional application No. 62/563,829, filed on Sep. 27, 2017.

(51) Int. Cl.
*C12N 9/16* (2006.01)
*A61K 9/00* (2006.01)
*A61K 45/06* (2006.01)
*A61P 9/10* (2006.01)
*C07K 19/00* (2006.01)

(52) U.S. Cl.
CPC ............... *C12N 9/16* (2013.01); *A61P 9/10* (2018.01); *C07K 19/00* (2013.01); *A61K 9/0019* (2013.01); *A61K 45/06* (2013.01); *C12Y 301/04001* (2013.01)

(58) Field of Classification Search
CPC ............ C12N 9/16; A61P 9/10; C07K 19/00; A61K 9/0019; A61K 45/06; A61K 38/46; C12Y 301/04001
See application file for complete search history.

(56) References Cited

U.S. PATENT DOCUMENTS

| | | |
|---|---|---|
| 4,751,180 A | 6/1988 | Cousens et al. |
| 4,935,233 A | 6/1990 | Bell et al. |
| 5,418,618 A | 5/1995 | Kagawa et al. |
| 5,428,130 A | 6/1995 | Capon et al. |
| 5,804,413 A | 9/1998 | DeLuca |
| 5,808,656 A | 9/1998 | Goldmann |
| 5,837,532 A | 11/1998 | Preston et al. |
| 5,846,782 A | 12/1998 | Wickham et al. |
| 5,968,508 A | 10/1999 | Goldfine et al. |
| 6,001,650 A | 12/1999 | Colosi |
| 6,043,056 A | 3/2000 | Yue et al. |
| 6,156,303 A | 12/2000 | Russell et al. |
| 6,358,923 B1 | 3/2002 | Yue et al. |
| 6,455,495 B1 | 9/2002 | Orgel et al. |
| 6,498,617 B1 | 12/2002 | Ishida et al. |
| 6,596,535 B1 | 7/2003 | Carter |
| 6,730,822 B1 | 5/2004 | Ivarie et al. |
| 6,825,396 B2 | 11/2004 | MacArthur |
| 6,875,588 B2 | 4/2005 | Harvey et al. |
| 7,125,717 B2 | 10/2006 | Carter |
| 7,294,507 B2 | 11/2007 | Harvey et al. |
| 7,312,374 B2 | 12/2007 | Rapp et al. |
| 7,318,919 B2 | 1/2008 | Gregory et al. |
| 7,323,542 B2 | 1/2008 | Balian |
| 7,456,683 B2 | 11/2008 | Takano et al. |
| 7,507,873 B2 | 3/2009 | Harvey et al. |
| 7,521,591 B2 | 4/2009 | Ivarie et al. |
| 7,531,167 B2 | 5/2009 | Glorioso et al. |
| 7,534,929 B2 | 5/2009 | Ivarie et al. |
| 7,858,297 B2 | 12/2010 | Girard et al. |
| 7,888,372 B2 | 2/2011 | Millan et al. |
| 7,902,151 B2 | 3/2011 | Gorczynski et al. |
| 7,960,529 B2 | 6/2011 | Crine et al. |

(Continued)

FOREIGN PATENT DOCUMENTS

| | | |
|---|---|---|
| DE | 20121960 U1 | 1/2004 |
| EP | 2368999 B1 | 3/2014 |

(Continued)

OTHER PUBLICATIONS

Parati et al. 2016; Hypertension in chronic kidney disease Part 1. Hypertension. 67(6): 1093-1101.*
DiLullo et al. 2015; Left ventricular hypertrophy in chronic kidney disease patients: From pathophysiology to treatment. CardioRenal Medicine. 5: 254-266.*
Kashioulis et al. 2018; Adenine-diced chronic renal failure in rates: A model of chronic renocardiac syndrome with left ventricular diastolic dysfunction by preserved ejection fraction. Kidney & Blood Pressure Research. 43: 1053-1064.*
Belli, S.I. et al., "Identification and characterization of a soluble form of the plasma cell membrane glycoprotein PC-1 (5'-nucleotide phosphodiesterase)" Eur J Biochem, 217:421-428 (1993).
Goding, J.W. et al., "Physiological and pathophysiological functions of the ecto-nucleotide pyrophosphatase/phosphodiesterase family" Biochimica et Biophysica Acta, 1638(1):1-19 (May 20, 2003).

(Continued)

*Primary Examiner* — Iqbal H Chowdhury
(74) *Attorney, Agent, or Firm* — Nutter McClennen & Fish LLP

(57) ABSTRACT

The present invention provides methods for improving cardiovascular function in a human patient (e.g., reducing hypertension), as well as methods of treating a cardiovascular disease, by administering a recombinant human soluble ectonucleotide pyrophosphatase phosphodiesterase (hsNPP1), active fragment or fusion protein thereof.

25 Claims, 7 Drawing Sheets
Specification includes a Sequence Listing.

(56) References Cited

U.S. PATENT DOCUMENTS

| | | | |
|---|---|---|---|
| 8,017,324 | B1 | 9/2011 | Froguel et al. |
| 8,519,214 | B2 | 8/2013 | Ivarie et al. |
| 8,846,603 | B2 | 9/2014 | Quinn et al. |
| 9,540,621 | B2 | 1/2017 | Quinn et al. |
| 9,642,869 | B2 | 5/2017 | Reddy et al. |
| 9,642,896 | B1 | 5/2017 | Braddock et al. |
| 9,744,219 | B2 | 8/2017 | Braddock et al. |
| 9,867,870 | B2 | 1/2018 | Braddock et al. |
| 9,913,881 | B2 | 3/2018 | Braddock et al. |
| 10,011,847 | B2 | 7/2018 | Aranda et al. |
| 10,052,367 | B2 | 8/2018 | Braddock et al. |
| 10,064,917 | B2 | 9/2018 | Braddock et al. |
| 10,213,483 | B2 | 2/2019 | Otterlei et al. |
| 10,213,484 | B2 | 2/2019 | Braddock et al. |
| 10,357,541 | B2 | 7/2019 | Braddock et al. |
| 10,493,135 | B2 * | 12/2019 | Quinn .................... A61K 38/46 |
| 10,517,927 | B2 | 12/2019 | Braddock et al. |
| 10,583,170 | B2 | 3/2020 | Braddock et al. |
| 10,624,958 | B2 | 4/2020 | Braddock et al. |
| 10,960,050 | B2 | 3/2021 | Braddock et al. |
| 11,266,722 | B2 | 3/2022 | Braddock et al. |
| 11,364,284 | B2 | 6/2022 | Yan et al. |
| 2001/0020086 | A1 | 9/2001 | Hubbell et al. |
| 2001/0051065 | A1 | 12/2001 | Togami |
| 2002/0108132 | A1 | 8/2002 | Rapp |
| 2003/0190311 | A1 | 10/2003 | Dall'Acqua et al. |
| 2004/0166521 | A1 | 8/2004 | Boyd et al. |
| 2004/0224893 | A1 | 11/2004 | Wang et al. |
| 2006/0074255 | A1 | 4/2006 | Takayama et al. |
| 2007/0004913 | A1 | 1/2007 | Challita-Eid et al. |
| 2007/0015145 | A1 | 1/2007 | Woolf et al. |
| 2008/0273206 | A1 | 11/2008 | Genge et al. |
| 2009/0180989 | A1 | 7/2009 | Harvey |
| 2009/0253176 | A1 | 10/2009 | Parker et al. |
| 2009/0296167 | A1 | 12/2009 | Motoyama |
| 2009/0298167 | A1 | 12/2009 | Bloom et al. |
| 2010/0184672 | A1 | 7/2010 | McCarty et al. |
| 2010/0203076 | A1 | 8/2010 | Fotin-Mleczek et al. |
| 2010/0240583 | A1 | 9/2010 | Tada et al. |
| 2012/0009592 | A1 | 1/2012 | Froguel et al. |
| 2013/0012574 | A1 | 1/2013 | Monahan et al. |
| 2014/0154774 | A1 | 6/2014 | Quinn et al. |
| 2014/0349369 | A1 | 11/2014 | Buechler et al. |
| 2014/0377859 | A1 | 12/2014 | Quinn et al. |
| 2015/0024460 | A1 | 1/2015 | Quinn et al. |
| 2015/0359858 | A1 | 12/2015 | Braddock et al. |
| 2016/0184387 | A1 | 6/2016 | Charmot et al. |
| 2016/0184458 | A1 | 6/2016 | Heartlein |
| 2017/0096684 | A1 | 4/2017 | Alton et al. |
| 2017/0145393 | A1 | 5/2017 | Quinn et al. |
| 2017/0204386 | A1 | 7/2017 | Vitalis et al. |
| 2017/0290926 | A1 | 10/2017 | Smith et al. |
| 2017/0340713 | A1 | 11/2017 | Braddock et al. |
| 2018/0042738 | A1 | 2/2018 | Sun et al. |
| 2018/0057821 | A1 | 3/2018 | Braddock et al. |
| 2018/0318400 | A1 | 11/2018 | Quinn et al. |
| 2018/0340187 | A1 | 11/2018 | Rodino-Klapac |
| 2018/0371434 | A1 | 12/2018 | Braddock et al. |
| 2019/0022286 | A1 | 1/2019 | Schneiderman |
| 2020/0138905 | A1 | 5/2020 | Braddock et al. |
| 2020/0306349 | A1 | 10/2020 | Yan et al. |

FOREIGN PATENT DOCUMENTS

| | | | |
|---|---|---|---|
| EP | 3298140 | A1 | 3/2018 |
| JP | H04292169 | A | 10/1992 |
| JP | 2008188015 | A | 8/2008 |
| JP | 2014-509851 | A | 4/2014 |
| JP | 2014509617 | A | 4/2014 |
| JP | 2016530899 | A | 10/2016 |
| JP | 6894664 | B2 | 6/2021 |
| RU | 2272841 | C2 | 3/2006 |
| RU | 2013142583 | A | 4/2015 |
| RU | 2016107788 | A | 11/2018 |
| WO | 91/02788 | A1 | 3/1991 |
| WO | 96/04394 | A1 | 2/1996 |
| WO | 98/15637 | A1 | 4/1998 |
| WO | 99/06583 | A1 | 2/1999 |
| WO | 1999/019495 | A1 | 4/1999 |
| WO | 2000/032217 | A1 | 6/2000 |
| WO | 0239994 | A2 | 5/2002 |
| WO | 2002092020 | A2 | 11/2002 |
| WO | 03/040340 | A2 | 5/2003 |
| WO | WO2006039480 | A2 | 4/2006 |
| WO | 2006059113 | A2 | 6/2006 |
| WO | 2006/135925 | A2 | 12/2006 |
| WO | 2006135935 | A1 | 12/2006 |
| WO | 2008/065225 | A2 | 6/2008 |
| WO | 2008/105911 | A2 | 9/2008 |
| WO | 2011113027 | A2 | 9/2011 |
| WO | 2012/125182 | A1 | 9/2012 |
| WO | WO2014126965 | A2 | 8/2014 |
| WO | 2016100803 | A2 | 6/2016 |
| WO | 2016/187408 | A1 | 11/2016 |
| WO | 2017/087936 | A1 | 5/2017 |
| WO | 2017/191274 | A2 | 11/2017 |
| WO | 2017/218786 | A1 | 12/2017 |
| WO | 2018/027024 | A1 | 2/2018 |
| WO | 2018/157165 | A1 | 8/2018 |
| WO | 2019067502 | A1 | 4/2019 |
| WO | 2019217373 | A1 | 11/2019 |

OTHER PUBLICATIONS

International Preliminary Report on Patentabililty, PCT/US2017/037695, dated Sep. 4, 2018, 8 pages.

International Search Report and Written Opinion, PCT/US2017/037695, dated Sep. 8, 2017, 11 pages.

Jansen, S., et al., "Structure of NPP1, an Ectonucleotide Pyrophosphatase/Phosphodiesterase Involved in Tissue Calcification" Structure, 20(11):1948-1959 (Nov. 7, 2012).

Johnson, K, et al., "Linked Deficiencies in Extracellular PPi and Osteopontin Mediate Pathologic Calcification Associated With Defective PC-1 and ANK Expression" Journal of Bone and Mineral Research, 18(6):994-1004 (Jun. 1, 2003).

Mackenzie, N.C.W. et al., "New insights into NPP1 function: Lessons from clinical and animal studies" Bone, 51:961-968 (2012).

Nitschke, Y. et al., "Nppl promotes atherosclerosis in ApoE knockout mice" Journal of Cellular and Molecular Medicine, 15(11):2273-2283 (2011).

Rezg, R. et al., "Inhibitors of Vascular Calcification as Potential Therapeutic Targets" J Nephrol, 24(4):416-427 (2011).

Rutsch, F. et al., "Hypophosphatemia, Hyperphosphaturia, and Bisphosphonate Treatment Are Associated With Survival Beyond Infancy in Generalized Arterial Calcification of Infancy" Circ Cardiovasc Genet, 1(2):133-140 (Dec. 1, 2008).

Rutsch, F. et al. "Genetics in Arterial Calcification. Pieces of a Puzzle and Cogs in a Wheel" Circulation Research, 109:578-592 (2011).

Serrano, R. et al., "Mono-allelic and bi-allelic ENPPI deficiency promote post-injury neointimal hyperplasia associated with increased C/EBP homologous protein expression" Atherosclerosis, 233(2):493-502 (2014).

Stefan, C. et al., "NPP-type ectophosphodiesterases: unity in diversity" Trends in Biochemical Sciences, 30(10):542-550 (Oct. 1, 2005).

Terkeltaub, R. "Physiologic and pathologic functions of the NPP nucleotide pyrophosphatase/phosphodiesterase family focusing on NPP1 in calcification" Purinergic Signalling, 2(2):371-377 (Jun. 1, 2012).

Albright, R.A. et al., "ENPP1-Fc prevents mortality and vascular calcifications in rodent model of generalized arterial calcification of infancy," Nature Communications, vol. 6(1):1-11 (2015).

Askew, K., "Enpp1 Enzyme replacement therapy for generalized arterial calcification of infancy," Alexion Pharmaceuticals, Jul. 4, 2016, 25 pages.

International Preliminary Report on Patentability, PCT/US2018/052795, dated Mar. 31, 2020, 7 pages.

(56) References Cited

OTHER PUBLICATIONS

International Search Report and Written Opinion, PCT/US2018/052795, dated Dec. 11, 2018, 11 pages.
Khan, T. et al., "ENPP1 enzyme replacement therapy improves blood pressure and cardiovascular function in a mouse model of generalized arterial calcification of infancy," Disease Models & Mechanisms, vol. 11 (10): 14 pages (2018).
Rashdan, N. et al., "New perspectives on rare connective tissue calcifying diseases," Current Opinion in Pharmacology, vol. 28:14-23 (2016).
European Patent Office, Communication pursuant to Article 94(3) EPC for European Patent Application No. 18786563.9, dated Mar. 14, 2023, 5 pages.
Japanese Patent Office, Notice of Reasons for Rejection for Japanese Patent Application No. 2020-517388, mailed Mar. 7, 2023, 8 pages.
Li, Q., et al., "Spontaneous asj-2J mutant mouse as a model for generalized arterial calcification of infancy: a large deletion/insertion mutation in the Enpp1 gene," PLoS ONE, vol. 9, No. 12, Dec. 5, 2014, pp. e113542.
Siu, S., et al., "Variable patterns of ectopic mineralization in Enpp1asj-2J mice, a model for generalized arterial calcification of infancy," Oncotarget, 2016, vol. 7, No. 51, pp. 83837-83842.
[No Author Listed] "Breeding Strategies for Maintaining Colonies of Laboratory Mice: A Jackson Laboratory Resource Manual", 2007, 1-29.
Agapov, et al., "Noncytopathic Sindbis virus RNA vectors for heterologous gene expression", Proc. Natl. Acad. Sci. USA vol. 95, 1998, 12989-12994.
Albright, et al., "Molecular basis of purinergic signal metabolism by ectonucleotide pyrophosphatase/ phosphodiesterases 4 and 1 and implications in stroke", J Biol Chem. 289(6) ,2014 , 3294-3306.
Albright, et al., "NPP4 is a procoagulant enzyme on the surface of vascular endothelium", Blood. 120(22) ,2012, 4432-4440.
Altschul, et al., "Basic Local Alignment Search Tool", Journal of Molecular Biology, vol. 215, Issue 3, 1990, 403-410.
Anonymous , "UPI000511D809", Retrieved from the Internet Mar. 7, 2019, <https://www.uniprot.org/uniparc/JP1000 511D809>, Oct. 2014.
Apschner, A., et al., "Pathological mineralization in a zebrafish enpp1 mutant exhibits features of Generalized Arterial Calcification of Infancy (GACI) and Pseudoxanthoma Elasticum (PXE)", Disease Models & Mechanisms, Jul. 1, 2014, 21 pages.
Ayuso, et al., "Production, Purification and Characterization of Aden-Associated Vectors", Current Gene Therapy 2010, 10:423-436.
Baheti et al., "Excipients used in lyophilization of small molecules" IPEC-Americas Inc., p. 41-54, Jun. 2010.
Beck et al., "Therapeutic Fc-fusion Proteins and Peptides as Successful Alternatives to Antibodies," 3:5, 415-416 (2011).
Belisário , et al., "Association between ENPP1 K173Q and stroke in a newborn cohort of 395 Brazilian children with sickle cell anemia", Blood. 126(10), 2015, 1259-1260.
Benoist, et al., "In vivo sequence requirements of the SV40 early promoter region", Nature 290, 1981, 304-310.
Bertrand, et al., "Decreased levels of nucleotide pyrophosphatase phosphodiesterase 1 are associated with cartilage calcification in osteoarthritis and trigger osteoarthritic changes in mice", Annals of the Rheumatic Diseases vol. 71, 2012, 1249-1253.
Blytt, et al., "Assay of Covalent Intermediate of 5'—Nucleotide Phosphodiesterase" Analytical Biochemistry vol. 147, Issue 2, 1985, 517-520.
Boshart, et al., "A Very Strong Enhancer Is Located Upstream of an Immediate Early Gene of Human Cytomegalovirus," Cell vol. 41, Issue 2, 1985, 521-530.
Buckley , et al., "Plasma cell membrane glycoprotein PC-1. cDNA cloning of the human molecule, amino acid sequence, and chromosomal location", J Biol Chem. 265(29), Oct. 1990, 17506-17511.
Caballero , et al., "Impaired urinary osteopontin excretion in Npt2a-/- mice", Am J Physiol Renal Physiol. 312(1), 2017, F77-F83.

Casales, et al., "Development of a new noncytopathic Semliki Forest virus vector providing high expression levels and stability", Virology 376 (2008) 242-251.
Chamow, S. M. et al., "Immunoadhesins: Principles and Applications," Trends Biotechnol., 14(2); 52-60 (1996).
Cheung, et al., "Analysis of Inorganic Pyrophosphate at the Picomole Level", Analytical Biochemistry vol. 83, 1977, 61-63.
Chronic Renal Failure: From the Perspective of Internal Medicine, Clinical Imagiology 21(11), 2005, 1142-1149 (Partial Translation).
Cimpean, et al., "Substrate-specifying determinants of the nucleotide pyrophosphatases/phosphodiesterases NPP1 and NPP2", Biochem J. 381(Pt 1) ,2004, 71-77.
Colella, et al., "Emerging Issues in AAV-Mediated In Vivo Gene Therapy", Molecular Therapy: Methods & Clinical Development vol. 8, 2018, 87-104.
Dabisch-Ruthe, M., et al., "Pyrophosphates as a major inhibitor of matrix calcification in Pseudoxanthoma elasticum," Journal of Dermatological Science, Elsevier, Amsterdam, NL, vol. 75, No. 2, May 17, 2014, pp. 109-120.
Dabisch-Ruthe, M., et al., "Variants in genes encoding pyrophosphate metabolizing enzymes are associated with Pseudoxanthoma eslasticum," Clinical Biochemsitry, 2014, vol. 47, No. 15, pp. 60-67.
Dall'Acqua, et al. "Increasing the affinity of a human IgG1 for the neonatal Fc receptor: biological consequences." The Journal of Immunology 169.9 (2002): 5171-5180.
Dasgupta, et al., "Mutations in SLC34A3/NPT2c are associated with kidney stones and nephrocalcinosis", J Am Sac Nephrol. 25(10), 2014, 2366-2375.
Dong, H., et al., "Increased Hepatic Levels of the Insulin Receptor Inhibitor, PC-1/NPP1, Induce Insulin Resistance and Glucose Intolerance," Diabetes Feb. 1, 2005; 54 (2), pp. 367-372.
Eller, et al. "Impact of ENPP1 genotype on arterial calcification in patients with end-stage renal failure", Nephrol Dial Transplant. 23(1), 2008, 321-327.
Fang, L., et al., "PDGF C Is A Selective alpha Platelet-Derived Growth Factor Receptor Agonist That Is Highly Expressed in Platelet alpha Granules and Vascular Smooth Muscle," Arterioscler. Thromb. Vasc. Biol. 24, 2004, 787-92.
Flanagan , et al., "Genetic mapping and exome sequencing identify 2 mutations associated with stroke protection in pediatric patients with sickle cell anemia", Blood. 121(16), 2013, 3237-3245.
Flanagan, et al., "Soluble Fc fusion proteins for biomedical research," in Monoclonal Antibodies, Methods and Protocols, et. By Albitar, Methods in Molecular Biology, (2007) vol. 378, 33-52.
Fleisch , et al., "Inhibitors and promoters of stone formation", Kidney Int. 13(5), 1978, 361-371.
Frolov, et al., "Selection of RNA Replicons Capable of Persistent Noncytopathic Replication in Mammalian Cells", Journal of Virology, 1999, 3854-3865.
Gijsbers , et al., "Functional characterization of the non-catalytic ectodomains of the nucleotide pyrophosphatase/phosphodiesterase NPP1", Biochem J. 371(Pt 2), Apr. 15, 2003, 321-330.
Gijsbers , et al., "The hydrolysis of lysophospholipids and nucleotides by autotaxin (NPP2) involves a single catalytic site," FEBS Letters, 538:60-64 (2003).
Gijsbers, et al., "Structural and Catalytic Similarities between Nucleotide Pyrophosphatases/Phosphodiesterases and Alkaline Phosphatases", The Journal of Biological Chemistry vol. 276, No. 2, 2001, 1361-1368.
Goldman, et al., Hydrolysis of diadenosine 5',5"-P', P"'-triphosphate (Ap3A) by porcine aortic endothelial cells, Circ Res. 59(3), 1986 , 362-366.
Green, et al., "Analysis of human tonsil and cancer DNAs and RNAs for DNA sequences of group C (serotypes 1, 2, 5, and 6) human adenoviruses", Proc. Natl. Acad. Sci. USA 1979, vol. 76, No. 12, 6606-6610.
Guan, et al., "Peptide-Targeted Polyglutamic Acid Doxorubicin Conjugates for the Treatment of αvβ6-Positive Cancers," Bioconjug Chem., 19:1813-1821 (2008).
Guanabens, N., et al., "Calcific Periarthritis as the Only Clinical Manifestation of Hypophosphatasia in Middle-Aged Sisters," Journal of Bone ande Mineral Research, 2014, vol. 29, No. 4, pp. 929-934.

(56) References Cited

OTHER PUBLICATIONS

Guo et al., "Clinical outcomes of various continued antiplatelet therapies in patients who were administered DAPT following the implantation of drug-eluting stents and developed gastrointestinal hemorrhage", Exp Ther Med. 12(2), Aug. 2016, 1125-1129.
Halbert, et al., "AAV-Mediated Gene Transfer to Mouse Lungs", Methods in Molecular Biology, vol. 246, 2004, 201-212.
Huang, "Receptor-Fc Fusion Therapeutics, traps, and MIMETIBODY Technology," Current Opinion in Biotechnology, 20:692-699 (2009).
Jansen, et al., "ABCC6 prevents ectopic mineralization seen in pseudoxanthoma elasticum by inducing cellular nucleotide release", Proc Natl Acad Sci U S A. 110(50), 2013, 20206-20211.
Jansen, et al., "ABCC6-mediated ATP secretion by the liver is the main source of the mineralization inhibitor inorganic pyrophosphate in the systemic circulation-brief report", Arterioscler Thromb Vasc Biol. 34(9), 2014, 1985-1989.
Jansen, et al., "Proteolytic maturation and activation of autotaxin (NPP2), a secreted metastasis-enhancing lysophospholipase D", J Cell Sci. 118(Pt 14), 2005, 3081-3089.
Jia, et al., "A novel model of adenine-induced tubulointerstitial nephropathy in mice", BMC Nephrology 2013, 14: 116.
Jiang, et al., "Aberrant Mineralization of Connective Tissues in a Mouse Model of Pseudoxanthoma Elasticum: Systemic and Local Regulatory Factors", Journal of Investigative Dermatology 2007, 127(6): 1392-1402.
Jin-Hua, et al., "Molecular Coning and Chromosomal Localization of PD-113 (PDNP3), a New Member of the Human Phosphodiesterase I Genes", Genomics 45, 1997, 412-415.
Schmidt, "Fusion Proteins as Biopharmaceuticals—Applications and Challenges," Current Opinion in Drug Discovery & Development, 12:1-12 (2009).
Schwartz, et al., "Clinical Evaluation of Live, Oral Types 1,2, and 5 Adenovirus Vaccines", American Review of Respiratory Disease vol. 109, 1974, 233-238.
Shankar, et al., "Progeria-A Brief Review", International Journal of Pharma and Bio Sciences 2, 2010, 1-14.
Shaw, G., et al., "Preferential transformation of human neuronal cells by human adenoviruses and the origin of HEK 293 cells," FASEB J. 16, 2002, 19 pages.
Sheehan, et al., "Genetic modifiers of sickle cell anemia in the BABY HUG cohort: influence on laboratory and clinical phenotypes", Am J Hematol. 88(7), 2013, 571-576.
Shimamura, et al., "A Progressive Glomerulosclerosis Occuring in Partial Five-sixths Nephrectomized Rats", Am. J. Pathol. 1975, 79(1): 95-106.
Silcox, et al., "Measurement of inorganic pyrophosphate in biological fluids. Elevated levels in some patients with osteoarthritis, pseudogout, acromegaly, and uremia", J Clin Invest. 52(8), Aug. 1973, 1863-1870.
Singer, M., et al., Genes and Genomes, "Mir", Moscow, 1998, vol. 1, pp. 1-369, in Russian. English translation of relevant parts.
Tsai, et al., "The Ectoenzyme E-NPP3 Negatively Regulates ATP—Dependent Chronic Allergic Responses by basophils and Mast Cells", Immunity 42, Feb. 2015, 279-293.
UniProt Accession No. O14638, ENPP3 Human, Jan. 7, 2015 [online]. [Retrieved on Jan. 19, 2017]. Retrieved from the internet <URL: http://www.uniprot.org/uniprot/O14638.txt?version=133>.
Uniprot, Accession No. P22413, 2009, www.uniprot.org. (Year: 2009).
Van Meeteren, et al., "Inhibition of autotaxin by lysophosphatidic acid and sphingosine 1-phosphate", J Biol Chem. 280(22), Jun. 2005, 21155-21161.
Villa-Bellosta, et al., "Defective Extracellular Pyrophosphate Metabolism Promotes Vascular Calcification in a Mouse Model of Hutchinson-Gilford Progeria Syndrome That is Ameliorated on Pyrophosphate Treatment", Circulation vol. 127, Issue 24, 2013, 2442-2451.
Virag, et al., "Producing Recombinant Adeno-Associated Virus in Foster Cells: Overcoming Production Limitations Using a Baculovirus-Insect Cell Expression Strategy", Human Gene Therapy 20: 807-817 (2009).
Vollmayer, et al., "Hydrolysis of diadenosine polyphosphates by nucleotide pyrophosphatases/phosphodiesterases," Eur J Biochem. 270(14),2003, 2971-2978.
Wagner, et al., "Nucleotide sequence of the thymidine kinase gene of herpes simplex virus type 1", Proc. Natl. Acad. Sci. USA vol. 78, No. 3, 1981, 1441-1445.
Wang, et al., "Pharmacokinetic and Biodistribution Studies of a Bone-targeting Drug Delivery System Based on N-(2-Hydroxypropyl)methacrylamide (HPMA) Copolymers," Molecular Pharmaceutics 3(6): 717-725 (2006).
Ware, et al., "Targeted disruption of the low-affinity leukemia inhibitory factor receptor gene causes placental, skeletal, neural and metabolic defects and results in perinatal death", Development 121, 1283-1299 (1995).
Whisstock, et al., "Prediction of proteinfunction fromprotein sequence and structure", Quarterly Reviews of Biophysics 36, 3 (2003), pp., 2003, 307-340.
Witkowski, et al., "Conversion of a Beta-Ketoacyl Synthase to a Malonyl Decarboxylase by Replacement of the Active-Site Cysteine With Glutamine", Biochemistry 38(36), Sep. 1999, 11643-11650.
Wu, et al., "Hyperuricemia and urate nephropathy in urate oxidase-deficient mice", Proc. Natl. Acad. Sci. USA vol. 91, 742-746 (1994).
Wu, et al., "Interstitial Calcinosis in Renal Papillae of Genetically Engineered Mouse Models: Relation to Randall's Plaques", Urolithiasis 43, 65-76 (2015).
Yamamoto, et al., "Identification of a Functional Promoter in the Long Terminal Repeat of Rous Sarcoma Virus", Cell vol. 22, 1980, 787-797.
Zee, et al., "α-Lipoic acid treatment prevents cystine urolithiasis in a mouse model of cystinuria", Nat Med. 2017, 23 (3): 288-290.
Zettervall, S., et al., "Association of arterial calcification with chronic limb ischemia in patients with peripheral artery disease," Journal of Vascular Surgery, Feb. 2018, vol. 67, No. 2, pp. 507-513.
Zhang, et al., "The interaction of cationic polymers and their bisphosphonate derivatives with hydroxyapatite", Macromol Biosci. 7(5), May 10, 2007, 656-670 (Abstract Only).
Zhang, et al., "Adenovirus-Adeno-Associated Virus Hybrid for Large-Scale Recombinant Adeno-Associated Virus Production", Human Gene Therapy 2009, vol. 20, No. 9, 922-929.
Zhang, et al., "Investigation of the role of ENPP1 and TNAP genes in chondrocalcinosis," Rheumatology, vol. 46, Issue 4, Apr. 2007, pp. 586-589.
Johnson, et al., "Matrix vesicle plasma cell membrane glycoprotein-1 regulates mineralization by murine psteoblastic MC3T3 cells", J Bone Miner Res. 14(6), Jun. 1999, 883-892.
Johnson, et al. "The nucleoside triphosphate pyrophosphohydrolase isozyme PC-1 directly promotes cartilage calcification through chondrocyte apoptosis and increased calcium precipitation by mineralizing vesicles." The Journal of Rheumatology 28.12 (2001): 2681-2691.
Johnson, et al., "Chondrogenesis Mediated by PPi Depletion Promotes Spontaneous Aortic Calcification in NPP1-/-Mice" Arteriosclerosis Thrombosis, and Vascular Biology, 25: 686-691 (2005).
Johnson, et al., "Differential mechanisms of inorganic pyrophosphate production by plasma cell membrane glycoprotein-1 and B10 in chondrocytes", Arthritis Rheum. 42(9), 1999, 1986-1997.
Johnson, et al., "Kabat database and its applications: 30 years after the first variability plot," Nucleic Acids Res. 28 (1), Jan. 2000, 214-218.
Kato, et al., "Crystal structure of Enpp1, an extracellular glycoprotein involved in bone mineralization and insulin signaling", Proc Natl Arad Sci U S A. 109(42), Oct. 2012, 16876-16881.
Kato, et al., "Identification of ENPP1 Haploinsufficiency in Patients With Diffuse Idiopathic Skeletal Hyperostosis and Early-Onset Osteoporosis," Journal of Bone and Mineral Research 2022, vol. 37, pp. 1125-1135.
Khan, et al., "Experimental Induction of Calcium Oxalate Nephrolithiasis in Mice", The Journal of Urology 2010, vol. 184, Issue 3, 1189-1196.
Khan, et al., "Ultrastructural Investigation of Crystal deposits in Npt2a knockout mice: Are they similar to Human Randall's plaques?" J Urol. 2011, 186(3): 1107-1113.

(56) References Cited

OTHER PUBLICATIONS

Kober, et al., "Optimized Signal Peptides for the Development of High Expressing CHO Cell Lines", Biotechnology and Bioengineering, 2013, 110(4): 1164-1173.
Lee, et al., "Cloning' chromosomal localization, and tissue expression of autotaxin from human teratocarcinoma cells", Biochem Biophys Res Commun. 218(3), 1996, 714-719.
Levy-Litan, et al., "Autosomal-Recessive Hypophosphatemic Rickets Is Associated with an Inactivation Mutation in the ENPP1 Gene", The American Journal of Human Genetics 86, 273-278, 2010.
Li, et al., "Response of Npt2a knockout mice to dietary calcium and phosphorus", PLoS One. 12(4), 2017, e0176232.
Li, et al. "Serum phosphate concentration and incidence of stroke: a systemic review and meta-analysis." Neurological sciences 35.12 (2014): 1877-1882.
Li, et al., "Mutant Enpp1 asj mice as a model for generalized arterial calcification of infancy", Disease Models & Mechanisms 6, 1227-1235 (2013).
Liang, et al., "Survey of the Enthesopathy of X-Linked Hypophosphatemia and Its Characterization in Hyp Mice", Calcif. Tissue Int. 2009, 85(3): 235-46.
Lieben, et al., "Normocalcemia is maintained in mice under conditions of calcium malabsorption by vitamin D-induced inhibition of bone mineralization", J Clin Invest. 122(5), 2012, 1803-1805.
Lock, et al., "Characterization of a Recombinant Adeno-Associated Virus Type 2 Reference Standard Material", Human Gene Therapy 21: 1273-1285 (2010).
Lomashvili, et al., "Phosphate-induced vascular calcification: role of pyrophosphate and osteopontin," Journal of American Society of Nephrology, 1392-1401, Mar. 4, 2004.
Lust, et al., "A rapid, enzymatic assay for measurement of inorganic pyrophosphate in biological samples", Clinica Chimica Acta 66, 1976, 241-249.
Mackenzie, et al., "Altered Bone Development and an Increase in FGF-23 Expression in Enpp1 -/- Mice", PLoS one 2012, 7(2): e32177.
Millán, et al., "Enzyme replacement therapy for murine hypophosphatasia", J Bone Miner Res. 23(6), Jun. 2008, 777-787.
Morrison, et al., "Experimentally Induced Chronic Renal Insufficiency in the Rat", Laboratory Investigation vol. 11, 1962, 321-332.
Murphy, et al., "Synthesis and in vitro hydroxyapatite binding of peptides conjugated to calcium-binding moieties," Biomacromolecules, 8:2237-2243 (2007).
Mus musculus domesticus ecto-nucleotide pyrophosphatase/phosphodiesterase-1 mRNA, complete cds, GenBank J027002, Aug. 12, 2020 searched.
Nagase, et al., Uniprot Submission Accession No. Q9Y6X5 (online at <www.uniprot.org/uniprot/Q9Y6X5.txt?uersion=66>), 2011.
Nakamura, et al., "Association of the human NPPS gene with ossification of the posterior longitudinal ligament of the spine (OPLL)", Human Genetics, 1999, 104(6): 492-497.
Nakanishi, et al. "Development and therapeutic application of transposon-based vectors." Yakugaku Zasshi: Journal of the Pharmaceutical Society of Japan 129.12 (2009): 1433-1443.
Nishioka, et al., "Enhancement of drug delivery to bone: characterization of human tissue-nonspecific alkaline phosphatase tagged with an acidic oligopeptide," Molecular Genetics and Metabolism vol. 88, Issue 3, Jul. 2006, pp. 244-255.
Nitschke, Y., et al., "Generalized arterial calcification of infancy and pseudoxanthoma elasticum: two sides of the same coin," Frontiers in Genetics 2012, vol. 3 302, 3 pages.
O'NeilL, et al., "Treatment with pyrophosphate inhibits uremic vascular calcification," International Society of Nephrology, 512-517, Mar. 2011.
Ogilvie, et al., Identification and partial characterization of an adenosine(5')tetraphospho(5')adenosine hydrolase on intact bovine aortic endothelial cells, Biochem J. 259(1), 1989,97-103.

Okawa, et al., "Mutation in Npps in a mouse model of ossification of the posterior longitudinal ligament of the spine", Nat Genet. 19(3), Jul. 1998, 271-273.
Otero, J., et al., "Severe Skeletal Toxicity From Protracted Etidronate Therapy for Generalized Arterial Calcification of Infancy," Journal of Bone and Mineral Research, 2013, vol. 28, No. 2, pp. 419-430.
Papadakis, et al., "Promoters and Control Elements: Designing Expression Cassettes for Gene Therapy", Current Gene Therapy, 2004, 4, 89-113.
Parfitt, et al., "Bone histomorphometry: Standardization of nomenclature, symbols, and units: Report of the asbmr histomorphometry nomenclature committee", Journal of Bone and Mineral Research vol. 2, 1987, 595-610.
Pharmacokinetic Control of Biopharmaceuticals, Journal of Pharmaceutical Science and Technology, Japan, 2014, 27-32 (Partial Translation).
Rath, et al. "Fc-fusion proteins and FcRn: structural insights for longer-lasting and more effective therapeutics." Critical reviews in biotechnology 35.2 (2015): 235-254.
Ratkalkar, et al., "Mechanisms of Stone Formation", Clin Rev Bone Miner Metab. 9(3-4), 2011, 187-197.
Robbie, et al. "A novel investigational Fc-modified humanized monoclonal antibody, motavizumab-YTE, has an axtended half-life in healthy adults." Antimicrobial agents and chemotherapy 57.12 (2013): 6147-6153.
Rogers, et al. "Recombinant human serum albumin fusion proteins and novel applications in drug delivery and therapy." Current pharmaceutical design 21.14 (2015): 1899-1907. Abstract.
Rosenfeld, et al., "Adenovirus-Mediated Transfer of a Recombinant Alpha 1-Antitrypsin Gene to the Lung Epithelium in Vivo", Science vol. 252, 1991, 431-434.
Rosenfeld, et al., "In Vivo Transfer of the Human Cystic Fibrosis Transmembrane Conductance Regulator Gene to the Airway Epithelium", 1992, Cell 68: 143-155.
Rutsch, et al., "Mutations in ENPP1 are associated with 'idiopathic' infantile arterial calcification," Nature Genetics, 34: (4) 379-381 (2003).
Sahota, et al., "Novel cystine ester mimics for the treatment of cystinuria-induced urolithiasis in a knockout mouse model", Urology 2014, 84(5): 1249 e9-15.
Sakagami, et al., Biochemical and molecular characterization of a novel choline-specific glycerophosphodiester phosphodiesterase belonging to the nucleotide pyrophosphatase/phosphodiesterase family, J Biol Chem. 280 (24) ,2005, 23084-23093.
Saunders, et al., "Identification of small-molecule inhibitors of autotaxin that inhibit melanoma cell migration and invasion" Mol. Cancer Ther. 7(10): 3352-62 (2008).
Saunders, et al.,"Kinetic analysis of autotaxin reveals substrate-specific catalytic pathways and a mechanism for lysophosphatidic acid distribution," J Biol Chem. 286(34), 2011,30130-30141.
Sayer "Progress in understanding the genetics of calcium-containing nephrolithiasis." Journal of the American Society of Nephrology 28.3 (2017): 748-759.
Schetter, et al., "Nucleoporins NPP-1, NPP-3, NPP-4, NPP-11 and NPP-13 are required for proper spindle orientation in C. elegans", Dev Biol. 289(2), Jan. 15, 2006, 360-371.
Chen, et al., "Fusion Protein Linkers: Property, Design and Functionality", Adv Drug Deliv Rev., 65 (10), pp. 1357-1369, Oct. 15, 2013 (Oct. 15, 2013).
Genbank Accession No. XP _006144365.1, Retrieved from the Internet «https://www.ncbi.nlm.nih.gov/protein/XP_006144365.1?report=genbank&log$=protalign&blast_rank=92&RI D=X9E_1 SC3Z016», Retrieved on Feb. 20, 2024.
Goding, et al., "Ecto-phosphodiesterase/pyrophosphatase of lymphocytes and non-lymphoid cells: Structure and function of the PC-1 family," Immunological Reviews, 161: 11-26 (1998).
Kassim, et al., "Prevention and Treatment of Stroke in Patients With Sickle Cell Disease," Clinical Advances in Hematology & Oncology vol. 14, Issue May 5, 2016 pp. 307-309.
Koike, et al., "The N-terminal hydrophobic sequence of autotaxin (ENPP2) functions as a signal peptide", Genes to Cells, 11 (2), pp. 133-142, Jan. 4, 2006.

(56) References Cited

OTHER PUBLICATIONS

Luthje, et al., "Diadenosine triphosphate (Ap3A) mediates human platelet aggregation by liberation of ADP," Biochem Biophys Res Commun. 118(3), 1984, 704-709.
NCBI Accession No. NM_006208, Mar. 2001.
Nitschke, Y., et al., "Generalized arterial calcification of infancy and pseudoxanthoma elasticum can be caused by mutations in either ENPP1 or ABCC6," Am J Hum Genet. Jan. 13, 2012;90(1):25-39.
Nitschke, Y., et al., "Inherited Arterial Calcification Syndromes: Etiologies and Treatment Concepts," Curr Osteoporos Rep. Aug. 2017; 15(4):255-270.
Okada, et al., "Scalable purification of adeno-associated virus serotype 1 (AAV1) and AAV8 vectors, using dual ion-exchange adsorptive membranes", Human Gene Therapy vol. 20, 2009, 1013-1021.
Printout of bleeding disorders from the American Society of Hematology, downloaded Sep. 11, 2017 from world wide web. hematology.org/Patients?Bleeding.aspx, 5 pages.
Yin, et al. "Glycoengineering of Chinese hamster ovary cells for enhanced erythropoietin N-glycan branching and sialylation." Biotechnology and bioengineering 112.11 (2015): 2343-2351.
Yan, Y., et al., "Abstract P292: ENPP1-Fc Protein Inhibits Proliferation of Human Vascular Smooth Muscle Cells", Hypertension, vol. 68, No. suppl 1, Sep. 1, 2016.

\* cited by examiner

Pressure Volume Loops indicate that Enpp1 treatment reduces ventricle stiffness (EDPVR) and increases contractility (PRSW) in Asj-2J mice
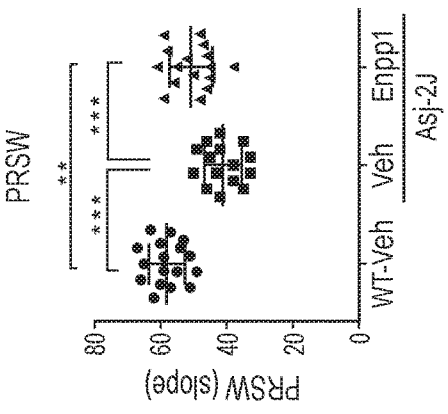
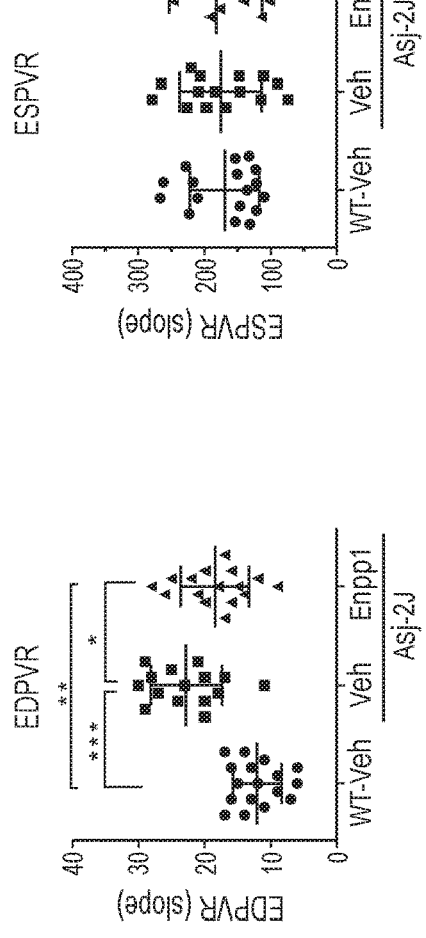
FIG. 5C
FIG. 5B
FIG. 5A
\*\*\* p<0.0001
\*\* p<0.001
\* p<0.05
One-Way ANOVA with Tukey's multiple comparison test

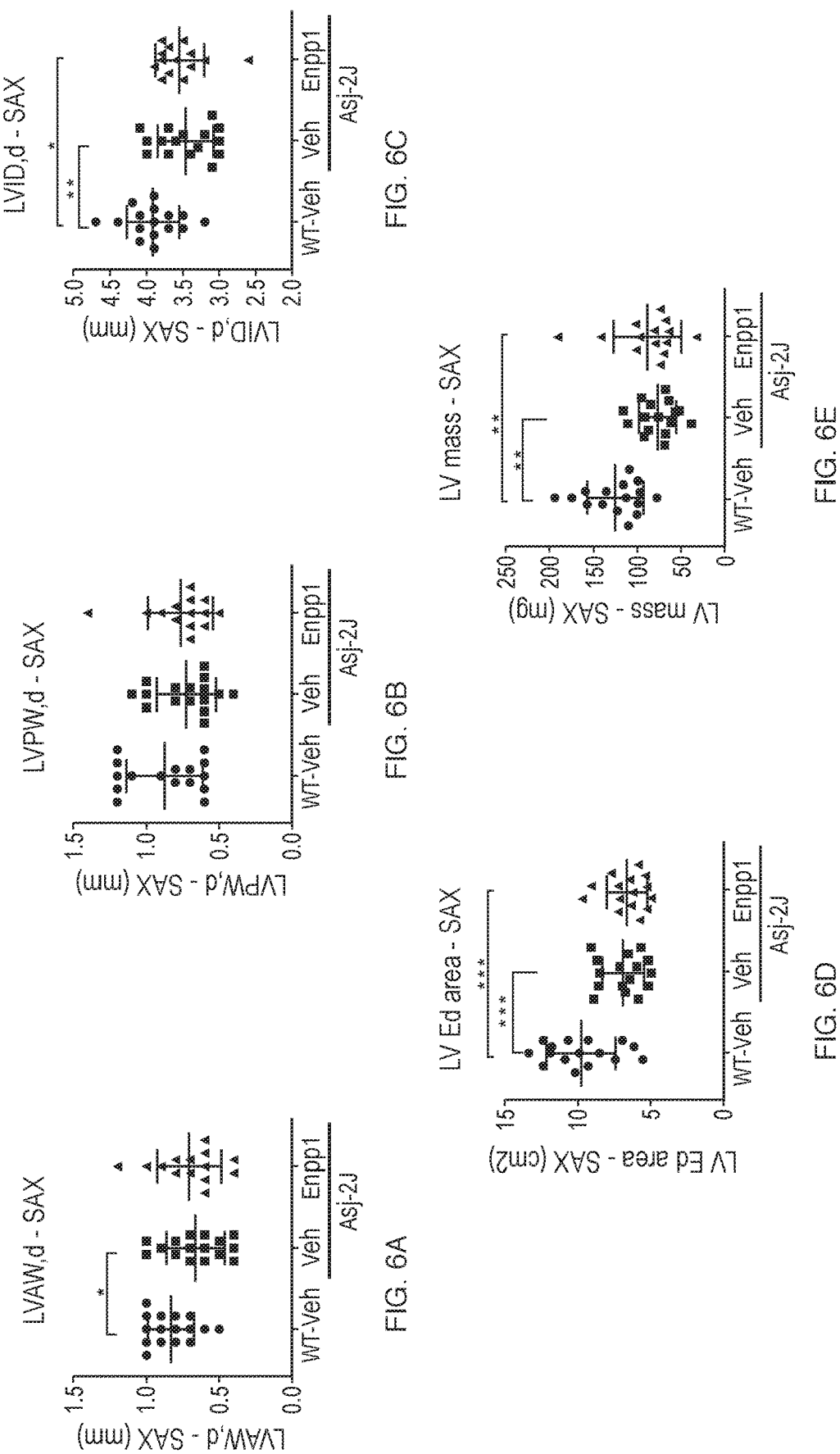

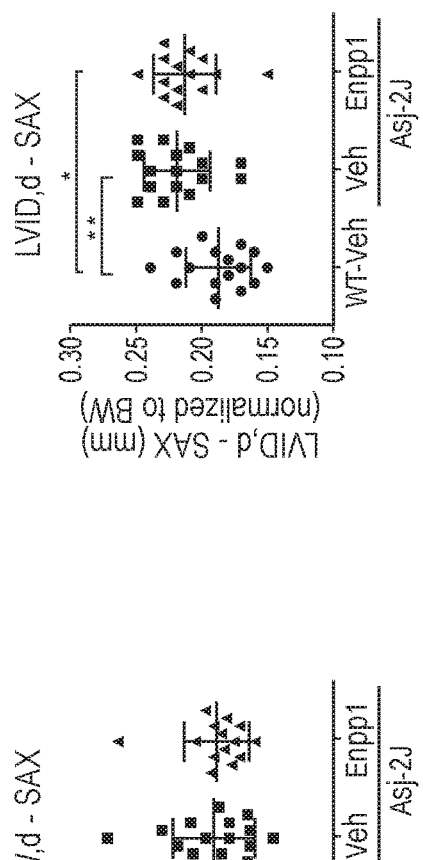
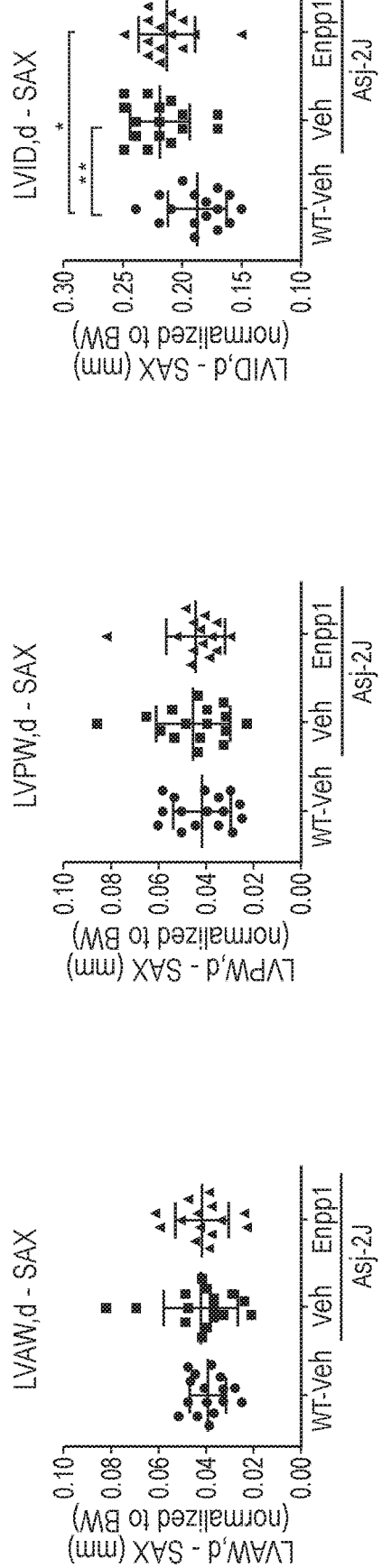
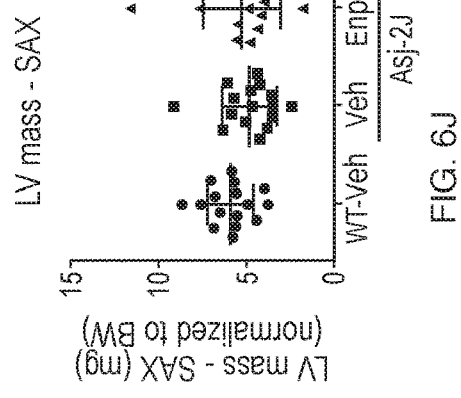
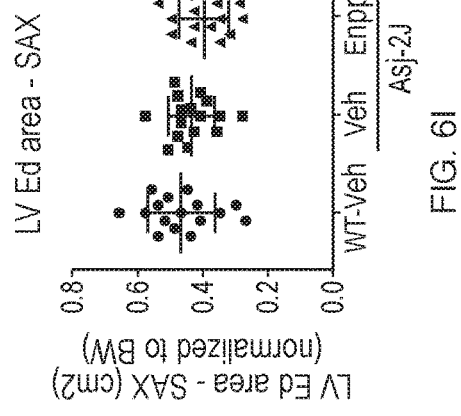
FIG. 6F, FIG. 6G, FIG. 6H, FIG. 6I, FIG. 6J
ECHO suggests Asj-2J mice do not have left ventricular hypertrophy no change in LV Diastolic Anterior/Posterior Wall Thickness, internal dimensions, End-Diastolic Area, and Estimated LV Mass
Normalized to BW

SEQUENCE LISTING

<160> NUMBER OF SEQ ID NOS: 21

<210> SEQ ID NO 1
<211> LENGTH: 925
<212> TYPE: PRT
<213> ORGANISM: Homo sapiens

<400> SEQUENCE: 1

```
Met Glu Arg Asp Gly Cys Ala Gly Gly Gly Ser Arg Gly Gly Glu Gly
1               5                   10                  15

Gly Arg Ala Pro Arg Glu Gly Pro Ala Gly Asn Gly Arg Asp Arg Gly
            20                  25                  30

Arg Ser His Ala Ala Glu Ala Pro Gly Asp Pro Gln Ala Ala Ala Ser
        35                  40                  45

Leu Leu Ala Pro Met Asp Val Gly Glu Glu Pro Leu Glu Lys Ala Ala
    50                  55                  60

Arg Ala Arg Thr Ala Lys Asp Pro Asn Thr Tyr Lys Val Leu Ser Leu
65                  70                  75                  80

Val Leu Ser Val Cys Val Leu Thr Thr Ile Leu Gly Cys Ile Phe Gly
                85                  90                  95

Leu Lys Pro Ser Cys Ala Lys Glu Val Lys Ser Cys Lys Gly Arg Cys
            100                 105                 110

Phe Glu Arg Thr Phe Gly Asn Cys Arg Cys Asp Ala Ala Cys Val Glu
        115                 120                 125

Leu Gly Asn Cys Cys Leu Asp Tyr Gln Glu Thr Cys Ile Glu Pro Glu
    130                 135                 140
```

-continued

```
His Ile Trp Thr Cys Asn Lys Phe Arg Cys Gly Glu Lys Arg Leu Thr
145                 150                 155                 160

Arg Ser Leu Cys Ala Cys Ser Asp Asp Cys Lys Asp Lys Gly Asp Cys
            165                 170                 175

Cys Ile Asn Tyr Ser Ser Val Cys Gln Gly Glu Lys Ser Trp Val Glu
            180                 185                 190

Glu Pro Cys Glu Ser Ile Asn Glu Pro Gln Cys Pro Ala Gly Phe Glu
        195                 200                 205

Thr Pro Pro Thr Leu Leu Phe Ser Leu Asp Gly Phe Arg Ala Glu Tyr
    210                 215                 220

Leu His Thr Trp Gly Gly Leu Leu Pro Val Ile Ser Lys Leu Lys Lys
225                 230                 235                 240

Cys Gly Thr Tyr Thr Lys Asn Met Arg Pro Val Tyr Pro Thr Lys Thr
                245                 250                 255

Phe Pro Asn His Tyr Ser Ile Val Thr Gly Leu Tyr Pro Glu Ser His
            260                 265                 270

Gly Ile Ile Asp Asn Lys Met Tyr Asp Pro Lys Met Asn Ala Ser Phe
        275                 280                 285

Ser Leu Lys Ser Lys Glu Lys Phe Asn Pro Glu Trp Tyr Lys Gly Glu
    290                 295                 300

Pro Ile Trp Val Thr Ala Lys Tyr Gln Gly Leu Lys Ser Gly Thr Phe
305                 310                 315                 320

Phe Trp Pro Gly Ser Asp Val Glu Ile Asn Gly Ile Phe Pro Asp Ile
                325                 330                 335

Tyr Lys Met Tyr Asn Gly Ser Val Pro Phe Glu Glu Arg Ile Leu Ala
            340                 345                 350

Val Leu Gln Trp Leu Gln Leu Pro Lys Asp Glu Arg Pro His Phe Tyr
        355                 360                 365

Thr Leu Tyr Leu Glu Glu Pro Asp Ser Ser Gly His Ser Tyr Gly Pro
    370                 375                 380

Val Ser Ser Glu Val Ile Lys Ala Leu Gln Arg Val Asp Gly Met Val
385                 390                 395                 400

Gly Met Leu Met Asp Gly Leu Lys Glu Leu Asn Leu His Arg Cys Leu
                405                 410                 415

Asn Leu Ile Leu Ile Ser Asp His Gly Met Glu Gln Gly Ser Cys Lys
            420                 425                 430

Lys Tyr Ile Tyr Leu Asn Lys Tyr Leu Gly Asp Val Lys Asn Ile Lys
        435                 440                 445

Val Ile Tyr Gly Pro Ala Ala Arg Leu Arg Pro Ser Asp Val Pro Asp
    450                 455                 460

Lys Tyr Tyr Ser Phe Asn Tyr Glu Gly Ile Ala Arg Asn Leu Ser Cys
465                 470                 475                 480

Arg Glu Pro Asn Gln His Phe Lys Pro Tyr Leu Lys His Phe Leu Pro
                485                 490                 495

Lys Arg Leu His Phe Ala Lys Ser Asp Arg Ile Glu Pro Leu Thr Phe
            500                 505                 510

Tyr Leu Asp Pro Gln Trp Gln Leu Ala Leu Asn Pro Ser Glu Arg Lys
        515                 520                 525

Tyr Cys Gly Ser Gly Phe His Gly Ser Asp Asn Val Phe Ser Asn Met
    530                 535                 540

Gln Ala Leu Phe Val Gly Tyr Gly Pro Gly Phe Lys His Gly Ile Glu
545                 550                 555                 560
```

-continued

Ala Asp Thr Phe Glu Asn Ile Glu Val Tyr Asn Leu Met Cys Asp Leu
            565                 570                 575

Leu Asn Leu Thr Pro Ala Pro Asn Asn Gly Thr His Gly Ser Leu Asn
        580                 585                 590

His Leu Leu Lys Asn Pro Val Tyr Thr Pro Lys His Pro Lys Glu Val
    595                 600                 605

His Pro Leu Val Gln Cys Pro Phe Thr Arg Asn Pro Arg Asp Asn Leu
610                 615                 620

Gly Cys Ser Cys Asn Pro Ser Ile Leu Pro Ile Glu Asp Phe Gln Thr
625                 630                 635                 640

Gln Phe Asn Leu Thr Val Ala Glu Glu Lys Ile Ile Lys His Glu Thr
            645                 650                 655

Leu Pro Tyr Gly Arg Pro Arg Val Leu Gln Lys Glu Asn Thr Ile Cys
        660                 665                 670

Leu Leu Ser Gln His Gln Phe Met Ser Gly Tyr Ser Gln Asp Ile Leu
    675                 680                 685

Met Pro Leu Trp Thr Ser Tyr Thr Val Asp Arg Asn Asp Ser Phe Ser
690                 695                 700

Thr Glu Asp Phe Ser Asn Cys Leu Tyr Gln Asp Phe Arg Ile Pro Leu
705                 710                 715                 720

Ser Pro Val His Lys Cys Ser Phe Tyr Lys Asn Asn Thr Lys Val Ser
            725                 730                 735

Tyr Gly Phe Leu Ser Pro Pro Gln Leu Asn Lys Asn Ser Ser Gly Ile
        740                 745                 750

Tyr Ser Glu Ala Leu Leu Thr Thr Asn Ile Val Pro Met Tyr Gln Ser
    755                 760                 765

Phe Gln Val Ile Trp Arg Tyr Phe His Asp Thr Leu Leu Arg Lys Tyr
    770                 775                 780

Ala Glu Glu Arg Asn Gly Val Asn Val Val Ser Gly Pro Val Phe Asp
785                 790                 795                 800

Phe Asp Tyr Asp Gly Arg Cys Asp Ser Leu Glu Asn Leu Arg Gln Lys
            805                 810                 815

Arg Arg Val Ile Arg Asn Gln Glu Ile Leu Ile Pro Thr His Phe Phe
        820                 825                 830

Ile Val Leu Thr Ser Cys Lys Asp Thr Ser Gln Thr Pro Leu His Cys
    835                 840                 845

Glu Asn Leu Asp Thr Leu Ala Phe Ile Leu Pro His Arg Thr Asp Asn
850                 855                 860

Ser Glu Ser Cys Val His Gly Lys His Asp Ser Ser Trp Val Glu Glu
865                 870                 875                 880

Leu Leu Met Leu His Arg Ala Arg Ile Thr Asp Val Glu His Ile Thr
            885                 890                 895

Gly Leu Ser Phe Tyr Gln Gln Arg Lys Glu Pro Val Ser Asp Ile Leu
        900                 905                 910

Lys Leu Lys Thr His Leu Pro Thr Phe Ser Gln Glu Asp
    915                 920                 925

<210> SEQ ID NO 2
<211> LENGTH: 827
<212> TYPE: PRT
<213> ORGANISM: Homo sapiens

<400> SEQUENCE: 2

```
Pro Ser Cys Ala Lys Glu Val Lys Ser Cys Lys Gly Arg Cys Phe Glu
1               5                   10                  15

Arg Thr Phe Gly Asn Cys Arg Cys Asp Ala Ala Cys Val Glu Leu Gly
            20                  25                  30

Asn Cys Cys Leu Asp Tyr Gln Glu Thr Cys Ile Glu Pro Glu His Ile
                35                  40                  45

Trp Thr Cys Asn Lys Phe Arg Cys Gly Glu Lys Arg Leu Thr Arg Ser
        50                  55                  60

Leu Cys Ala Cys Ser Asp Asp Cys Lys Asp Lys Gly Asp Cys Cys Ile
65                  70                  75                  80

Asn Tyr Ser Ser Val Cys Gln Gly Glu Lys Ser Trp Val Glu Glu Pro
                85                  90                  95

Cys Glu Ser Ile Asn Glu Pro Gln Cys Pro Ala Gly Phe Glu Thr Pro
                100                 105                 110

Pro Thr Leu Leu Phe Ser Leu Asp Gly Phe Arg Ala Glu Tyr Leu His
            115                 120                 125

Thr Trp Gly Gly Leu Leu Pro Val Ile Ser Lys Leu Lys Lys Cys Gly
    130                 135                 140

Thr Tyr Thr Lys Asn Met Arg Pro Val Tyr Pro Thr Lys Thr Phe Pro
145                 150                 155                 160

Asn His Tyr Ser Ile Val Thr Gly Leu Tyr Pro Glu Ser His Gly Ile
                165                 170                 175

Ile Asp Asn Lys Met Tyr Asp Pro Lys Met Asn Ala Ser Phe Ser Leu
            180                 185                 190

Lys Ser Lys Glu Lys Phe Asn Pro Glu Trp Tyr Lys Gly Glu Pro Ile
        195                 200                 205

Trp Val Thr Ala Lys Tyr Gln Gly Leu Lys Ser Gly Thr Phe Phe Trp
    210                 215                 220

Pro Gly Ser Asp Val Glu Ile Asn Gly Ile Phe Pro Asp Ile Tyr Lys
225                 230                 235                 240

Met Tyr Asn Gly Ser Val Pro Phe Glu Glu Arg Ile Leu Ala Val Leu
                245                 250                 255

Gln Trp Leu Gln Leu Pro Lys Asp Glu Arg Pro His Phe Tyr Thr Leu
            260                 265                 270

Tyr Leu Glu Glu Pro Asp Ser Ser Gly His Ser Tyr Gly Pro Val Ser
        275                 280                 285

Ser Glu Val Ile Lys Ala Leu Gln Arg Val Asp Gly Met Val Gly Met
290                 295                 300

Leu Met Asp Gly Leu Lys Glu Leu Asn Leu His Arg Cys Leu Asn Leu
305                 310                 315                 320

Ile Leu Ile Ser Asp His Gly Met Glu Gln Gly Ser Cys Lys Lys Tyr
                325                 330                 335

Ile Tyr Leu Asn Lys Tyr Leu Gly Asp Val Lys Asn Ile Lys Val Ile
            340                 345                 350

Tyr Gly Pro Ala Ala Arg Leu Arg Pro Ser Asp Val Pro Asp Lys Tyr
        355                 360                 365

Tyr Ser Phe Asn Tyr Glu Gly Ile Ala Arg Asn Leu Ser Cys Arg Glu
    370                 375                 380

Pro Asn Gln His Phe Lys Pro Tyr Leu Lys His Phe Leu Pro Lys Arg
385                 390                 395                 400
```

-continued

Leu His Phe Ala Lys Ser Asp Arg Ile Glu Pro Leu Thr Phe Tyr Leu
            405                 410                 415

Asp Pro Gln Trp Gln Leu Ala Leu Asn Pro Ser Glu Arg Lys Tyr Cys
            420                 425                 430

Gly Ser Gly Phe His Gly Ser Asp Asn Val Phe Ser Asn Met Gln Ala
            435                 440                 445

Leu Phe Val Gly Tyr Gly Pro Gly Phe Lys His Gly Ile Glu Ala Asp
            450                 455                 460

Thr Phe Glu Asn Ile Glu Val Tyr Asn Leu Met Cys Asp Leu Leu Asn
465                 470                 475                 480

Leu Thr Pro Ala Pro Asn Asn Gly Thr His Gly Ser Leu Asn His Leu
            485                 490                 495

Leu Lys Asn Pro Val Tyr Thr Pro Lys His Pro Lys Glu Val His Pro
            500                 505                 510

Leu Val Gln Cys Pro Phe Thr Arg Asn Pro Arg Asp Asn Leu Gly Cys
            515                 520                 525

Ser Cys Asn Pro Ser Ile Leu Pro Ile Glu Asp Phe Gln Thr Gln Phe
            530                 535                 540

Asn Leu Thr Val Ala Glu Glu Lys Ile Ile Lys His Glu Thr Leu Pro
545                 550                 555                 560

Tyr Gly Arg Pro Arg Val Leu Gln Lys Glu Asn Thr Ile Cys Leu Leu
            565                 570                 575

Ser Gln His Gln Phe Met Ser Gly Tyr Ser Gln Asp Ile Leu Met Pro
            580                 585                 590

Leu Trp Thr Ser Tyr Thr Val Asp Arg Asn Asp Ser Phe Ser Thr Glu
            595                 600                 605

Asp Phe Ser Asn Cys Leu Tyr Gln Asp Phe Arg Ile Pro Leu Ser Pro
            610                 615                 620

Val His Lys Cys Ser Phe Tyr Lys Asn Asn Thr Lys Val Ser Tyr Gly
625                 630                 635                 640

Phe Leu Ser Pro Pro Gln Leu Asn Lys Asn Ser Ser Gly Ile Tyr Ser
            645                 650                 655

Glu Ala Leu Leu Thr Thr Asn Ile Val Pro Met Tyr Gln Ser Phe Gln
            660                 665                 670

Val Ile Trp Arg Tyr Phe His Asp Thr Leu Leu Arg Lys Tyr Ala Glu
            675                 680                 685

Glu Arg Asn Gly Val Asn Val Val Ser Gly Pro Val Phe Asp Phe Asp
            690                 695                 700

Tyr Asp Gly Arg Cys Asp Ser Leu Glu Asn Leu Arg Gln Lys Arg Arg
705                 710                 715                 720

Val Ile Arg Asn Gln Glu Ile Leu Ile Pro Thr His Phe Phe Ile Val
            725                 730                 735

Leu Thr Ser Cys Lys Asp Thr Ser Gln Thr Pro Leu His Cys Glu Asn
            740                 745                 750

Leu Asp Thr Leu Ala Phe Ile Leu Pro His Arg Thr Asp Asn Ser Glu
            755                 760                 765

Ser Cys Val His Gly Lys His Asp Ser Ser Trp Val Glu Glu Leu Leu
            770                 775                 780

Met Leu His Arg Ala Arg Ile Thr Asp Val Glu His Ile Thr Gly Leu
785                 790                 795                 800

Ser Phe Tyr Gln Gln Arg Lys Glu Pro Val Ser Asp Ile Leu Lys Leu
            805                 810                 815

```
Lys Thr His Leu Pro Thr Phe Ser Gln Glu Asp
            820                 825

<210> SEQ ID NO 3
<211> LENGTH: 1058
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Pro Ser Cys Ala Lys Glu Val Lys Ser Cys Lys Gly Arg Cys Phe Glu
1               5                   10                  15

Arg Thr Phe Gly Asn Cys Arg Cys Asp Ala Ala Cys Val Glu Leu Gly
                20                  25                  30

Asn Cys Cys Leu Asp Tyr Gln Glu Thr Cys Ile Glu Pro Glu His Ile
            35                  40                  45

Trp Thr Cys Asn Lys Phe Arg Cys Gly Glu Lys Arg Leu Thr Arg Ser
        50                  55                  60

Leu Cys Ala Cys Ser Asp Asp Cys Lys Asp Lys Gly Asp Cys Cys Ile
65                  70                  75                  80

Asn Tyr Ser Ser Val Cys Gln Gly Glu Lys Ser Trp Val Glu Glu Pro
                85                  90                  95

Cys Glu Ser Ile Asn Glu Pro Gln Cys Pro Ala Gly Phe Glu Thr Pro
            100                 105                 110

Pro Thr Leu Leu Phe Ser Leu Asp Gly Phe Arg Ala Glu Tyr Leu His
        115                 120                 125

Thr Trp Gly Gly Leu Leu Pro Val Ile Ser Lys Leu Lys Lys Cys Gly
    130                 135                 140

Thr Tyr Thr Lys Asn Met Arg Pro Val Tyr Pro Thr Lys Thr Phe Pro
145                 150                 155                 160

Asn His Tyr Ser Ile Val Thr Gly Leu Tyr Pro Glu Ser His Gly Ile
                165                 170                 175

Ile Asp Asn Lys Met Tyr Asp Pro Lys Met Asn Ala Ser Phe Ser Leu
            180                 185                 190

Lys Ser Lys Glu Lys Phe Asn Pro Glu Trp Tyr Lys Gly Glu Pro Ile
        195                 200                 205

Trp Val Thr Ala Lys Tyr Gln Gly Leu Lys Ser Gly Thr Phe Phe Trp
    210                 215                 220

Pro Gly Ser Asp Val Glu Ile Asn Gly Ile Phe Pro Asp Ile Tyr Lys
225                 230                 235                 240

Met Tyr Asn Gly Ser Val Pro Phe Glu Glu Arg Ile Leu Ala Val Leu
                245                 250                 255

Gln Trp Leu Gln Leu Pro Lys Asp Glu Arg Pro His Phe Tyr Thr Leu
            260                 265                 270

Tyr Leu Glu Glu Pro Asp Ser Ser Gly His Ser Tyr Gly Pro Val Ser
        275                 280                 285

Ser Glu Val Ile Lys Ala Leu Gln Arg Val Asp Gly Met Val Gly Met
    290                 295                 300

Leu Met Asp Gly Leu Lys Glu Leu Asn Leu His Arg Cys Leu Asn Leu
305                 310                 315                 320

Ile Leu Ile Ser Asp His Gly Met Glu Gln Gly Ser Cys Lys Lys Tyr
                325                 330                 335
```

```
Ile Tyr Leu Asn Lys Tyr Leu Gly Asp Val Lys Asn Ile Lys Val Ile
            340                 345                 350

Tyr Gly Pro Ala Ala Arg Leu Arg Pro Ser Asp Val Pro Asp Lys Tyr
            355                 360                 365

Tyr Ser Phe Asn Tyr Glu Gly Ile Ala Arg Asn Leu Ser Cys Arg Glu
        370                 375                 380

Pro Asn Gln His Phe Lys Pro Tyr Leu Lys His Phe Leu Pro Lys Arg
385                 390                 395                 400

Leu His Phe Ala Lys Ser Asp Arg Ile Glu Pro Leu Thr Phe Tyr Leu
                405                 410                 415

Asp Pro Gln Trp Gln Leu Ala Leu Asn Pro Ser Glu Lys Tyr Cys
            420                 425                 430

Gly Ser Gly Phe His Gly Ser Asp Asn Val Phe Ser Asn Met Gln Ala
            435                 440                 445

Leu Phe Val Gly Tyr Gly Pro Gly Phe Lys His Gly Ile Glu Ala Asp
        450                 455                 460

Thr Phe Glu Asn Ile Glu Val Tyr Asn Leu Met Cys Asp Leu Leu Asn
465                 470                 475                 480

Leu Thr Pro Ala Pro Asn Asn Gly Thr His Gly Ser Leu Asn His Leu
                485                 490                 495

Leu Lys Asn Pro Val Tyr Thr Pro Lys His Pro Lys Glu Val His Pro
            500                 505                 510

Leu Val Gln Cys Pro Phe Thr Arg Asn Pro Arg Asp Asn Leu Gly Cys
            515                 520                 525

Ser Cys Asn Pro Ser Ile Leu Pro Ile Glu Asp Phe Gln Thr Gln Phe
            530                 535                 540

Asn Leu Thr Val Ala Glu Glu Lys Ile Ile Lys His Glu Thr Leu Pro
545                 550                 555                 560

Tyr Gly Arg Pro Arg Val Leu Gln Lys Glu Asn Thr Ile Cys Leu Leu
                565                 570                 575

Ser Gln His Gln Phe Met Ser Gly Tyr Ser Gln Asp Ile Leu Met Pro
            580                 585                 590

Leu Trp Thr Ser Tyr Thr Val Asp Arg Asn Asp Ser Phe Ser Thr Glu
            595                 600                 605

Asp Phe Ser Asn Cys Leu Tyr Gln Asp Phe Arg Ile Pro Leu Ser Pro
        610                 615                 620

Val His Lys Cys Ser Phe Tyr Lys Asn Asn Thr Lys Val Ser Tyr Gly
625                 630                 635                 640

Phe Leu Ser Pro Pro Gln Leu Asn Lys Asn Ser Ser Gly Ile Tyr Ser
                645                 650                 655

Glu Ala Leu Leu Thr Thr Asn Ile Val Pro Met Tyr Gln Ser Phe Gln
            660                 665                 670

Val Ile Trp Arg Tyr Phe His Asp Thr Leu Leu Arg Lys Tyr Ala Glu
            675                 680                 685

Glu Arg Asn Gly Val Asn Val Val Ser Gly Pro Val Phe Asp Phe Asp
        690                 695                 700

Tyr Asp Gly Arg Cys Asp Ser Leu Glu Asn Leu Arg Gln Lys Arg Arg
705                 710                 715                 720

Val Ile Arg Asn Gln Glu Ile Leu Ile Pro Thr His Phe Phe Ile Val
                725                 730                 735

Leu Thr Ser Cys Lys Asp Thr Ser Gln Thr Pro Leu His Cys Glu Asn
            740                 745                 750
```

-continued

```
Leu Asp Thr Leu Ala Phe Ile Leu Pro His Arg Thr Asp Asn Ser Glu
            755                 760                 765

Ser Cys Val His Gly Lys His Asp Ser Ser Trp Val Glu Glu Leu Leu
770                 775                 780

Met Leu His Arg Ala Arg Ile Thr Asp Val Glu His Ile Thr Gly Leu
785                 790                 795                 800

Ser Phe Tyr Gln Gln Arg Lys Glu Pro Val Ser Asp Ile Leu Lys Leu
                805                 810                 815

Lys Thr His Leu Pro Thr Phe Ser Gln Glu Asp Pro Lys Ser Cys Asp
            820                 825                 830

Lys Thr His Thr Cys Pro Pro Cys Pro Ala Pro Glu Ala Ala Gly Ala
            835                 840                 845

Pro Ser Val Phe Leu Phe Pro Pro Lys Pro Lys Asp Thr Leu Met Ile
850                 855                 860

Ser Arg Thr Pro Glu Val Thr Cys Val Val Val Asp Val Ser His Glu
865                 870                 875                 880

Asp Pro Glu Val Lys Phe Asn Trp Tyr Val Asp Gly Val Glu Val His
                885                 890                 895

Asn Ala Lys Thr Lys Pro Arg Glu Glu Gln Tyr Asn Ser Thr Tyr Arg
            900                 905                 910

Val Val Ser Val Leu Thr Val Leu His Gln Asp Trp Leu Asn Gly Lys
            915                 920                 925

Glu Tyr Lys Cys Lys Val Ser Asn Lys Ala Leu Pro Ala Pro Ile Glu
930                 935                 940

Lys Thr Ile Ser Lys Ala Lys Gly Gln Pro Arg Glu Pro Gln Val Tyr
945                 950                 955                 960

Thr Leu Pro Pro Ser Arg Glu Glu Met Thr Lys Asn Gln Val Ser Leu
                965                 970                 975

Thr Cys Leu Val Lys Gly Phe Tyr Pro Ser Asp Ile Ala Val Glu Trp
            980                 985                 990

Glu Ser Asn Gly Gln Pro Glu Asn Asn Tyr Lys Thr Thr Pro Pro Val
            995                1000                1005

Leu Asp Ser Asp Gly Ser Phe Phe Leu Tyr Ser Lys Leu Thr Val
        1010                1015                1020

Asp Lys Ser Arg Trp Gln Gln Gly Asn Val Phe Ser Cys Ser Val
        1025                1030                1035

Met His Glu Ala Leu His Asn His Tyr Thr Gln Lys Ser Leu Ser
        1040                1045                1050

Leu Ser Pro Gly Lys
        1055

<210> SEQ ID NO 4
<211> LENGTH: 1068
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Pro Ser Cys Ala Lys Glu Val Lys Ser Cys Lys Gly Arg Cys Phe Glu
1               5                   10                  15

Arg Thr Phe Gly Asn Cys Arg Cys Asp Ala Ala Cys Val Glu Leu Gly
            20                  25                  30
```

-continued

Asn Cys Cys Leu Asp Tyr Gln Glu Thr Cys Ile Glu Pro Glu His Ile
         35                  40                  45

Trp Thr Cys Asn Lys Phe Arg Cys Gly Glu Lys Arg Leu Thr Arg Ser
     50                  55                  60

Leu Cys Ala Cys Ser Asp Asp Cys Lys Asp Lys Gly Asp Cys Cys Ile
 65                  70                  75                  80

Asn Tyr Ser Ser Val Cys Gln Gly Glu Lys Ser Trp Val Glu Pro
                 85                  90                  95

Cys Glu Ser Ile Asn Glu Pro Gln Cys Pro Ala Gly Phe Glu Thr Pro
                100                 105                 110

Pro Thr Leu Leu Phe Ser Leu Asp Gly Phe Arg Ala Glu Tyr Leu His
                115                 120                 125

Thr Trp Gly Gly Leu Leu Pro Val Ile Ser Lys Leu Lys Lys Cys Gly
         130                 135                 140

Thr Tyr Thr Lys Asn Met Arg Pro Val Tyr Pro Thr Lys Thr Phe Pro
145                 150                 155                 160

Asn His Tyr Ser Ile Val Thr Gly Leu Tyr Pro Glu Ser His Gly Ile
                 165                 170                 175

Ile Asp Asn Lys Met Tyr Asp Pro Lys Met Asn Ala Ser Phe Ser Leu
         180                 185                 190

Lys Ser Lys Glu Lys Phe Asn Pro Glu Trp Tyr Lys Gly Glu Pro Ile
         195                 200                 205

Trp Val Thr Ala Lys Tyr Gln Gly Leu Lys Ser Gly Thr Phe Phe Trp
     210                 215                 220

Pro Gly Ser Asp Val Glu Ile Asn Gly Ile Phe Pro Asp Ile Tyr Lys
225                 230                 235                 240

Met Tyr Asn Gly Ser Val Pro Phe Glu Glu Arg Ile Leu Ala Val Leu
                 245                 250                 255

Gln Trp Leu Gln Leu Pro Lys Asp Glu Arg Pro His Phe Tyr Thr Leu
         260                 265                 270

Tyr Leu Glu Glu Pro Asp Ser Ser Gly His Ser Tyr Gly Pro Val Ser
     275                 280                 285

Ser Glu Val Ile Lys Ala Leu Gln Arg Val Asp Gly Met Val Gly Met
290                 295                 300

Leu Met Asp Gly Leu Lys Glu Leu Asn Leu His Arg Cys Leu Asn Leu
305                 310                 315                 320

Ile Leu Ile Ser Asp His Gly Met Glu Gln Gly Ser Cys Lys Lys Tyr
                 325                 330                 335

Ile Tyr Leu Asn Lys Tyr Leu Gly Asp Val Lys Asn Ile Lys Val Ile
             340                 345                 350

Tyr Gly Pro Ala Ala Arg Leu Arg Pro Ser Asp Val Pro Asp Lys Tyr
         355                 360                 365

Tyr Ser Phe Asn Tyr Glu Gly Ile Ala Arg Asn Leu Ser Cys Arg Glu
     370                 375                 380

Pro Asn Gln His Phe Lys Pro Tyr Leu Lys His Phe Leu Pro Lys Arg
385                 390                 395                 400

Leu His Phe Ala Lys Ser Asp Arg Ile Glu Pro Leu Thr Phe Tyr Leu
                 405                 410                 415

Asp Pro Gln Trp Gln Leu Ala Leu Asn Pro Ser Glu Arg Lys Tyr Cys
             420                 425                 430

Gly Ser Gly Phe His Gly Ser Asp Asn Val Phe Ser Asn Met Gln Ala
         435                 440                 445

-continued

```
Leu Phe Val Gly Tyr Gly Pro Gly Phe Lys His Gly Ile Glu Ala Asp
    450                 455                 460

Thr Phe Glu Asn Ile Glu Val Tyr Asn Leu Met Cys Asp Leu Leu Asn
465                 470                 475                 480

Leu Thr Pro Ala Pro Asn Asn Gly Thr His Gly Ser Leu Asn His Leu
                485                 490                 495

Leu Lys Asn Pro Val Tyr Thr Pro Lys His Pro Lys Glu Val His Pro
                500                 505                 510

Leu Val Gln Cys Pro Phe Thr Arg Asn Pro Arg Asp Asn Leu Gly Cys
                515                 520                 525

Ser Cys Asn Pro Ser Ile Leu Pro Ile Glu Asp Phe Gln Thr Gln Phe
530                 535                 540

Asn Leu Thr Val Ala Glu Glu Lys Ile Ile Lys His Glu Thr Leu Pro
545                 550                 555                 560

Tyr Gly Arg Pro Arg Val Leu Gln Lys Glu Asn Thr Ile Cys Leu Leu
                565                 570                 575

Ser Gln His Gln Phe Met Ser Gly Tyr Ser Gln Asp Ile Leu Met Pro
                580                 585                 590

Leu Trp Thr Ser Tyr Thr Val Asp Arg Asn Asp Ser Phe Ser Thr Glu
                595                 600                 605

Asp Phe Ser Asn Cys Leu Tyr Gln Asp Phe Arg Ile Pro Leu Ser Pro
610                 615                 620

Val His Lys Cys Ser Phe Tyr Lys Asn Asn Thr Lys Val Ser Tyr Gly
625                 630                 635                 640

Phe Leu Ser Pro Pro Gln Leu Asn Lys Asn Ser Ser Gly Ile Tyr Ser
                645                 650                 655

Glu Ala Leu Leu Thr Thr Asn Ile Val Pro Met Tyr Gln Ser Phe Gln
                660                 665                 670

Val Ile Trp Arg Tyr Phe His Asp Thr Leu Leu Arg Lys Tyr Ala Glu
                675                 680                 685

Glu Arg Asn Gly Val Asn Val Val Ser Gly Pro Val Phe Asp Phe Asp
690                 695                 700

Tyr Asp Gly Arg Cys Asp Ser Leu Glu Asn Leu Arg Gln Lys Arg Arg
705                 710                 715                 720

Val Ile Arg Asn Gln Glu Ile Leu Ile Pro Thr His Phe Phe Ile Val
                725                 730                 735

Leu Thr Ser Cys Lys Asp Thr Ser Gln Thr Pro Leu His Cys Glu Asn
                740                 745                 750

Leu Asp Thr Leu Ala Phe Ile Leu Pro His Arg Thr Asp Asn Ser Glu
                755                 760                 765

Ser Cys Val His Gly Lys His Asp Ser Ser Trp Val Glu Glu Leu Leu
                770                 775                 780

Met Leu His Arg Ala Arg Ile Thr Asp Val Glu His Ile Thr Gly Leu
785                 790                 795                 800

Ser Phe Tyr Gln Gln Arg Lys Glu Pro Val Ser Asp Ile Leu Lys Leu
                805                 810                 815

Lys Thr His Leu Pro Thr Phe Ser Gln Glu Asp Pro Ser Cys Asp
                820                 825                 830

Lys Thr His Thr Cys Pro Pro Cys Pro Ala Pro Glu Ala Ala Gly Ala
                835                 840                 845

Pro Ser Val Phe Leu Phe Pro Pro Lys Pro Lys Asp Thr Leu Met Ile
850                 855                 860
```

Ser Arg Thr Pro Glu Val Thr Cys Val Val Asp Val Ser His Glu
865                 870                 875                 880

Asp Pro Glu Val Lys Phe Asn Trp Tyr Val Asp Gly Val Glu Val His
            885                 890                 895

Asn Ala Lys Thr Lys Pro Arg Glu Glu Gln Tyr Asn Ser Thr Tyr Arg
        900                 905                 910

Val Val Ser Val Leu Thr Val Leu His Gln Asp Trp Leu Asn Gly Lys
        915                 920                 925

Glu Tyr Lys Cys Lys Val Ser Asn Lys Ala Leu Pro Ala Pro Ile Glu
    930                 935                 940

Lys Thr Ile Ser Lys Ala Lys Gly Gln Pro Arg Glu Pro Gln Val Tyr
945                 950                 955                 960

Thr Leu Pro Pro Ser Arg Glu Glu Met Thr Lys Asn Gln Val Ser Leu
                965                 970                 975

Thr Cys Leu Val Lys Gly Phe Tyr Pro Ser Asp Ile Ala Val Glu Trp
            980                 985                 990

Glu Ser Asn Gly Gln Pro Glu Asn Asn Tyr Lys Thr Thr Pro Pro Val
        995                 1000                1005

Leu Asp Ser Asp Gly Ser Phe Phe Leu Tyr Ser Lys Leu Thr Val
    1010                1015                1020

Asp Lys Ser Arg Trp Gln Gln Gly Asn Val Phe Ser Cys Ser Val
    1025                1030                1035

Met His Glu Ala Leu His Asn His Tyr Thr Gln Lys Ser Leu Ser
    1040                1045                1050

Leu Ser Pro Gly Lys Asp Asp Asp Asp Asp Asp Asp Asp Asp
    1055                1060                1065

<210> SEQ ID NO 5
<211> LENGTH: 819
<212> TYPE: PRT
<213> ORGANISM: Homo sapiens

<400> SEQUENCE: 5

Ser Cys Lys Gly Arg Cys Phe Glu Arg Thr Phe Gly Asn Cys Arg Cys
1               5                   10                  15

Asp Ala Ala Cys Val Glu Leu Gly Asn Cys Cys Leu Asp Tyr Gln Glu
            20                  25                  30

Thr Cys Ile Glu Pro Glu His Ile Trp Thr Cys Asn Lys Phe Arg Cys
        35                  40                  45

Gly Glu Lys Arg Leu Thr Arg Ser Leu Cys Ala Cys Ser Asp Asp Cys
50                  55                  60

Lys Asp Lys Gly Asp Cys Cys Ile Asn Tyr Ser Ser Val Cys Gln Gly
65                  70                  75                  80

Glu Lys Ser Trp Val Glu Glu Pro Cys Glu Ser Ile Asn Glu Pro Gln
                85                  90                  95

Cys Pro Ala Gly Phe Glu Thr Pro Thr Leu Leu Phe Ser Leu Asp
            100                 105                 110

Gly Phe Arg Ala Glu Tyr Leu His Thr Trp Gly Gly Leu Leu Pro Val
        115                 120                 125

Ile Ser Lys Leu Lys Lys Cys Gly Thr Tyr Thr Lys Asn Met Arg Pro
130                 135                 140

Val Tyr Pro Thr Lys Thr Phe Pro Asn His Tyr Ser Ile Val Thr Gly
145                 150                 155                 160

```
Leu Tyr Pro Glu Ser His Gly Ile Ile Asp Asn Lys Met Tyr Asp Pro
                165                 170                 175

Lys Met Asn Ala Ser Phe Ser Leu Lys Ser Lys Glu Lys Phe Asn Pro
            180                 185                 190

Glu Trp Tyr Lys Gly Glu Pro Ile Trp Val Thr Ala Lys Tyr Gln Gly
        195                 200                 205

Leu Lys Ser Gly Thr Phe Phe Trp Pro Gly Ser Asp Val Glu Ile Asn
    210                 215                 220

Gly Ile Phe Pro Asp Ile Tyr Lys Met Tyr Asn Gly Ser Val Pro Phe
225                 230                 235                 240

Glu Glu Arg Ile Leu Ala Val Leu Gln Trp Leu Gln Leu Pro Lys Asp
                245                 250                 255

Glu Arg Pro His Phe Tyr Thr Leu Tyr Leu Glu Glu Pro Asp Ser Ser
            260                 265                 270

Gly His Ser Tyr Gly Pro Val Ser Ser Glu Val Ile Lys Ala Leu Gln
        275                 280                 285

Arg Val Asp Gly Met Val Gly Met Leu Met Asp Gly Leu Lys Glu Leu
    290                 295                 300

Asn Leu His Arg Cys Leu Asn Leu Ile Leu Ile Ser Asp His Gly Met
305                 310                 315                 320

Glu Gln Gly Ser Cys Lys Lys Tyr Ile Tyr Leu Asn Lys Tyr Leu Gly
                325                 330                 335

Asp Val Lys Asn Ile Lys Val Ile Tyr Gly Pro Ala Ala Arg Leu Arg
            340                 345                 350

Pro Ser Asp Val Pro Asp Lys Tyr Tyr Ser Phe Asn Tyr Glu Gly Ile
        355                 360                 365

Ala Arg Asn Leu Ser Cys Arg Glu Pro Asn Gln His Phe Lys Pro Tyr
    370                 375                 380

Leu Lys His Phe Leu Pro Lys Arg Leu His Phe Ala Lys Ser Asp Arg
385                 390                 395                 400

Ile Glu Pro Leu Thr Phe Tyr Leu Asp Pro Gln Trp Gln Leu Ala Leu
                405                 410                 415

Asn Pro Ser Glu Arg Lys Tyr Cys Gly Ser Gly Phe His Gly Ser Asp
            420                 425                 430

Asn Val Phe Ser Asn Met Gln Ala Leu Phe Val Gly Tyr Gly Pro Gly
        435                 440                 445

Phe Lys His Gly Ile Glu Ala Asp Thr Phe Glu Asn Ile Glu Val Tyr
    450                 455                 460

Asn Leu Met Cys Asp Leu Leu Asn Leu Thr Pro Ala Pro Asn Asn Gly
465                 470                 475                 480

Thr His Gly Ser Leu Asn His Leu Leu Lys Asn Pro Val Tyr Thr Pro
                485                 490                 495

Lys His Pro Lys Glu Val His Pro Leu Val Gln Cys Pro Phe Thr Arg
            500                 505                 510

Asn Pro Arg Asp Asn Leu Gly Cys Ser Cys Asn Pro Ser Ile Leu Pro
        515                 520                 525

Ile Glu Asp Phe Gln Thr Gln Phe Asn Leu Thr Val Ala Glu Glu Lys
    530                 535                 540

Ile Ile Lys His Glu Thr Leu Pro Tyr Gly Arg Pro Arg Val Leu Gln
545                 550                 555                 560

Lys Glu Asn Thr Ile Cys Leu Leu Ser Gln His Gln Phe Met Ser Gly
                565                 570                 575
```

```
Tyr Ser Gln Asp Ile Leu Met Pro Leu Trp Thr Ser Tyr Thr Val Asp
                580                 585                 590

Arg Asn Asp Ser Phe Ser Thr Glu Asp Phe Ser Asn Cys Leu Tyr Gln
            595                 600                 605

Asp Phe Arg Ile Pro Leu Ser Pro Val His Lys Cys Ser Phe Tyr Lys
        610                 615                 620

Asn Asn Thr Lys Val Ser Tyr Gly Phe Leu Ser Pro Gln Leu Asn
625                 630                 635                 640

Lys Asn Ser Ser Gly Ile Tyr Ser Glu Ala Leu Leu Thr Thr Asn Ile
                645                 650                 655

Val Pro Met Tyr Gln Ser Phe Gln Val Ile Trp Arg Tyr Phe His Asp
            660                 665                 670

Thr Leu Leu Arg Lys Tyr Ala Glu Glu Arg Asn Gly Val Asn Val Val
        675                 680                 685

Ser Gly Pro Val Phe Asp Phe Asp Tyr Asp Gly Arg Cys Asp Ser Leu
    690                 695                 700

Glu Asn Leu Arg Gln Lys Arg Val Ile Arg Asn Gln Glu Ile Leu
705                 710                 715                 720

Ile Pro Thr His Phe Phe Ile Val Leu Thr Ser Cys Lys Asp Thr Ser
                725                 730                 735

Gln Thr Pro Leu His Cys Glu Asn Leu Asp Thr Leu Ala Phe Ile Leu
            740                 745                 750

Pro His Arg Thr Asp Asn Ser Glu Ser Cys Val His Gly Lys His Asp
        755                 760                 765

Ser Ser Trp Val Glu Leu Leu Met Leu Arg Ala Arg Ile Thr
    770                 775                 780

Asp Val Glu His Ile Thr Gly Leu Ser Phe Tyr Gln Gln Arg Lys Glu
785                 790                 795                 800

Pro Val Ser Asp Ile Leu Lys Leu Lys Thr His Leu Pro Thr Phe Ser
                805                 810                 815

Gln Glu Asp

<210> SEQ ID NO 6
<211> LENGTH: 739
<212> TYPE: PRT
<213> ORGANISM: Homo sapiens

<400> SEQUENCE: 6

Glu Lys Ser Trp Val Glu Pro Cys Glu Ser Ile Asn Glu Pro Gln
1               5                   10                  15

Cys Pro Ala Gly Phe Glu Thr Pro Thr Leu Leu Phe Ser Leu Asp
            20                  25                  30

Gly Phe Arg Ala Glu Tyr Leu His Thr Trp Gly Gly Leu Leu Pro Val
        35                  40                  45

Ile Ser Lys Leu Lys Lys Cys Gly Thr Tyr Thr Lys Asn Met Arg Pro
50                  55                  60

Val Tyr Pro Thr Lys Thr Phe Pro Asn His Tyr Ser Ile Val Thr Gly
65                  70                  75                  80

Leu Tyr Pro Glu Ser His Gly Ile Ile Asp Asn Lys Met Tyr Asp Pro
            85                  90                  95

Lys Met Asn Ala Ser Phe Ser Leu Lys Ser Lys Glu Lys Phe Asn Pro
        100                 105                 110

Glu Trp Tyr Lys Gly Glu Pro Ile Trp Val Thr Ala Lys Tyr Gln Gly
    115                 120                 125
```

-continued

```
Leu Lys Ser Gly Thr Phe Phe Trp Pro Gly Ser Asp Val Glu Ile Asn
    130                 135                 140
Gly Ile Phe Pro Asp Ile Tyr Lys Met Tyr Asn Gly Ser Val Pro Phe
145                 150                 155                 160
Glu Glu Arg Ile Leu Ala Val Leu Gln Trp Leu Gln Leu Pro Lys Asp
                165                 170                 175
Glu Arg Pro His Phe Tyr Thr Leu Tyr Leu Glu Glu Pro Asp Ser Ser
            180                 185                 190
Gly His Ser Tyr Gly Pro Val Ser Ser Glu Val Ile Lys Ala Leu Gln
        195                 200                 205
Arg Val Asp Gly Met Val Gly Met Leu Met Asp Gly Leu Lys Glu Leu
    210                 215                 220
Asn Leu His Arg Cys Leu Asn Leu Ile Leu Ile Ser Asp His Gly Met
225                 230                 235                 240
Glu Gln Gly Ser Cys Lys Lys Tyr Ile Tyr Leu Asn Lys Tyr Leu Gly
                245                 250                 255
Asp Val Lys Asn Ile Lys Val Ile Tyr Gly Pro Ala Ala Arg Leu Arg
            260                 265                 270
Pro Ser Asp Val Pro Asp Lys Tyr Tyr Ser Phe Asn Tyr Glu Gly Ile
        275                 280                 285
Ala Arg Asn Leu Ser Cys Arg Glu Pro Asn Gln His Phe Lys Pro Tyr
    290                 295                 300
Leu Lys His Phe Leu Pro Lys Arg Leu His Phe Ala Lys Ser Asp Arg
305                 310                 315                 320
Ile Glu Pro Leu Thr Phe Tyr Leu Asp Pro Gln Trp Gln Leu Ala Leu
                325                 330                 335
Asn Pro Ser Glu Arg Lys Tyr Cys Gly Ser Gly Phe His Gly Ser Asp
            340                 345                 350
Asn Val Phe Ser Asn Met Gln Ala Leu Phe Val Gly Tyr Gly Pro Gly
        355                 360                 365
Phe Lys His Gly Ile Glu Ala Asp Thr Phe Glu Asn Ile Glu Val Tyr
    370                 375                 380
Asn Leu Met Cys Asp Leu Leu Asn Leu Thr Pro Ala Pro Asn Asn Gly
385                 390                 395                 400
Thr His Gly Ser Leu Asn His Leu Leu Lys Asn Pro Val Tyr Thr Pro
                405                 410                 415
Lys His Pro Lys Glu Val His Pro Leu Val Gln Cys Pro Phe Thr Arg
            420                 425                 430
Asn Pro Arg Asp Asn Leu Gly Cys Ser Cys Asn Pro Ser Ile Leu Pro
        435                 440                 445
Ile Glu Asp Phe Gln Thr Gln Phe Asn Leu Thr Val Ala Glu Glu Lys
    450                 455                 460
Ile Ile Lys His Glu Thr Leu Pro Tyr Gly Arg Pro Arg Val Leu Gln
465                 470                 475                 480
Lys Glu Asn Thr Ile Cys Leu Leu Ser Gln His Gln Phe Met Ser Gly
                485                 490                 495
Tyr Ser Gln Asp Ile Leu Met Pro Leu Trp Thr Ser Tyr Thr Val Asp
            500                 505                 510
Arg Asn Asp Ser Phe Ser Thr Glu Asp Phe Ser Asn Cys Leu Tyr Gln
        515                 520                 525
Asp Phe Arg Ile Pro Leu Ser Pro Val His Lys Cys Ser Phe Tyr Lys
    530                 535                 540
```

-continued

```
Asn Asn Thr Lys Val Ser Tyr Gly Phe Leu Ser Pro Gln Leu Asn
545                 550                 555                 560

Lys Asn Ser Ser Gly Ile Tyr Ser Glu Ala Leu Leu Thr Asn Ile
            565                 570                 575

Val Pro Met Tyr Gln Ser Phe Gln Val Ile Trp Arg Tyr Phe His Asp
        580                 585                 590

Thr Leu Leu Arg Lys Tyr Ala Glu Glu Arg Asn Gly Val Asn Val Val
            595                 600                 605

Ser Gly Pro Val Phe Asp Phe Asp Tyr Asp Gly Arg Cys Asp Ser Leu
    610                 615                 620

Glu Asn Leu Arg Gln Lys Arg Val Ile Arg Asn Gln Glu Ile Leu
625                 630                 635                 640

Ile Pro Thr His Phe Phe Ile Val Leu Thr Ser Cys Lys Asp Thr Ser
                645                 650                 655

Gln Thr Pro Leu His Cys Glu Asn Leu Asp Thr Leu Ala Phe Ile Leu
            660                 665                 670

Pro His Arg Thr Asp Asn Ser Glu Ser Cys Val His Gly Lys His Asp
        675                 680                 685

Ser Ser Trp Val Glu Glu Leu Leu Met Leu His Arg Ala Arg Ile Thr
    690                 695                 700

Asp Val Glu His Ile Thr Gly Leu Ser Phe Tyr Gln Gln Arg Lys Glu
705                 710                 715                 720

Pro Val Ser Asp Ile Leu Lys Leu Lys Thr His Leu Pro Thr Phe Ser
                725                 730                 735

Gln Glu Asp

<210> SEQ ID NO 7
<211> LENGTH: 232
<212> TYPE: PRT
<213> ORGANISM: Homo sapiens

<400> SEQUENCE: 7

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175
```

```
Lys Thr Thr Pro Pro Val Leu Asp Ser Asp Gly Ser Phe Phe Leu Tyr
                180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 8
<211> LENGTH: 227
<212> TYPE: PRT
<213> ORGANISM: Homo sapiens

<400> SEQUENCE: 8

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 9
<211> LENGTH: 1051
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 9

```
Ser Cys Lys Gly Arg Cys Phe Glu Arg Thr Phe Gly Asn Cys Arg Cys
1               5                   10                  15

Asp Ala Ala Cys Val Glu Leu Gly Asn Cys Cys Leu Asp Tyr Gln Glu
            20                  25                  30

Thr Cys Ile Glu Pro Glu His Ile Trp Thr Cys Asn Lys Phe Arg Cys
        35                  40                  45

Gly Glu Lys Arg Leu Thr Arg Ser Leu Cys Ala Cys Ser Asp Asp Cys
    50                  55                  60

Lys Asp Lys Gly Asp Cys Cys Ile Asn Tyr Ser Ser Val Cys Gln Gly
65                  70                  75                  80

Glu Lys Ser Trp Val Glu Glu Pro Cys Glu Ser Ile Asn Glu Pro Gln
                85                  90                  95

Cys Pro Ala Gly Phe Glu Thr Pro Pro Thr Leu Leu Phe Ser Leu Asp
            100                 105                 110

Gly Phe Arg Ala Glu Tyr Leu His Thr Trp Gly Gly Leu Leu Pro Val
        115                 120                 125

Ile Ser Lys Leu Lys Lys Cys Gly Thr Tyr Thr Lys Asn Met Arg Pro
    130                 135                 140

Val Tyr Pro Thr Lys Thr Phe Pro Asn His Tyr Ser Ile Val Thr Gly
145                 150                 155                 160

Leu Tyr Pro Glu Ser His Gly Ile Ile Asp Asn Lys Met Tyr Asp Pro
                165                 170                 175

Lys Met Asn Ala Ser Phe Ser Leu Lys Ser Lys Glu Lys Phe Asn Pro
            180                 185                 190

Glu Trp Tyr Lys Gly Glu Pro Ile Trp Val Thr Ala Lys Tyr Gln Gly
        195                 200                 205

Leu Lys Ser Gly Thr Phe Phe Trp Pro Gly Ser Asp Val Glu Ile Asn
    210                 215                 220

Gly Ile Phe Pro Asp Ile Tyr Lys Met Tyr Asn Gly Ser Val Pro Phe
225                 230                 235                 240

Glu Glu Arg Ile Leu Ala Val Leu Gln Trp Leu Gln Leu Pro Lys Asp
                245                 250                 255

Glu Arg Pro His Phe Tyr Thr Leu Tyr Leu Glu Glu Pro Asp Ser Ser
            260                 265                 270

Gly His Ser Tyr Gly Pro Val Ser Ser Glu Val Ile Lys Ala Leu Gln
        275                 280                 285

Arg Val Asp Gly Met Val Gly Met Leu Met Asp Gly Leu Lys Glu Leu
    290                 295                 300

Asn Leu His Arg Cys Leu Asn Leu Ile Leu Ile Ser Asp His Gly Met
305                 310                 315                 320

Glu Gln Gly Ser Cys Lys Lys Tyr Ile Tyr Leu Asn Lys Tyr Leu Gly
                325                 330                 335

Asp Val Lys Asn Ile Lys Val Ile Tyr Gly Pro Ala Ala Arg Leu Arg
            340                 345                 350

Pro Ser Asp Val Pro Asp Lys Tyr Tyr Ser Phe Asn Tyr Glu Gly Ile
        355                 360                 365

Ala Arg Asn Leu Ser Cys Arg Glu Pro Asn Gln His Phe Lys Pro Tyr
    370                 375                 380

Leu Lys His Phe Leu Pro Lys Arg Leu His Phe Ala Lys Ser Asp Arg
385                 390                 395                 400
```

```
Ile Glu Pro Leu Thr Phe Tyr Leu Asp Pro Gln Trp Gln Leu Ala Leu
                405                 410                 415

Asn Pro Ser Glu Arg Lys Tyr Cys Gly Ser Gly Phe His Gly Ser Asp
            420                 425                 430

Asn Val Phe Ser Asn Met Gln Ala Leu Phe Val Gly Tyr Gly Pro Gly
        435                 440                 445

Phe Lys His Gly Ile Glu Ala Asp Thr Phe Glu Asn Ile Glu Val Tyr
    450                 455                 460

Asn Leu Met Cys Asp Leu Leu Asn Leu Thr Pro Ala Pro Asn Asn Gly
465                 470                 475                 480

Thr His Gly Ser Leu Asn His Leu Leu Lys Asn Pro Val Tyr Thr Pro
                485                 490                 495

Lys His Pro Lys Glu Val His Pro Leu Val Gln Cys Pro Phe Thr Arg
            500                 505                 510

Asn Pro Arg Asp Asn Leu Gly Cys Ser Cys Asn Pro Ser Ile Leu Pro
        515                 520                 525

Ile Glu Asp Phe Gln Thr Gln Phe Asn Leu Thr Val Ala Glu Glu Lys
    530                 535                 540

Ile Ile Lys His Glu Thr Leu Pro Tyr Gly Arg Pro Arg Val Leu Gln
545                 550                 555                 560

Lys Glu Asn Thr Ile Cys Leu Leu Ser Gln His Gln Phe Met Ser Gly
                565                 570                 575

Tyr Ser Gln Asp Ile Leu Met Pro Leu Trp Thr Ser Tyr Thr Val Asp
            580                 585                 590

Arg Asn Asp Ser Phe Ser Thr Glu Asp Phe Ser Asn Cys Leu Tyr Gln
        595                 600                 605

Asp Phe Arg Ile Pro Leu Ser Pro Val His Lys Cys Ser Phe Tyr Lys
    610                 615                 620

Asn Asn Thr Lys Val Ser Tyr Gly Phe Leu Ser Pro Pro Gln Leu Asn
625                 630                 635                 640

Lys Asn Ser Ser Gly Ile Tyr Ser Glu Ala Leu Leu Thr Thr Asn Ile
                645                 650                 655

Val Pro Met Tyr Gln Ser Phe Gln Val Ile Trp Arg Tyr Phe His Asp
            660                 665                 670

Thr Leu Leu Arg Lys Tyr Ala Glu Glu Arg Asn Gly Val Asn Val Val
        675                 680                 685

Ser Gly Pro Val Phe Asp Phe Asp Tyr Asp Gly Arg Cys Asp Ser Leu
    690                 695                 700

Glu Asn Leu Arg Gln Lys Arg Arg Val Ile Arg Asn Gln Glu Ile Leu
705                 710                 715                 720

Ile Pro Thr His Phe Phe Ile Val Leu Thr Ser Cys Lys Asp Thr Ser
                725                 730                 735

Gln Thr Pro Leu His Cys Glu Asn Leu Asp Thr Leu Ala Phe Ile Leu
            740                 745                 750

Pro His Arg Thr Asp Asn Ser Glu Ser Cys Val His Gly Lys His Asp
        755                 760                 765

Ser Ser Trp Val Glu Glu Leu Leu Met Leu His Arg Ala Arg Ile Thr
    770                 775                 780

Asp Val Glu His Ile Thr Gly Leu Ser Phe Tyr Gln Gln Arg Lys Glu
785                 790                 795                 800

Pro Val Ser Asp Ile Leu Lys Leu Lys Thr His Leu Pro Thr Phe Ser
                805                 810                 815
```

```
Gln Glu Asp Glu Pro Lys Ser Cys Asp Lys Thr His Thr Cys Pro Pro
                820                 825                 830

Cys Pro Ala Pro Glu Leu Leu Gly Gly Pro Ser Val Phe Leu Phe Pro
            835                 840                 845

Pro Lys Pro Lys Asp Thr Leu Met Ile Ser Arg Thr Pro Glu Val Thr
    850                 855                 860

Cys Val Val Val Asp Val Ser His Glu Asp Pro Glu Val Lys Phe Asn
865                 870                 875                 880

Trp Tyr Val Asp Gly Val Glu Val His Asn Ala Lys Thr Lys Pro Arg
                885                 890                 895

Glu Glu Gln Tyr Asn Ser Thr Tyr Arg Val Val Ser Val Leu Thr Val
                900                 905                 910

Leu His Gln Asp Trp Leu Asn Gly Lys Glu Tyr Lys Cys Lys Val Ser
                915                 920                 925

Asn Lys Ala Leu Pro Ala Pro Ile Glu Lys Thr Ile Ser Lys Ala Lys
            930                 935                 940

Gly Gln Pro Arg Glu Pro Gln Val Tyr Thr Leu Pro Pro Ser Arg Glu
945                 950                 955                 960

Glu Met Thr Lys Asn Gln Val Ser Leu Thr Cys Leu Val Lys Gly Phe
                965                 970                 975

Tyr Pro Ser Asp Ile Ala Val Glu Trp Glu Ser Asn Gly Gln Pro Glu
                980                 985                 990

Asn Asn Tyr Lys Thr Thr Pro Pro  Val Leu Asp Ser Asp  Gly Ser Phe
                995                 1000                1005

Phe Leu  Tyr Ser Lys Leu Thr  Val Asp Lys Ser Arg  Trp Gln Gln
    1010                1015                1020

Gly Asn  Val Phe Ser Cys Ser  Val Met His Glu Ala  Leu His Asn
    1025                1030                1035

His Tyr  Thr Gln Lys Ser Leu  Ser Leu Ser Pro Gly  Lys
    1040                1045                1050

<210> SEQ ID NO 10
<211> LENGTH: 1046
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Ser Cys Lys Gly Arg Cys Phe Glu Arg Thr Phe Gly Asn Cys Arg Cys
1               5                   10                  15

Asp Ala Ala Cys Val Glu Leu Gly Asn Cys Cys Leu Asp Tyr Gln Glu
                20                  25                  30

Thr Cys Ile Glu Pro Glu His Ile Trp Thr Cys Asn Lys Phe Arg Cys
            35                  40                  45

Gly Glu Lys Arg Leu Thr Arg Ser Leu Cys Ala Cys Ser Asp Asp Cys
        50                  55                  60

Lys Asp Lys Gly Asp Cys Cys Ile Asn Tyr Ser Ser Val Cys Gln Gly
65                  70                  75                  80

Glu Lys Ser Trp Val Glu Glu Pro Cys Glu Ser Ile Asn Glu Pro Gln
                85                  90                  95

Cys Pro Ala Gly Phe Glu Thr Pro Pro Thr Leu Leu Phe Ser Leu Asp
                100                 105                 110
```

```
Gly Phe Arg Ala Glu Tyr Leu His Thr Trp Gly Gly Leu Leu Pro Val
            115                 120                 125

Ile Ser Lys Leu Lys Lys Cys Gly Thr Tyr Thr Lys Asn Met Arg Pro
        130                 135                 140

Val Tyr Pro Thr Lys Thr Phe Pro Asn His Tyr Ser Ile Val Thr Gly
145                 150                 155                 160

Leu Tyr Pro Glu Ser His Gly Ile Ile Asp Asn Lys Met Tyr Asp Pro
                165                 170                 175

Lys Met Asn Ala Ser Phe Ser Leu Lys Ser Lys Glu Lys Phe Asn Pro
            180                 185                 190

Glu Trp Tyr Lys Gly Glu Pro Ile Trp Val Thr Ala Lys Tyr Gln Gly
        195                 200                 205

Leu Lys Ser Gly Thr Phe Phe Trp Pro Gly Ser Asp Val Glu Ile Asn
        210                 215                 220

Gly Ile Phe Pro Asp Ile Tyr Lys Met Tyr Asn Gly Ser Val Pro Phe
225                 230                 235                 240

Glu Glu Arg Ile Leu Ala Val Leu Gln Trp Leu Gln Leu Pro Lys Asp
                245                 250                 255

Glu Arg Pro His Phe Tyr Thr Leu Tyr Leu Glu Glu Pro Asp Ser Ser
            260                 265                 270

Gly His Ser Tyr Gly Pro Val Ser Ser Glu Val Ile Lys Ala Leu Gln
        275                 280                 285

Arg Val Asp Gly Met Val Gly Met Leu Met Asp Gly Leu Lys Glu Leu
        290                 295                 300

Asn Leu His Arg Cys Leu Asn Leu Ile Leu Ile Ser Asp His Gly Met
305                 310                 315                 320

Glu Gln Gly Ser Cys Lys Lys Tyr Ile Tyr Leu Asn Lys Tyr Leu Gly
                325                 330                 335

Asp Val Lys Asn Ile Lys Val Ile Tyr Gly Pro Ala Ala Arg Leu Arg
            340                 345                 350

Pro Ser Asp Val Pro Asp Lys Tyr Tyr Ser Phe Asn Tyr Glu Gly Ile
        355                 360                 365

Ala Arg Asn Leu Ser Cys Arg Glu Pro Asn Gln His Phe Lys Pro Tyr
        370                 375                 380

Leu Lys His Phe Leu Pro Lys Arg Leu His Phe Ala Lys Ser Asp Arg
385                 390                 395                 400

Ile Glu Pro Leu Thr Phe Tyr Leu Asp Pro Gln Trp Gln Leu Ala Leu
                405                 410                 415

Asn Pro Ser Glu Arg Lys Tyr Cys Gly Ser Gly Phe His Gly Ser Asp
            420                 425                 430

Asn Val Phe Ser Asn Met Gln Ala Leu Phe Val Gly Tyr Gly Pro Gly
        435                 440                 445

Phe Lys His Gly Ile Glu Ala Asp Thr Phe Glu Asn Ile Glu Val Tyr
        450                 455                 460

Asn Leu Met Cys Asp Leu Leu Asn Leu Thr Pro Ala Pro Asn Asn Gly
465                 470                 475                 480

Thr His Gly Ser Leu Asn His Leu Leu Lys Asn Pro Val Tyr Thr Pro
                485                 490                 495

Lys His Pro Lys Glu Val His Pro Leu Val Gln Cys Pro Phe Thr Arg
            500                 505                 510

Asn Pro Arg Asp Asn Leu Gly Cys Ser Cys Asn Pro Ser Ile Leu Pro
        515                 520                 525
```

```
Ile Glu Asp Phe Gln Thr Gln Phe Asn Leu Thr Val Ala Glu Glu Lys
530                 535                 540

Ile Ile Lys His Glu Thr Leu Pro Tyr Gly Arg Pro Arg Val Leu Gln
545                 550                 555                 560

Lys Glu Asn Thr Ile Cys Leu Leu Ser Gln His Gln Phe Met Ser Gly
                565                 570                 575

Tyr Ser Gln Asp Ile Leu Met Pro Leu Trp Thr Ser Tyr Thr Val Asp
                580                 585                 590

Arg Asn Asp Ser Phe Ser Thr Glu Asp Phe Ser Asn Cys Leu Tyr Gln
                595                 600                 605

Asp Phe Arg Ile Pro Leu Ser Pro Val His Lys Cys Ser Phe Tyr Lys
610                 615                 620

Asn Asn Thr Lys Val Ser Tyr Gly Phe Leu Ser Pro Pro Gln Leu Asn
625                 630                 635                 640

Lys Asn Ser Ser Gly Ile Tyr Ser Glu Ala Leu Leu Thr Thr Asn Ile
                645                 650                 655

Val Pro Met Tyr Gln Ser Phe Gln Val Ile Trp Arg Tyr Phe His Asp
                660                 665                 670

Thr Leu Leu Arg Lys Tyr Ala Glu Glu Arg Asn Gly Val Asn Val Val
                675                 680                 685

Ser Gly Pro Val Phe Asp Phe Asp Tyr Asp Gly Arg Cys Asp Ser Leu
690                 695                 700

Glu Asn Leu Arg Gln Lys Arg Arg Val Ile Arg Asn Gln Glu Ile Leu
705                 710                 715                 720

Ile Pro Thr His Phe Phe Ile Val Leu Thr Ser Cys Lys Asp Thr Ser
                725                 730                 735

Gln Thr Pro Leu His Cys Glu Asn Leu Asp Thr Leu Ala Phe Ile Leu
                740                 745                 750

Pro His Arg Thr Asp Asn Ser Glu Ser Cys Val His Gly Lys His Asp
                755                 760                 765

Ser Ser Trp Val Glu Glu Leu Leu Met Leu His Arg Ala Arg Ile Thr
770                 775                 780

Asp Val Glu His Ile Thr Gly Leu Ser Phe Tyr Gln Gln Arg Lys Glu
785                 790                 795                 800

Pro Val Ser Asp Ile Leu Lys Leu Lys Thr His Leu Pro Thr Phe Ser
                805                 810                 815

Gln Glu Asp Asp Lys Thr His Thr Cys Pro Pro Cys Pro Ala Pro Glu
                820                 825                 830

Leu Leu Gly Gly Pro Ser Val Phe Leu Phe Pro Pro Lys Pro Lys Asp
                835                 840                 845

Thr Leu Met Ile Ser Arg Thr Pro Glu Val Thr Cys Val Val Val Asp
850                 855                 860

Val Ser His Glu Asp Pro Glu Val Lys Phe Asn Trp Tyr Val Asp Gly
865                 870                 875                 880

Val Glu Val His Asn Ala Lys Thr Lys Pro Arg Glu Glu Gln Tyr Asn
                885                 890                 895

Ser Thr Tyr Arg Val Val Ser Val Leu Thr Val Leu His Gln Asp Trp
                900                 905                 910

Leu Asn Gly Lys Glu Tyr Lys Cys Lys Val Ser Asn Lys Ala Leu Pro
                915                 920                 925

Ala Pro Ile Glu Lys Thr Ile Ser Lys Ala Lys Gly Gln Pro Arg Glu
930                 935                 940
```

```
Pro Gln Val Tyr Thr Leu Pro Pro Ser Arg Glu Glu Met Thr Lys Asn
945                 950                 955                 960

Gln Val Ser Leu Thr Cys Leu Val Lys Gly Phe Tyr Pro Ser Asp Ile
                965                 970                 975

Ala Val Glu Trp Glu Ser Asn Gly Gln Pro Glu Asn Asn Tyr Lys Thr
            980                 985                 990

Thr Pro Pro Val Leu Asp Ser Asp Gly Ser Phe Phe Leu Tyr Ser Lys
        995                 1000                1005

Leu Thr Val Asp Lys Ser Arg Trp Gln Gln Gly Asn Val Phe Ser
    1010                1015                1020

Cys Ser Val Met His Glu Ala Leu His Asn His Tyr Thr Gln Lys
    1025                1030                1035

Ser Leu Ser Leu Ser Pro Gly Lys
    1040                1045

<210> SEQ ID NO 11
<211> LENGTH: 971
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Glu Lys Ser Trp Val Glu Pro Cys Glu Ser Ile Asn Glu Pro Gln
1               5                   10                  15

Cys Pro Ala Gly Phe Glu Thr Pro Thr Leu Leu Phe Ser Leu Asp
            20                  25                  30

Gly Phe Arg Ala Glu Tyr Leu His Thr Trp Gly Gly Leu Leu Pro Val
        35                  40                  45

Ile Ser Lys Leu Lys Lys Cys Gly Thr Tyr Thr Lys Asn Met Arg Pro
50                  55                  60

Val Tyr Pro Thr Lys Thr Phe Pro Asn His Tyr Ser Ile Val Thr Gly
65                  70                  75                  80

Leu Tyr Pro Glu Ser His Gly Ile Ile Asp Lys Met Tyr Asp Pro
            85                  90                  95

Lys Met Asn Ala Ser Phe Ser Leu Lys Ser Lys Glu Lys Phe Asn Pro
            100                 105                 110

Glu Trp Tyr Lys Gly Glu Pro Ile Trp Val Thr Ala Lys Tyr Gln Gly
            115                 120                 125

Leu Lys Ser Gly Thr Phe Phe Trp Pro Gly Ser Asp Val Glu Ile Asn
        130                 135                 140

Gly Ile Phe Pro Asp Ile Tyr Lys Met Tyr Asn Gly Ser Val Pro Phe
145                 150                 155                 160

Glu Glu Arg Ile Leu Ala Val Leu Gln Trp Leu Gln Leu Pro Lys Asp
                165                 170                 175

Glu Arg Pro His Phe Tyr Thr Leu Tyr Leu Glu Glu Pro Asp Ser Ser
            180                 185                 190

Gly His Ser Tyr Gly Pro Val Ser Ser Glu Val Ile Lys Ala Leu Gln
        195                 200                 205

Arg Val Asp Gly Met Val Gly Met Leu Met Asp Gly Leu Lys Glu Leu
    210                 215                 220

Asn Leu His Arg Cys Leu Asn Leu Ile Leu Ile Ser Asp His Gly Met
225                 230                 235                 240
```

```
Glu Gln Gly Ser Cys Lys Lys Tyr Ile Tyr Leu Asn Lys Tyr Leu Gly
                245                 250                 255

Asp Val Lys Asn Ile Lys Val Ile Tyr Gly Pro Ala Ala Arg Leu Arg
                260                 265                 270

Pro Ser Asp Val Pro Asp Lys Tyr Tyr Ser Phe Asn Tyr Glu Gly Ile
                275                 280                 285

Ala Arg Asn Leu Ser Cys Arg Glu Pro Asn Gln His Phe Lys Pro Tyr
                290                 295                 300

Leu Lys His Phe Leu Pro Lys Arg Leu His Phe Ala Lys Ser Asp Arg
305                 310                 315                 320

Ile Glu Pro Leu Thr Phe Tyr Leu Asp Pro Gln Trp Gln Leu Ala Leu
                325                 330                 335

Asn Pro Ser Glu Arg Lys Tyr Cys Gly Ser Gly Phe His Gly Ser Asp
                340                 345                 350

Asn Val Phe Ser Asn Met Gln Ala Leu Phe Val Gly Tyr Gly Pro Gly
                355                 360                 365

Phe Lys His Gly Ile Glu Ala Asp Thr Phe Glu Asn Ile Glu Val Tyr
                370                 375                 380

Asn Leu Met Cys Asp Leu Leu Asn Leu Thr Pro Ala Pro Asn Asn Gly
385                 390                 395                 400

Thr His Gly Ser Leu Asn His Leu Leu Lys Asn Pro Val Tyr Thr Pro
                405                 410                 415

Lys His Pro Lys Glu Val His Pro Leu Val Gln Cys Pro Phe Thr Arg
                420                 425                 430

Asn Pro Arg Asp Asn Leu Gly Cys Ser Cys Asn Pro Ser Ile Leu Pro
                435                 440                 445

Ile Glu Asp Phe Gln Thr Gln Phe Asn Leu Thr Val Ala Glu Glu Lys
                450                 455                 460

Ile Ile Lys His Glu Thr Leu Pro Tyr Gly Arg Pro Arg Val Leu Gln
465                 470                 475                 480

Lys Glu Asn Thr Ile Cys Leu Leu Ser Gln His Gln Phe Met Ser Gly
                485                 490                 495

Tyr Ser Gln Asp Ile Leu Met Pro Leu Trp Thr Ser Tyr Thr Val Asp
                500                 505                 510

Arg Asn Asp Ser Phe Ser Thr Glu Asp Phe Ser Asn Cys Leu Tyr Gln
                515                 520                 525

Asp Phe Arg Ile Pro Leu Ser Pro Val His Lys Cys Ser Phe Tyr Lys
                530                 535                 540

Asn Asn Thr Lys Val Ser Tyr Gly Phe Leu Ser Pro Pro Gln Leu Asn
545                 550                 555                 560

Lys Asn Ser Ser Gly Ile Tyr Ser Glu Ala Leu Leu Thr Thr Asn Ile
                565                 570                 575

Val Pro Met Tyr Gln Ser Phe Gln Val Ile Trp Arg Tyr Phe His Asp
                580                 585                 590

Thr Leu Leu Arg Lys Tyr Ala Glu Glu Arg Asn Gly Val Asn Val Val
                595                 600                 605

Ser Gly Pro Val Phe Asp Phe Asp Tyr Asp Gly Arg Cys Asp Ser Leu
                610                 615                 620

Glu Asn Leu Arg Gln Lys Arg Arg Val Ile Arg Asn Gln Glu Ile Leu
625                 630                 635                 640

Ile Pro Thr His Phe Phe Ile Val Leu Thr Ser Cys Lys Asp Thr Ser
                645                 650                 655
```

```
Gln Thr Pro Leu His Cys Glu Asn Leu Asp Thr Leu Ala Phe Ile Leu
            660                 665                 670

Pro His Arg Thr Asp Asn Ser Glu Ser Cys Val His Gly Lys His Asp
        675                 680                 685

Ser Ser Trp Val Glu Leu Leu Met Leu His Arg Ala Arg Ile Thr
690                 695                 700

Asp Val Glu His Ile Thr Gly Leu Ser Phe Tyr Gln Gln Arg Lys Glu
705                 710                 715                 720

Pro Val Ser Asp Ile Leu Lys Leu Lys Thr His Leu Pro Thr Phe Ser
            725                 730                 735

Gln Glu Asp Glu Pro Lys Ser Cys Asp Lys Thr His Thr Cys Pro Pro
            740                 745                 750

Cys Pro Ala Pro Glu Leu Leu Gly Gly Pro Ser Val Phe Leu Phe Pro
            755                 760                 765

Pro Lys Pro Lys Asp Thr Leu Met Ile Ser Arg Thr Pro Glu Val Thr
            770                 775                 780

Cys Val Val Val Asp Val Ser His Glu Asp Pro Glu Val Lys Phe Asn
785                 790                 795                 800

Trp Tyr Val Asp Gly Val Glu Val His Asn Ala Lys Thr Lys Pro Arg
            805                 810                 815

Glu Glu Gln Tyr Asn Ser Thr Tyr Arg Val Val Ser Val Leu Thr Val
            820                 825                 830

Leu His Gln Asp Trp Leu Asn Gly Lys Glu Tyr Lys Cys Lys Val Ser
            835                 840                 845

Asn Lys Ala Leu Pro Ala Pro Ile Glu Lys Thr Ile Ser Lys Ala Lys
850                 855                 860

Gly Gln Pro Arg Glu Pro Gln Val Tyr Thr Leu Pro Pro Ser Arg Glu
865                 870                 875                 880

Glu Met Thr Lys Asn Gln Val Ser Leu Thr Cys Leu Val Lys Gly Phe
            885                 890                 895

Tyr Pro Ser Asp Ile Ala Val Glu Trp Glu Ser Asn Gly Gln Pro Glu
            900                 905                 910

Asn Asn Tyr Lys Thr Thr Pro Pro Val Leu Asp Ser Asp Gly Ser Phe
            915                 920                 925

Phe Leu Tyr Ser Lys Leu Thr Val Asp Lys Ser Arg Trp Gln Gln Gly
            930                 935                 940

Asn Val Phe Ser Cys Ser Val Met His Glu Ala Leu His Asn His Tyr
945                 950                 955                 960

Thr Gln Lys Ser Leu Ser Leu Ser Pro Gly Lys
            965                 970

<210> SEQ ID NO 12
<211> LENGTH: 966
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Glu Lys Ser Trp Val Glu Glu Pro Cys Glu Ser Ile Asn Glu Pro Gln
1               5                   10                  15

Cys Pro Ala Gly Phe Glu Thr Pro Pro Thr Leu Leu Phe Ser Leu Asp
            20                  25                  30
```

```
Gly Phe Arg Ala Glu Tyr Leu His Thr Trp Gly Gly Leu Leu Pro Val
         35                  40                  45
Ile Ser Lys Leu Lys Lys Cys Gly Thr Tyr Thr Lys Asn Met Arg Pro
 50                  55                  60
Val Tyr Pro Thr Lys Thr Phe Pro Asn His Tyr Ser Ile Val Thr Gly
 65                  70                  75                  80
Leu Tyr Pro Glu Ser His Gly Ile Ile Asp Asn Lys Met Tyr Asp Pro
                 85                  90                  95
Lys Met Asn Ala Ser Phe Ser Leu Lys Ser Lys Glu Lys Phe Asn Pro
                100                 105                 110
Glu Trp Tyr Lys Gly Glu Pro Ile Trp Val Thr Ala Lys Tyr Gln Gly
            115                 120                 125
Leu Lys Ser Gly Thr Phe Phe Trp Pro Gly Ser Asp Val Glu Ile Asn
    130                 135                 140
Gly Ile Phe Pro Asp Ile Tyr Lys Met Tyr Asn Gly Ser Val Pro Phe
145                 150                 155                 160
Glu Glu Arg Ile Leu Ala Val Leu Gln Trp Leu Gln Leu Pro Lys Asp
                165                 170                 175
Glu Arg Pro His Phe Tyr Thr Leu Tyr Leu Glu Glu Pro Asp Ser Ser
            180                 185                 190
Gly His Ser Tyr Gly Pro Val Ser Ser Glu Val Ile Lys Ala Leu Gln
    195                 200                 205
Arg Val Asp Gly Met Val Gly Met Leu Met Asp Gly Leu Lys Glu Leu
210                 215                 220
Asn Leu His Arg Cys Leu Asn Leu Ile Leu Ile Ser Asp His Gly Met
225                 230                 235                 240
Glu Gln Gly Ser Cys Lys Lys Tyr Ile Tyr Leu Asn Lys Tyr Leu Gly
                245                 250                 255
Asp Val Lys Asn Ile Lys Val Ile Tyr Gly Pro Ala Ala Arg Leu Arg
            260                 265                 270
Pro Ser Asp Val Pro Asp Lys Tyr Tyr Ser Phe Asn Tyr Glu Gly Ile
    275                 280                 285
Ala Arg Asn Leu Ser Cys Arg Glu Pro Asn Gln His Phe Lys Pro Tyr
290                 295                 300
Leu Lys His Phe Leu Pro Lys Arg Leu His Phe Ala Lys Ser Asp Arg
305                 310                 315                 320
Ile Glu Pro Leu Thr Phe Tyr Leu Asp Pro Gln Trp Gln Leu Ala Leu
                325                 330                 335
Asn Pro Ser Glu Arg Lys Tyr Cys Gly Ser Gly Phe His Gly Ser Asp
            340                 345                 350
Asn Val Phe Ser Asn Met Gln Ala Leu Phe Val Gly Tyr Gly Pro Gly
    355                 360                 365
Phe Lys His Gly Ile Glu Ala Asp Thr Phe Glu Asn Ile Glu Val Tyr
    370                 375                 380
Asn Leu Met Cys Asp Leu Leu Asn Leu Thr Pro Ala Pro Asn Asn Gly
385                 390                 395                 400
Thr His Gly Ser Leu Asn His Leu Leu Lys Asn Pro Val Tyr Thr Pro
                405                 410                 415
Lys His Pro Lys Glu Val His Pro Leu Val Gln Cys Pro Phe Thr Arg
            420                 425                 430
Asn Pro Arg Asp Asn Leu Gly Cys Ser Cys Asn Pro Ser Ile Leu Pro
435                 440                 445
```

-continued

Ile Glu Asp Phe Gln Thr Gln Phe Asn Leu Thr Val Ala Glu Glu Lys
    450                 455                 460

Ile Ile Lys His Glu Thr Leu Pro Tyr Gly Arg Pro Arg Val Leu Gln
465                 470                 475                 480

Lys Glu Asn Thr Ile Cys Leu Leu Ser Gln His Gln Phe Met Ser Gly
                485                 490                 495

Tyr Ser Gln Asp Ile Leu Met Pro Leu Trp Thr Ser Tyr Thr Val Asp
                500                 505                 510

Arg Asn Asp Ser Phe Ser Thr Glu Asp Phe Ser Asn Cys Leu Tyr Gln
            515                 520                 525

Asp Phe Arg Ile Pro Leu Ser Pro Val His Lys Cys Ser Phe Tyr Lys
530                 535                 540

Asn Asn Thr Lys Val Ser Tyr Gly Phe Leu Ser Pro Pro Gln Leu Asn
545                 550                 555                 560

Lys Asn Ser Ser Gly Ile Tyr Ser Glu Ala Leu Leu Thr Thr Asn Ile
                565                 570                 575

Val Pro Met Tyr Gln Ser Phe Gln Val Ile Trp Arg Tyr Phe His Asp
            580                 585                 590

Thr Leu Leu Arg Lys Tyr Ala Glu Glu Arg Asn Gly Val Asn Val Val
        595                 600                 605

Ser Gly Pro Val Phe Asp Phe Asp Tyr Asp Gly Arg Cys Asp Ser Leu
    610                 615                 620

Glu Asn Leu Arg Gln Lys Arg Arg Val Ile Arg Asn Gln Glu Ile Leu
625                 630                 635                 640

Ile Pro Thr His Phe Phe Ile Val Leu Thr Ser Cys Lys Asp Thr Ser
                645                 650                 655

Gln Thr Pro Leu His Cys Glu Asn Leu Asp Thr Leu Ala Phe Ile Leu
            660                 665                 670

Pro His Arg Thr Asp Asn Ser Glu Ser Cys Val His Gly Lys His Asp
        675                 680                 685

Ser Ser Trp Val Glu Glu Leu Leu Met Leu His Arg Ala Arg Ile Thr
    690                 695                 700

Asp Val Glu His Ile Thr Gly Leu Ser Phe Tyr Gln Gln Arg Lys Glu
705                 710                 715                 720

Pro Val Ser Asp Ile Leu Lys Leu Lys Thr His Leu Pro Thr Phe Ser
                725                 730                 735

Gln Glu Asp Asp Lys Thr His Thr Cys Pro Pro Cys Pro Ala Pro Glu
            740                 745                 750

Leu Leu Gly Gly Pro Ser Val Phe Leu Phe Pro Pro Lys Pro Lys Asp
        755                 760                 765

Thr Leu Met Ile Ser Arg Thr Pro Glu Val Thr Cys Val Val Val Asp
    770                 775                 780

Val Ser His Glu Asp Pro Glu Val Lys Phe Asn Trp Tyr Val Asp Gly
785                 790                 795                 800

Val Glu Val His Asn Ala Lys Thr Lys Pro Arg Glu Glu Gln Tyr Asn
                805                 810                 815

Ser Thr Tyr Arg Val Val Ser Val Leu Thr Val Leu His Gln Asp Trp
            820                 825                 830

Leu Asn Gly Lys Glu Tyr Lys Cys Lys Val Ser Asn Lys Ala Leu Pro
        835                 840                 845

Ala Pro Ile Glu Lys Thr Ile Ser Lys Ala Lys Gly Gln Pro Arg Glu
    850                 855                 860

```
Pro Gln Val Tyr Thr Leu Pro Pro Ser Arg Glu Glu Met Thr Lys Asn
865                 870                 875                 880

Gln Val Ser Leu Thr Cys Leu Val Lys Gly Phe Tyr Pro Ser Asp Ile
            885                 890                 895

Ala Val Glu Trp Glu Ser Asn Gly Gln Pro Glu Asn Asn Tyr Lys Thr
        900                 905                 910

Thr Pro Pro Val Leu Asp Ser Asp Gly Ser Phe Phe Leu Tyr Ser Lys
            915                 920                 925

Leu Thr Val Asp Lys Ser Arg Trp Gln Gln Gly Asn Val Phe Ser Cys
        930                 935                 940

Ser Val Met His Glu Ala Leu His Asn His Tyr Thr Gln Lys Ser Leu
945                 950                 955                 960

Ser Leu Ser Pro Gly Lys
                965

<210> SEQ ID NO 13
<211> LENGTH: 15
<212> TYPE: PRT
<213> ORGANISM: Homo sapiens

<400> SEQUENCE: 13

Glu Pro Lys Ser Cys Asp Lys Thr His Thr Cys Pro Pro Cys Pro
1               5                   10                  15

<210> SEQ ID NO 14
<211> LENGTH: 10
<212> TYPE: PRT
<213> ORGANISM: Homo sapiens

<400> SEQUENCE: 14

Asp Lys Thr His Thr Cys Pro Pro Cys Pro
1               5                   10

<210> SEQ ID NO 15
<211> LENGTH: 14
<212> TYPE: PRT
<213> ORGANISM: Homo sapiens

<400> SEQUENCE: 15

Pro Lys Ser Cys Asp Lys Thr His Thr Cys Pro Pro Cys Pro
1               5                   10

<210> SEQ ID NO 16
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Gly Gly Gly Gly Ser Gly Gly Gly Ser Gly Gly Gly Gly Ser
1               5                   10                  15

<210> SEQ ID NO 17
<211> LENGTH: 6
<212> TYPE: PRT
<213> ORGANISM: Homo sapiens

<400> SEQUENCE: 17

Pro Ser Cys Ala Lys Glu
1               5
```

```
<210> SEQ ID NO 18
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Asp Asp Asp Asp Asp Asp Asp Asp Asp Asp
1               5                   10

<210> SEQ ID NO 19
<211> LENGTH: 50
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MISC_FEATURE
<222> LOCATION: (1)..(50)
<223> OTHER INFORMATION: /note="This sequence may encompass 1-10 'Gly
      Gly Gly Gly Ser' repeating units"

<400> SEQUENCE: 19

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
    50

<210> SEQ ID NO 20
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Asp Asp Asp Asp Asp Asp Asp Asp
1               5

<210> SEQ ID NO 21
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Glu Glu Glu Glu Glu Glu Glu Glu
1               5
```

METHODS OF IMPROVING CARDIOVASCULAR FUNCTION AND TREATING CARDIOVASCULAR DISEASE USING A RECOMBINANT ECTONUCLEOTIDE PYROPHOSPHATASE PHOSPHODIESTERASE (NPP1)

RELATED INFORMATION PARAGRAPH

This application is a 35 U.S.C. 371 national stage filing of International Application No. PCT/US2018/052795, filed on Sep. 26, 2018, which claims the benefit of the priority date of U.S. Provisional Application No. 62/563,829, filed on Sep. 27, 2017, the contents of each of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Mar. 18, 2020, is named AXJ-241US Sequence Listing and is 88,857 bytes in size.

BACKGROUND

The cardiovascular system, also known as the circulatory system, includes the heart, arteries, veins, capillaries and blood. The heart functions as the pump that moves blood through the body. The arterial circulation delivers blood from the heart to the body, and the venous circulation carries it back to the heart. Capillaries are tiny blood vessels at the interface of the arterial and venous circulation where exchange of substances between the blood and body tissues occurs. The three main functions of the cardiovascular system are (1) the transport of nutrients, oxygen, and hormones to cells throughout the body and removal of metabolic wastes (carbon dioxide, nitrogenous wastes), (2) protection of the body by white blood cells, antibodies, and complement proteins that circulate in the blood and defend the body against foreign microbes and toxins, as well as clotting mechanisms that protect the body from blood loss after injuries, and (3) regulation of body temperature, fluid pH, and water content of cells.

Cardiovascular diseases are the leading cause of death globally. Cardiovascular disease includes coronary artery diseases (CAD) (such as angina and myocardial infarction (commonly known as a heart attack), stroke, heart failure, hypertensive heart disease, rheumatic heart disease, cardiomyopathy, heart arrhythmia, congenital heart disease, valvular heart disease, carditis, aortic aneurysms, peripheral artery disease, thromboembolic disease, and venous thrombosis (see GBD 2013 Mortality and Causes of Death, Collaborators (17 Dec. 2014), Lancet. 385 (9963): 117-71).

Approximately 85 million people in the United States have hypertension (also known as "high blood pressure"). Normal blood pressure is 120 over 80 mm of mercury (mmHg). Medical guidelines define hypertension as a blood pressure higher than 140 over 90 millimeters of mercury (mmHg). Blood pressure is the force exerted by the blood against the walls of the blood vessels. The systolic reading of 140 mmHg refers to the pressure as the heart pumps blood around the body. The diastolic reading of 90 mmHg refers to the pressure as the heart relaxes and refills with blood. Hypertension severely impacts quality of life and increases the risk of heart disease, stroke, and death.

In spite of considerable research in the field, there is a continuing need for therapies to effectively treat cardiovascular diseases, including hypertension.

SUMMARY OF THE INVENTION

The present invention relates to uses of isolated recombinant human soluble NPP1 that lacks N-terminal cytosolic and transmembrane domains and fusion proteins thereof for improving cardiovascular function in a human patient, including preventing and/or treating cardiovascular diseases, such as hypertension. Any cardiovascular disorder is within the scope of the present invention.

In one aspect, method for improving cardiovascular function in a human patient are provided, the method comprising administering to the patient one or more doses of a recombinant human soluble ectonucleotide pyrophosphatase phosphodiesterase (hsNPP1), active fragment or fusion protein thereof. In one embodiment, the improvement is a reduction in elevated blood pressure (e.g., reduction of blood pressure higher than 140 over 90 millimeters of mercury (mmHg) to within a normal blood pressure range (about 120 over 80 mm of mercury (mmHg)). In another embodiment, the improvement is a reduction in elevated blood pressure by at least 5 (e.g., at least 10, 15, 20, 25, 30, 35, 40, 45, 50, 55, 60, 65, or 70)%. In another embodiment, the improvement is a reduction in elevated blood pressure by about 1.5-fold, 2-fold, 2.5-fold, 3-fold, 3.5-fold, or 4-fold. In another embodiment, the improvement is a normalization of blood pressure (e.g., to about 120 over 80 mm of mercury (mmHg)). In another embodiment, the improvement is a reduction in left ventricular end-diastolic pressure (EDP) and end-systolic pressure (ESP) (e.g., by at least 5, 10, 15, 20, 25, 30, 35, 40, 45, 50, 55, 60, 65, or 70%). In another embodiment, the improvement is a reduction in left ventricular EDP and ESP by about 1.5-fold, 2-fold, 2.5-fold, 3-fold, 3.5-fold, or 4-fold. In another embodiment, the improvement is a reduction in ventricle stiffness (EDPVR) (e.g., by at least 5, 10, 15, 20, 25, 30, 35, 40, 45, 50, 55, 60, 65, or 70%). In another embodiment, the improvement is a reduction in ventricle stiffness by about 1.5-fold, 2-fold, 2.5-fold, 3-fold, 3.5-fold, or 4-fold. In another embodiment, the improvement is in increase in contractility (PRSW) (e.g., by at least 5, 10, 15, 20, 25, 30, 35, 40, 45, 50, 55, 60, 65, or 70%). In another embodiment, the improvement is in increase in contractility by about 1.5-fold, 2-fold, 2.5-fold, 3-fold, 3.5-fold, or 4-fold.

In another aspect, methods for treating a human patient having a cardiovascular disorder are provided, the method comprising administering to the patient one or more doses of a recombinant human soluble ectonucleotide pyrophosphatase phosphodiesterase (hsNPP1), active fragment or fusion protein thereof. Exemplary cardiovascular diseases include, but are not limited to, coronary artery diseases (CAD) (such as angina and myocardial infarction (commonly known as a heart attack), stroke, heart failure, hypertensive heart disease, rheumatic heart disease, cardiomyopathy, heart arrhythmia, congenital heart disease, valvular heart disease, carditis, aortic aneurysms, peripheral artery disease, thromboembolic disease, and venous thrombosis.

In another aspect, methods for treating a human patient having hypertension are provided, the method comprising administering to the patient one or more doses of a recombinant human soluble ectonucleotide pyrophosphatase phosphodiesterase (hsNPP1), active fragment or fusion protein thereof.

In another aspect, methods of treating a human patient having hypertension are provided, the method comprising: a) identifying a human patient as having hypertension and b) administering to the identified patient one or more doses of a recombinant human soluble ectonucleotide pyrophosphatase phosphodiesterase (hsNPP1), active fragment or fusion protein thereof.

In another aspect, methods for reducing hypertension in a human patient are provided, the method comprising administering to the patient one or more doses of a recombinant human soluble ectonucleotide pyrophosphatase phosphodiesterase (hsNPP1), active fragment or fusion protein thereof.

In one embodiment, the methods described herein result in a reduction in the patient's blood pressure (e.g., from an elevated blood pressure higher than about 140 over 90 millimeters of mercury (mmHg) to within a normal blood pressure range (about 120 over 80 mm of mercury (mmHg)). In another embodiment, the patient's blood pressure is reduced by at least 5 (e.g., at least 10, 15, 20, 25, 30, 35, 40, 45, 50, 55, 60, 65, or 70)% after treatment. In another embodiment, the patient's blood pressure is reduced by about 1.5-fold, 2-fold, 2.5-fold, 3-fold, 3.5-fold, or 4-fold after treatment. In another embodiment, the patient's blood pressure is normalized after treatment (e.g., to about 120 over 80 mm of mercury (mmHg)).

In one embodiment, a NPP1 fusion protein is administered. Preferred fusion proteins comprise and NPP1 component an Fc region of an immunoglobulin and, optionally, a targeting moiety. In one embodiment, the targeting moiety is $Asp_{10}$ (SEQ ID NO: 18). In another embodiment, the targeting moiety comprises at least eight consecutive aspartic acid or glutamic acid residues (SEQ ID NOS 20 and 21, respectively). Particular NPP1 fusion proteins for administration in accordance with the methods disclosed herein have the amino acid sequence set forth in SEQ ID NO:3, SEQ ID NO:4, SEQ ID NO:9, SEQ ID NO:10, SEQ ID NO:11 or SEQ ID NO:12.

Any suitable amount of the recombinant hsNPP1 can be administered to the human patient. In one embodiment, the hsNPP1 is administered in one or more doses containing about 0.5 mg/kg, 1.0 mg/kg, 2.0 mg/kg, 3.0 mg/kg, 4.0 mg/kg, 5.0 mg/kg, 6.0 mg/kg, 7.0 mg/kg, 8.0 mg/kg, 9.0 mg/kg, 10.0 mg/kg, 11.0 mg/kg, 12.0 mg/kg, 13.0 mg/kg, 14.0 mg/kg, 15.0 mg/kg, 16.0 mg/kg, 17.0 mg/kg, 18.0 mg/kg, 19.0 mg/kg, or 20.0 mg/kg. In another embodiment, the hsNPP1 is administered in one or more doses containing about 1.0 mg/kg to about 5.0 mg/kg NPP1. In another embodiment, the hsNPP1 is administered in one or more doses containing about 1.0 mg/kg to about 10.0 mg/kg NPP1.

The time period between doses of the hsNPP1 is at least 2 days and can be longer, for example at least 3 days, at least 1 week, 2 weeks or 1 month. In one embodiment, the administration is weekly, bi-weekly, or monthly.

The recombinant hsNPP1 can be administered in any suitable way, such as intravenously, subcutaneously, or intraperitoneally.

The recombinant hsNPP1 can be administered in combination with one or more additional therapeutic agents. Exemplary therapeutic agents include, but are not limited to a thiazide diuretic (e.g., hydrochlorothiazide (Microzide) or chlorthalidone), a beta blocker (e.g., acebutolol (Sectral) or atenolol (Tenormin)), an angiotensin-converting enzyme (ACE) inhibitor (e.g., lisinopril (Zestril), benazepril (Lotensin), or captopril (Capoten)), an angiotensin II receptor blocker (ARB) (e.g., candesartan (Atacand) or losartan (Cozaar)), a calcium channel blocker (e.g., amlodipine (Norvasc) or diltiazem (Cardizem)), a renin inhibitor (e.g., Aliskiren (Tekturna)), an alpha blocker (e.g., doxazosin (Cardura) or prazosin (Minipress)), an alpha-beta blocker (e.g., carvedilol (Coreg) or labetalol (Trandate)), a central-acting agent (e.g., clonidine (Catapres, Kapvay), guanfacine (Intuniv, Tenex) and methyldopa), a vasodilator (e.g., hydralazine and minoxidil), and/or an aldosterone antagonist (e.g., spironolactone (Aldactone) or eplerenone (Inspra)). In one embodiment, the recombinant hsNPP1 and additional therapeutic agent are administered separately and are administered concurrently or sequentially. In one embodiment, the recombinant hsNPP1 is administered prior to administration of the additional therapeutic agent. In another embodiment, the recombinant hsNPP1 is administered after administration of the additional therapeutic agent. In another embodiment, the recombinant hsNPP1 and additional therapeutic agent are administered together.

In another aspect uses of an isolated recombinant human sNPP1, fragment or fusion protein thereof are provided. In one embodiment, the use of an isolated recombinant human sNPP1, fragment or fusion protein thereof for the manufacture of a medicament for improving cardiovascular function is provided. In another embodiment, the use of an isolated recombinant human sNPP1, fragment or fusion protein thereof for the manufacture of a medicament for reducing hypertension is provided. In another embodiment, the invention provides the use of an isolated recombinant human sNPP1, fragment or fusion protein thereof for reducing hypertension. In another embodiment, the invention provides the use of an isolated recombinant human sNPP1, fragment or fusion protein thereof for treating hypertension. In another embodiment, the invention provides the use of an isolated recombinant human sNPP1, fragment or fusion protein thereof for improving cardiovascular function in a patient.

Other features and advantages of the invention will be apparent from the following detailed description and claims.

BRIEF DESCRIPTION OF THE DRAWINGS

FIGS. 5A-5C is data from pressure volume loops that indicates that Enpp1-treatment reduces ventricle stiffness (EDPVR) and increases contractility (PRSW) in Asj-2J mice.

FIGS. 6A-6J is echocardiogram data which suggests that Asj-2J mice do not have left ventricular hypertrophy (no change in LV Diastolic Anterior/Posterior Wall Thickness, internal dimensions, End-Diastolic Area, and Estimated LV Mass).

DETAILED DESCRIPTION

Definitions

Figure 1:
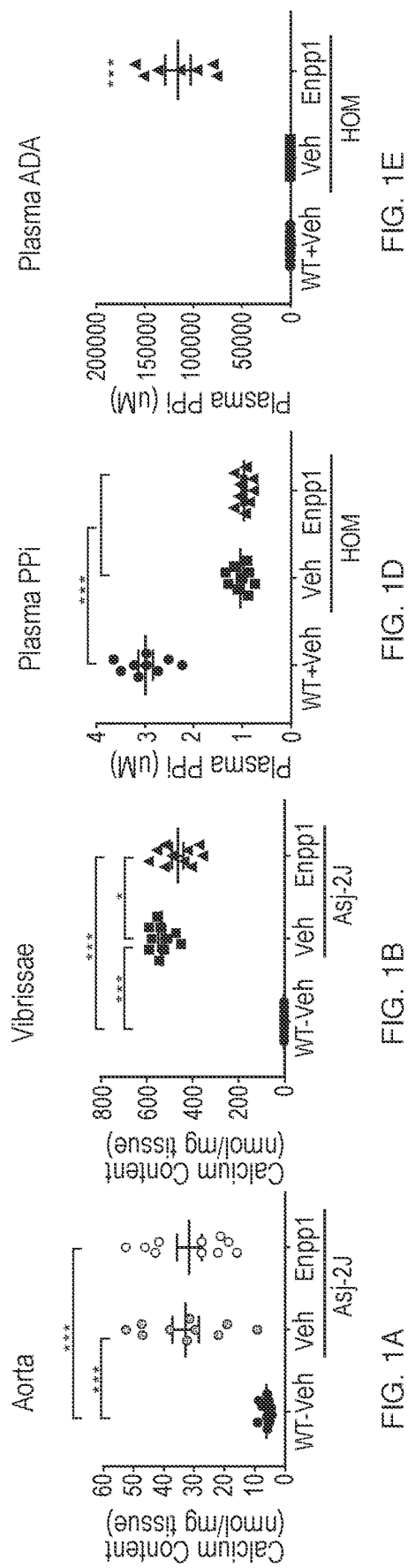
FIGS. 1A-1E show that there was no reduction in calcification (FIGS. 1A-1C), no increase in plasma pyrophosphate (PPi) levels (FIG. 1D), and high plasma anti-drug antibody ("ADA") levels (FIG. 1E) in ENPP1-treated 2J mice after 6 weeks of treatment.

Unless defined otherwise, all technical and scientific terms used herein have the same meaning as commonly understood by one of ordinary skill in the art to which this invention belongs. Although any methods and materials similar or equivalent to those described herein can be used in practice or testing of the present invention, the preferred methods and materials are described.

For clarity, "NPP1" and "ENPP1" refer to the same protein and are used interchangeably herein.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the term "normal," when used to modify the term "individual" or "subject" refers to an individual or group of individuals who does/do not have a particular disease or condition (e.g., a cardiovascular disorder) and is also not suspected of having or being at risk for developing the disease or condition. The term "normal" is also used herein to qualify a biological specimen or sample isolated from a normal or healthy individual or subject (or group of such subjects), for example, a "normal control sample" or "normal control".

As used herein, the term "fragment", with regard to NPP1 proteins, refers to an active subsequence of the full-length NPP1. A "fragment" of a protein or peptide can be at least about 20 amino acids in length; for example, at least about 50 amino acids in length; at least about 100 amino acids in length; at least about 200 amino acids in length; at least about 300 amino acids in length; or at least about 400 amino acids in length (and any integer value in between). The fragments may range in size from four amino acid residues to the entire amino acid sequence minus one amino acid. Thus, a protein "comprising at least a portion of the amino acid sequence of SEQ ID NO: 1" encompasses the full-length NPP1 and fragments thereof.

An "isolated" or "purified" soluble NPP1 protein or biologically active fragment or fusion protein thereof is substantially free of cellular material or other contaminating proteins from the cell or tissue source from which the NPP1 protein, biologically active fragment or NPP1 fusion protein is derived, or substantially free from chemical precursors or other chemicals when chemically synthesized. The language "substantially free of cellular material" includes preparations of NPP1 protein, biologically active fragment, or NPP1 fusion protein in which the protein is separated from cellular components of the cells from which it is isolated or recombinantly produced. In one embodiment, the language "substantially free of cellular material" includes preparations of NPP1 protein, biologically active fragment or NPP1 fusion protein having less than about 30% (by dry weight) of non-NPP1 protein/fragment/fusion protein (also referred to herein as a "contaminating protein"), more preferably less than about 20% of non-NPP1 protein/fragment/fusion protein, still more preferably less than about 10% of non-NPP1 protein/fragment/fusion protein, and most preferably less than about 5% non-NPP1 protein/fragment/fusion protein. When the NPP1 protein, fusion protein, or biologically active fragment thereof is recombinantly produced, it is also preferably substantially free of culture medium, i.e., culture medium represents less than about 20%, more preferably less than about 10%, and most preferably less than about 5% of the volume of the protein preparation.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

As used herein, the term "subject" encompasses mammals and non-mammals. Examples of mammals include, but are not limited to, humans, chimpanzees, apes monkeys, cattle, horses, sheep, goats, swine, rabbits, dogs, cats, rats, mice, guinea pigs, and the like. Examples of non-mammals include, but are not limited to, birds, fish and the like.

As used herein, the term "therapeutically effective amount" refers to a nontoxic but sufficient amount of an agent (e.g., hsNPP1 proteins) which, as compared to a corresponding subject who has not received such amount, results in improved treatment, healing, prevention, or amelioration of a disease, disorder, or side effect, or a decrease in the rate of advancement of a disease or disorder (e.g., a cardiac disease or disorder). The term also includes within its scope amounts effective to enhance normal physiological function.

As used herein, a cardiovascular disease or disorder is one that involves the heart or blood vessels. Exemplary cardiovascular diseases include, but are not limited to, coronary artery diseases (CAD) (such as angina and myocardial infarction (commonly known as a heart attack), stroke, heart failure, hypertension, rheumatic heart disease, cardiomyopathy, heart arrhythmia, congenital heart disease, valvular heart disease, carditis, aortic aneurysms, peripheral artery disease, thromboembolic disease, and venous thrombosis.

As used herein, "hypertension" (also known as "high blood pressure") is defined as a blood pressure higher than 140 over 90 millimeters of mercury (mmHg). Blood pressure is the force exerted by the blood against the walls of the blood vessels. The systolic reading of 140 mmHg refers to the pressure as the heart pumps blood around the body. The diastolic reading of 90 mmHg refers to the pressure as the heart relaxes and refills with blood. Normal blood pressure is 120 over 80 mm of mercury (mmHg). Hypertension severely impacts quality of life and increases the risk of heart disease, stroke, and death.

High blood pressure that is not caused by another condition or disease is called "primary" or "essential" hypertension. If the hypertension occurs as a result of another condition, it is called "secondary" hypertension. Primary hypertension can result from multiple factors, including blood plasma volume, activity of the hormones that regulate of blood volume and pressure, and environmental factors, such as stress and lack of exercise. Secondary hypertension has specific causes and is a complication of another problem (e.g., diabetes, due to both kidney problems and nerve damage, kidney disease, pheochromocytoma (a rare cancer of an adrenal gland), Cushing syndrome (which can be caused by corticosteroid drugs), congenital adrenal hyperplasia (disorder of the cortisol-secreting adrenal glands), hyperthyroidism (overactive thyroid gland), hyperparathyroidism (which affects calcium and phosphorous levels), pregnancy, sleep apnea, obesity, and/or chronic kidney disease (CKD).

As used herein "heart rate" (HR) refers to the speed of the heartbeat measured by the number of contractions of the heart per minute (bpm). The heart rate can vary according to the body's physical needs, including the need to absorb oxygen and excrete carbon dioxide. It is usually equal or close to the pulse measured at any peripheral point. Activities that can provoke change include physical exercise, sleep, anxiety, stress, illness, and ingestion of drugs. Many sources cite the normal resting adult human heart rate as ranging from 60-100 bpm (see, e.g., "Target Heart Rates". American Heart Association. 4 Apr. 2014). Tachycardia is a fast heart rate, defined as above 100 bpm at rest (see, e.g., "Tachycardia, Fast Heart Rate". American Heart Association. 2 May 2013). Bradycardia is a slow heart rate, defined as below 60 bpm at rest. Several studies, as well as expert consensus indicates that the normal resting adult heart rate is probably closer to a range between 50 and 90 bpm (see, e.g., Aladin, et al., The American Journal of Cardiology. 114 (11): 1701-06 (2014 Dec. 1); Hjalmarson, A., et al., The American Journal of Cardiology. 65 (9): 547-53 (1990 Mar. 1); Spodick, D. H., The American Journal of Cardiology. 72 (5): 487-88 (1993 Aug. 15); and Mason, Jay W. et al., Journal of Electrocardiology. 40 (3): 228-34 (2007 Jul. 1).

As used herein, "fractional shortening" (FS) is the reduction of the length of the end-diastolic diameter, or fraction of any diastolic dimension, that occurs by the end of or is lost in the systole.

As used herein, "arterial blood pressure" in the larger vessels consists of several distinct components: systolic and diastolic pressures, pulse pressure, and mean arterial pressure.

When "systemic arterial blood pressure" (SAP) is measured, it is recorded as a ratio of two numbers (e.g., 120/80 is a normal adult blood pressure), expressed as systolic pressure over diastolic pressure. The systolic pressure is the higher value (typically around 120 mm Hg) and reflects the arterial pressure resulting from the ejection of blood during ventricular contraction, or systole. The "diastolic arterial blood pressure" (DAP) is the lower value (usually about 80 mm Hg) and represents the arterial pressure of blood during ventricular relaxation, or diastole.

As used herein, "mean arterial pressure" (MAP) refers to an average blood pressure in an individual during a single cardiac cycle, that is, the average force driving blood into vessels that serve the tissues (see, e.g., Zheng L, et al. (July 2008), Stroke. 39 (7): 1932-7). Mean is a statistical concept and is calculated by taking the sum of the values divided by the number of values. Although complicated to measure directly and complicated to calculate, MAP can be approximated by adding the diastolic pressure to one-third of the pulse pressure or systolic pressure minus the diastolic pressure. Normally, the MAP falls within the range of 70-110 mm Hg. If the value falls below 60 mm Hg for an extended time, blood pressure will not be high enough to ensure circulation to and through the tissues, which results in ischemia, or insufficient blood flow. A condition called hypoxia, inadequate oxygenation of tissues, commonly accompanies ischemia. The term hypoxemia refers to low levels of oxygen in systemic arterial blood. Neurons are especially sensitive to hypoxia and may die or be damaged if blood flow and oxygen supplies are not quickly restored.

As used herein, "pulse pressure" (PP) refers to the difference between the measured systolic and diastolic pressures. The up and down fluctuation of the arterial pressure results from the pulsatile nature of the cardiac output, i.e., the heartbeat. Pulse pressure is determined by the interaction of the stroke volume of the heart, the compliance (ability to expand) of the arterial system and the resistance to flow in the arterial tree. By expanding under pressure, the aorta absorbs some of the force of the blood surge from the heart during a heartbeat. In this way, the pulse pressure is reduced from what it would be if the aorta were not compliant. The loss of arterial compliance that occurs with aging explains the elevated pulse pressures found in elderly patients.

"Ventricular pressure" is a measure of blood pressure within the ventricles of the heart. The pressure generated in the ventricular chambers of the heart can be measured and used in a variety of ways to understand changes in cardiac function. "Left ventricular pressure" (LVP) in conjunction with ventricular volume measurements has a history of being used to characterize the pressure-volume relationship in the beating heart. In addition, LVP is studied to ensure drugs developed do not negatively alter cardiac contractility. Left ventricular dP/dt is the first derivative of LVP, which is computed by software algorithms using calculus. Its peak value, $dP/dt_{max}$, is a common, robust and sensitive indicator of changes in cardiac contractility if experimental parameters such as preload, afterload and heart rate are well controlled.

As used herein, cardiac "contractility" is an intrinsic property of the heart muscle that affects the heart's performance and can be modified by the autonomic system, circulating hormones, drugs and disease. Evaluation of a drug's effects on contractility is important in safety assessment studies, since either an increase or a decrease may be harmful under certain clinical situations. An increase in contractility dramatically increases the heart's energy consumption, which translates to increased oxygen consumption and increased coronary blood flow. This can have serious consequences in the presence of heart disease and/or coronary insufficiency. A decrease in contractility in an already diseased heart can exacerbate the symptoms and consequences of clinical heart failure.

The methods of treatment described herein employ administration to a subject (such as a human) an NPP1 protein, active fragments or fusion protein as described herein, in order to cure, delay, reduce the severity of, or ameliorate one or more symptoms of a cardiovascular disorder, or to prolong the survival of a subject beyond that expected in the absence of such treatment.

The term "treating" includes the application or administration of the NPP1 proteins, active fragments and fusion proteins of the invention to a subject, or application or administration of NPP1 proteins, active fragments and fusion proteins of the invention to a subject who has a cardiovascular disorder, such as hypertension, with the purpose of curing, healing, alleviating, relieving, altering, remedying, ameliorating, preventing, improving, or affecting the cardiovascular disease or disorder. The term "treating" refers to any indicia of success in the treatment or amelioration of an injury, pathology or condition, including any objective or subjective parameter such as abatement; remission; diminishing of symptoms or making the injury, pathology or condition more tolerable to the subject; slowing in the rate of degeneration or decline; making the final point of degeneration less debilitating; or improving a subject's physical or mental well-being. Treatment may be therapeutic or prophylactic. The treatment or amelioration of symptoms can be based on objective or subjective parameters; including the results of a physical examination.

1. Methods of Treatment

The present invention relates to uses of an isolated recombinant human soluble NPP1 ("sNPP1") which lacks an N-terminal portion (i.e., lacking cytosolic and transmembrane domains) and fusion proteins thereof for the treatment of a cardiovascular disorder, such as hypertension.

In one embodiments, methods for improving cardiovascular function in a human patient are provided, the method comprising administering to the patient one or more doses of a recombinant human soluble ectonucleotide pyrophosphatase phosphodiesterase (hsNPP1), active fragment or fusion protein thereof.

In one embodiment, the improvement is a reduction in elevated blood pressure (e.g., reduction of blood pressure higher than 140 over 90 millimeters of mercury (mmHg) to within a normal blood pressure range (about 120 over 80 mm of mercury (mmHg)). In another embodiment, the improvement is a reduction in elevated blood pressure by at least 5 (e.g., at least 10, 15, 20, 25, 30, 35, 40, 45, 50, 55, 60, 65, or 70)%. In another embodiment, the improvement is a reduction in elevated blood pressure by about 1.5-fold, 2-fold, 2.5-fold, 3-fold, 3.5-fold, or 4-fold. In another embodiment, the improvement is a normalization of blood pressure (e.g., to about 120 over 80 mm of mercury (mmHg)). In another embodiment, the improvement is a reduction in left ventricular end-diastolic pressure (EDP) and end-systolic pressure (ESP) (e.g., by at least 5, 10, 15, 20, 25, 30, 35, 40, 45, 50, 55, 60, 65, or 70%). In another embodiment, the improvement is a reduction in left ventricular EDP and ESP by about 1.5-fold, 2-fold, 2.5-fold, 3-fold, 3.5-fold, or 4-fold. In another embodiment, the improvement is a reduction in ventricle stiffness (EDPVR) (e.g., by at least 5, 10, 15, 20, 25, 30, 35, 40, 45, 50, 55, 60, 65, or 70%). In another embodiment, the improvement is a reduction in ventricle stiffness by about 1.5-fold, 2-fold, 2.5-fold, 3-fold, 3.5-fold, or 4-fold. In another embodiment, the improvement is in increase in contractility (PRSW) (e.g., by at least 5, 10, 15, 20, 25, 30, 35, 40, 45, 50, 55, 60, 65, or 70%). In another embodiment, the improvement is in increase in contractility by about 1.5-fold, 2-fold, 2.5-fold, 3-fold, 3.5-fold, or 4-fold.

In another embodiment, methods for treating a human patient having a cardiovascular disorder are provided, the method comprising administering to the patient one or more doses of a recombinant human soluble ectonucleotide pyrophosphatase phosphodiesterase (hsNPP1), active fragment or fusion protein thereof. Exemplary cardiovascular diseases include, but are not limited to, coronary artery diseases (CAD) (such as angina and myocardial infarction (commonly known as a heart attack), stroke, heart failure, hypertensive heart disease, rheumatic heart disease, cardiomyopathy, heart arrhythmia, congenital heart disease, valvular heart disease, carditis, aortic aneurysms, peripheral artery disease, thromboembolic disease, and venous thrombosis.

In another embodiment, methods for treating a human patient having hypertension are provided, the method comprising administering to the patient one or more doses of a recombinant human soluble ectonucleotide pyrophosphatase phosphodiesterase (hsNPP1), active fragment or fusion protein thereof.

In another embodiment, methods of treating a human patient having hypertension are provided, the method comprising: a) identifying a human patient as having hypertension and b) administering to the identified patient one or more doses of a recombinant human soluble ectonucleotide pyrophosphatase phosphodiesterase (hsNPP1), active fragment or fusion protein thereof.

In another embodiment, methods for reducing hypertension in a human patient are provided, the method comprising administering to the patient one or more doses of a recombinant human soluble ectonucleotide pyrophosphatase phosphodiesterase (hsNPP1), active fragment or fusion protein thereof.

In another embodiment, the methods described herein result in a reduction in the patient's blood pressure (e.g., from an elevated blood pressure higher than about 140 over 90 millimeters of mercury (mmHg) to within a normal blood pressure range (about 120 over 80 mm of mercury (mmHg)). In another embodiment, the patient's blood pressure is reduced by at least 5 (e.g., at least 10, 15, 20, 25, 30, 35, 40, 45, 50, 55, 60, 65, or 70)% after treatment. In another embodiment, the patient's blood pressure is reduced by about 1.5-fold, 2-fold, 2.5-fold, 3-fold, 3.5-fold, or 4-fold after treatment. In another embodiment, the patient's blood pressure is normalized after treatment (e.g., to about 120 over 80 mm of mercury (mmHg)).

Generally, the dosage of fusion protein administered to a subject will vary depending upon known factors such as age, health and weight of the recipient, type of concurrent treatment, frequency of treatment, and the like. Usually, a dosage of active ingredient (i.e., fusion protein) can be between about 0.0001 and about 50 milligrams per kilogram of body weight. Precise dosage, frequency of administration and time span of treatment can be determined by a physician skilled in the art of administration of therapeutic proteins.

As defined herein, a therapeutically effective amount of protein (i.e., an effective dosage) ranges from about 0.001 to 50 mg/kg body weight. The skilled artisan will appreciate that certain factors may influence the dosage required to effectively treat a subject, including but not limited to the severity of the disease, previous treatments, the general health and/or age of the subject, and other diseases present. Moreover, treatment of a subject with a therapeutically effective amount of protein can include a single treatment or, preferably, can include a series of treatments. It will also be appreciated that the effective dosage of protein used for treatment may increase or decrease over the course of a particular treatment.

As defined herein, a therapeutically effective amount of protein or polypeptide (i.e., an effective dosage) ranges from about 0.001 to 50 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. In one embodiment, the hsNPP1 is administered in one or more doses containing about 0.1 mg/kg, 0.2 mg/kg, 0.3 mg/kg, 0.4 mg/kg, 0.5 mg/kg, 1.0 mg/kg, 2.0 mg/kg, 3.0 mg/kg, 4.0 mg/kg, 5.0 mg/kg, 6.0 mg/kg, 7.0 mg/kg, 8.0 mg/kg, 9.0 mg/kg, 10.0 mg/kg, 11.0 mg/kg, 12.0 mg/kg, 13.0 mg/kg, 14.0 mg/kg, 15.0 mg/kg, 16.0 mg/kg, 17.0 mg/kg, 18.0 mg/kg, 19.0 mg/kg, 20.0 mg/kg, 21.0 mg/kg, 22.0 mg/kg, 23.0 mg/kg, 24.0 mg/kg, 25.0 mg/kg, 26.0 mg/kg, 27.0 mg/kg, 28.0 mg/kg, 29.0 mg/kg, 30.0 mg/kg, 31.0 mg/kg, 32.0 mg/kg, 33.0 mg/kg, 34.0 mg/kg, 35.0 mg/kg, 36.0 mg/kg, 37.0 mg/kg, 38.0 mg/kg, 39.0 mg/kg, 40.0 mg/kg, 41.0 mg/kg, 42.0 mg/kg, 43.0 mg/kg, 44.0 mg/kg, or 45.0 mg/kg. In another embodiment, about 0.5 to about 30 mg, about 0.5 to about 20 mg, about 0.5 to about 10 mg, or about 0.5 to about 5 mg are administered to the patient. In another embodiment, the hsNPP1 is administered in one or more doses containing about 1.0 mg/kg to about 5.0 mg/kg hsNPP1. In another embodiment, the hsNPP1 is administered in one or more doses containing about 1.0 mg/kg to about 10.0 mg/kg hsNPP1. The skilled artisan will appreciate that certain factors may influence the dosage required to effectively treat a subject, including, but not limited to, the severity of the disease or disorder, previous treatments, the general health and/or age of the subject, and other diseases present.

Moreover, treatment of a subject with a therapeutically effective amount of a protein, polypeptide, or antibody can include a single treatment or, preferably, can include a series of treatments. In one embodiment, in the range of between about 0.1 to 20 mg/kg body weight, one time per week, twice per week, once in about 10 days, once in about 12 days, once in about 14 days, once in about 17 days, once in about 20 days, once in about 25 days, or once in about 30 days. In one embodiment, the time period between doses of the hsNPP1 is at least 2 days and can be longer, for example at least 3 days, at least 1 week, 2 weeks or 1 month. In another embodiment, the therapeutically effective dose of sNPP1, biologically active fragment or fusion protein thereof is administered to a patient between one time every 5 days and one time every 30 days for a period of time determined by a practitioner of skill in the art of medical sciences. In another embodiment, the period of time will be the remainder of the patient's life span. In another embodiment, the dosing frequency is between one time every 5 days and one time every 25 days. In another embodiment, the dosing frequency is between one time every 5 days and one time every 21 days. In another embodiment, the dosing frequency is between one time every 7 days and one time every 14 days. hsNPP1, biologically active fragment or fusion protein thereof can be administered one time every 5 days, one time every 6 days, one time every 7 days, one time every 8 days, one time every 9 days, one time every 10 days, one time every 11 days, one time every 12 days, one time every 13 days, or one time every 14 days. In some embodiments, hsNPP1, biologically active fragment or fusion protein thereof is administered about weekly. In other embodiments, sNPP1, biologically active fragment or fusion protein thereof is administered about bi-weekly. In one embodiment, the dosing frequency is one time about 30 days. It will also be appreciated that the effective dosage of soluble sNPP1 protein, biologically active fragment or fusion protein thereof used for the treatment may increase or decrease over the course of a particular treatment.

In one embodiment, about 1 mg/kg of hsNPP1, biologically active fragment or fusion protein is administered to the patient once a week. In one embodiment, about 2 mg/kg of hsNPP1, biologically active fragment or fusion protein is administered to the patient once a week. In one embodiment, about 3 mg/kg of hsNPP1, biologically active fragment or fusion protein is administered to the patient once a week. In one embodiment, about 4 mg/kg of sNPP1, biologically active fragment or fusion protein is administered to the patient once a week. In one embodiment, about 5 mg/kg of hsNPP1, biologically active fragment or fusion protein is administered to the patient once a week. In one embodiment, about 6 mg/kg of hsNPP1, biologically active fragment or fusion protein is administered to the patient once a week. In one embodiment, about 7 mg/kg of hsNPP1, biologically active fragment or fusion protein is administered to the patient once a week. In one embodiment, about 8 mg/kg of hsNPP1, biologically active fragment or fusion protein is administered to the patient once a week. In one embodiment, about 9 mg/kg of hsNPP1, biologically active fragment or fusion protein is administered to the patient once a week. In one embodiment, about 10 mg/kg of hsNPP1, biologically active fragment or fusion protein is administered to the patient once a week.

hsNPP1, biologically active fragment or fusion protein can be administered by, for example, subcutaneous injections, intramuscular injections, and intravenous (IV) infusions or injections.

In one embodiment, hsNPP1, biologically active fragment or fusion protein is administered intravenously by IV infusion by any useful method. In one example, hsNPP1, biologically active fragment or fusion protein can be administered by intravenous infusion through a peripheral line. In another example, hsNPP1, biologically active fragment or fusion protein can be administered by intravenous infusion through a peripherally inserted central catheter.

In another embodiment, hsNPP1, biologically active fragment or fusion protein is administered intravenously by IV injection. In another embodiment, hsNPP1, biologically active fragment or fusion protein is administered via intraperitoneal injection. In another embodiment, hsNPP1, biologically active fragment or fusion protein is administered by subcutaneous injections. In another embodiment, hsNPP1, biologically active fragment or fusion protein is administered by intramuscular injections.

In still another embodiment, hsNPP1, biologically active fragment or fusion protein is administered via a pharmaceutically acceptable capsule of the therapeutic protein. For example, the capsule can be an enteric-coated gelatin capsule.

In one embodiment, the method involves administering the soluble NPP1 protein or NPP1 fusion protein of the invention alone, or in combination with other agent(s). Exemplary therapeutic agents include, but are not limited to a thiazide diuretic (e.g., hydrochlorothiazide (Microzide) or chlorthalidone), a beta blocker (e.g., acebutolol (Sectral) or atenolol (Tenormin)), an angiotensin-converting enzyme (ACE) inhibitor (e.g., lisinopril (Zestril), benazepril (Lotensin), or captopril (Capoten)), an angiotensin II receptor blocker (ARB) (e.g., candesartan (Atacand) or losartan (Cozaar)), a calcium channel blocker (e.g., amlodipine (Norvasc) or diltiazem (Cardizem)), a renin inhibitor (e.g., Aliskiren (Tekturna)), an alpha blocker (e.g., doxazosin (Cardura) or prazosin (Minipress)), an alpha-beta blocker (e.g., carvedilol (Coreg) or labetalol (Trandate)), a central-acting agent (e.g., clonidine (Catapres, Kapvay), guanfacine (Intuniv, Tenex) and methyldopa), a vasodilator (e.g., hydralazine and minoxidil), and/or an aldosterone antagonist (e.g., spironolactone (Aldactone) or eplerenone (Inspra)).

In one embodiment, the isolated sNPP1 proteins, fragments, and fusion proteins can be administered before, after or concurrently with the agent or can be co-administered with other known therapies. Co-administration of the isolated sNPP1 proteins, fragments, and fusion proteins of the present invention with other therapeutic agents may provide two agents which operate via different mechanisms which yield an increased therapeutic effect. Such co-administration can solve problems due to development of resistance to drugs.

2. sNPP1

The present invention employs soluble NPP1 (e.g., hsNPP1) that has a biologically active NPP1 domain of NPP1 (i.e., NPP1 components that contain at least one extracellular catalytic domain of naturally occurring NPP1 for the pyrophosphatase and/or phosphodiesterase activity). The soluble NPP1 proteins of the invention comprise at least the NPP1 domain essential to carry out the pyrophosphatase and/or phosphodiesterase activity.

In one embodiment, the soluble NPP1, fragment, and fusion proteins thereof can form functional homodimers or monomer. In another embodiment, a soluble NPP1 protein or NPP1 fusion protein thereof can be assayed for pyrophosphatase activity as well as the ability to increase pyrophosphate levels in vivo.

Described herein are various amino acid sequences of soluble NPP1 compounds, fusion partners and fusion proteins that are suitable for use according to the methods provided herein. SEQ ID NO:5 shows the amino acid sequences of a soluble NPP1 containing amino acids from 107 to 925 of SEQ ID NO:1. SEQ ID NO:6 shows the amino acid sequence of a soluble NPP1 containing amino acids from 187 to 925 of SEQ ID NO:1. SEQ ID NO:7 shows the amino acid sequence of the Fc region of human IgG1 including the hinge region. SEQ ID NO:8 shows the amino acid sequence of the Fc of human IgG1 including a partial hinge region. SEQ ID NO:9 shows the amino acid sequence of a NPP1-Fc fusion protein. The NPP1 component contains SEQ ID NO:5, and the Fc sequence includes the hinge region. SEQ ID NO:10 shows the amino acid sequence of a NPP1-Fc fusion protein. The soluble NPP1 contains SEQ ID NO:5, and the Fc sequence includes the partial hinge region. SEQ ID NO:1 shows the amino acid sequence of a NPP1-Fc fusion protein. The soluble NPP1 contains SEQ ID NO:6, and the Fc sequence includes the hinge region. SEQ ID NO:12 shows the amino acid sequence of a NPP1-Fc fusion protein. The soluble NPP1 contains SEQ ID NO:6, and the Fc sequence includes the partial hinge region.

Preferred soluble NPP1 proteins and NPP1 fusion proteins of the invention are enzymatically active in vivo (e.g., human). In one embodiment, the soluble protein comprises amino acid sequence having at least 60, 70, 75, 80, 85, 90, 91, 92, 93, 94, 95, 96, 97, 98, 99% sequence identity to the following sequence:

```
                                              (SEQ ID NO: 2)
PSCAKEVKSCKGRCFERTFGNCRCDAACVELGNCCLDYQETCIEPEHIWT

CNKFRCGEKRLTRSLCACSDDCKDKGDCCINYSSVCQGEKSWVEEPCESI

NEPQCPAGFETPPTLLFSLDGFRAEYLHTWGGLLPVISKLKKCGTYTKNM

RPVYPTKTFPNHYSIVTGLYPESHGIIDNKMYDPKMNASFSLKSKEKFNP

EWYKGEPIWVTAKYQGLKSGTFFWPGSDVEINGIFPDIYKMYNGSVPFEE

RILAVLQWLQLPKDERPHFYTLYLEEPDSSGHSYGPVSSEVIKALQRVDG

MVGMLMDGLKELNLHRCLNLILISDHGMEQGSCKKYIYLNKYLGDVKNIK

VIYGPAARLRPSDVPDKYYSFNYEGIARNLSCREPNQHFKPYLKHFLPKR

LHFAKSDRIEPLTFYLDPQWQLALNPSERKYCGSGFHGSDNVFSNMQALF

VGYGPGFKHGIEADTFENIEVYNLMCDLLNLTPAPNNGTHGSLNHLLKNP

VYTPKHPKEVHPLVQCPFTRNPRDNLGCSCNPSILPIEDFQTQFNLTVAE

EKIIKHETLPYGRPRVLQKENTICLLSQHQFMSGYSQDILMPLWTSYTVD

RNDSFSTEDFSNCLYQDFRIPLSPVHKCSFYKNNTKVSYGFLSPPQLNKN

SSGIYSEALLTTNIVPMYQSFQVIWRYFHDTLLRKYAEERNGVNVVSGPV

FDFDYDGRCDSLENLRQKRRVIRNQEILIPTHFFIVLTSCKDTSQTPLHC

ENLDTLAFILPHRTDNSESCVHGKHDSSWVEELLMLHRARITDVEHITGL

SFYQQRKEPVSDILKLKTHLPTFSQED
```

SEQ ID NO:2 is the amino acid sequence of a sNPP1 that contains the cysteine-rich region, catalytic region and c-terminal region.

Any desired enzymatically active form of soluble NPP1 can be used in the methods described herein. The enzymatically active sNPP1 can increase pyrophosphate (PPi) levels in suitable enzymatic assays, and can be assayed for pyrophosphatase activity, phosphodiesterase activity, or pyrophosphatase and phosphodiesterase activity. Typically, the sNPP1 contains at least an NPP1 component that lacks the N-terminal cytosolic and transmembrane domains of naturally occurring transmembrane NPP1.

SEQ ID NO:1 is the amino acid sequence of wild-type NPP1 protein. The cytosolic and transmembrane regions are underlined. The potential N-glycosylation sites are in bold. The amino acid motif "PSCAKE" (SEQ ID NO:17) in bold is the start of a soluble NPP1 which includes the cysteine rich region.

In preferred aspects, the NPP1 component contains the cysteine-rich region (amino acids 99-204 of SEQ ID NO:1) and the catalytic region (amino acids 205-591 of SEQ ID NO:1) of naturally occurring human NPP1. Typically, the NPP1 component also includes the C-terminal region (amino acids 592 to 925 of SEQ ID NO:1), and has the amino acid sequence of SEQ ID NO:2. However, the C-terminal region can be truncated if desired. Accordingly, preferred NPP1 components include the cysteine-rich region and catalytic region of human NPP1 (amino acids 99-591 of SEQ ID NO:1) or the cysteine-rich region, the catalytic region and the C-terminal region of human NPP1 (SEQ ID NO:2). Other preferred NPP1 components contain only a portion of the cysteine-rich domain and have the sequence of amino acids 107 to 925 of SEQ ID NO:1 or amino acids 187 to 925 of SEQ ID NO:1. The cysteine rich region of NPP1 (i.e., amino acids 99 to 204 of SEQ ID NO: 1) can facilitate dimerization of the sNPP1. The sNPP1, including fusion proteins, can be in the form of a monomer of functional homodimer.

The amino acid sequence of the NPP1 component can be a variant of the naturally occurring NPP1 sequence, provided that the NPP1 component is enzymatically active. NPP1 variants are enzymatically active and have at least 80%, at least 85%, at least 90%, at least 95% and more preferably at least 96% amino acid sequence identity to the corresponding portion of human NPP1 (e.g., over the length of the cysteine-rich region, the catalytic region, the c-terminal region, the cysteine-rich region plus the catalytic region, the cystein-rich region plus the catalytic region plus the c-terminal region. Preferred NPP1 variants have at least 90%, preferably at least 95%, more preferably at least 97% amino acid sequence identity to (i) the amino acid sequence of residues 205-591 of SEQ ID NO: 1, (ii) the amino acid sequence of residues 99-591 of SEQ ID NO:1, (iii) the amino acid sequence of residues 99-925 of SEQ ID NO:1, (iv) the amino acid sequence of residues 107-925 of SEQ ID NO:1, or (v) the amino acid sequence of residues 187-925 of SEQ ID NO:1. Suitable positions for amino acid variation are well-known from NPP1 structural studies and analysis of disease-associated mutations in NPP1. For example, substitution of the following amino acids occurs in certain disease-associated mutations that reduce NPP1 enzymatic activity, and variations of the amino acids at these positions should be avoided: Ser216, Gly242, Pro250, Gly266, Pro305, Arg349, Tyr371, Arg456, Tyr471, His500, Ser504, Tyr513, Asp538, Tyr570, Lys579, Gly586; Tyr659, Glu668, Cys726, Arg774, His777, Asn792, Asp804, Arg821, Arg888, and Tyr901. (See, e.g., Jansen, S. et al., Structure 20:1948-1959 (2012)).

In one embodiment, the soluble NPP1 protein can be a fusion protein recombinantly fused or chemically bonded (e.g., covalent bond, ionic bond, hydrophobic bond and Van der Waals force) to a fusion partner. In another embodiment, the fusion protein has at least 70, 75, 80, 85, 90, 91, 92, 93, 94, 95, 96, 97, 98, or 99% sequence identity to SEQ ID NO: 3 or SEQ ID NO:4. SEQ ID NO:4 is the amino acid sequence of sNPP1-Fc-D10 (SEQ ID NO:4). The Fc sequence is underlined.

To determine the percent identity of two amino acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., sNPP1 amino acid sequence of SEQ ID NO:2; amino acids 107-925 of SEQ ID NO:1 or amino acids 187-925 of SEQ ID NO:1). The amino acid residues or nucleotides at corresponding amino acid positions are then compared. When a position in the first sequence is occupied by the same amino acid residue or nucleotide as the corresponding position in the second sequence, then the molecules are identical at that position (as used herein amino acid is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J Mol Biol* 1970, 48, 444-453) algorithm which has been incorporated into the GAP program in the GCG software package (available at www.gcg.com), using either a Blosum 62 matrix or a PAM250 matrix, and a gap weight of 16, 14, 12, 10, 8, 6, or 4 and a length weight of 1, 2, 3, 4, 5, or 6. In another embodiment, the percent identity between two amino acid is determined using the algorithm of E. Meyers and W. Miller (CABIOS, 1989, 4, 11-17) which has been incorporated into the ALIGN program (version 2.0 or 2.0U), using a PAM120 weight residue table, a gap length penalty of 12 and a gap penalty of 4.

The sNPP1 can consist of or consist essentially of an NPP1 component as described herein. Alternatively, the sNPP1 can be in the form of a fusion protein that contains an NPP1 component and one or more other polypeptides, referred to as fusion partners, optionally through a suitable linker in each instance, or in the form of a conjugate between an NPP1 component and another molecule (e.g., PEG). When the sNPP1 is in the form of a fusion protein, each fusion partner is preferably located c-terminally to the NPP1 component. Without wishing to be bound by any particular theory, it is believed that fusion proteins that contain an NPP1 component that contains the cysteine-rich region and catalytic region, and one or more fusion proteins that are located c-terminally to the NPP1 component, are preferred over other configurations of NPP1 fusion proteins because they can be expressed at sufficient levels and are sufficiently stable to be used as therapeutic proteins.

Any suitable fusion partner can be included in the fusion protein. Advantageously, a number of fusion partners are well-known in the art that can provide certain advantages, such as reduced aggregation and immunogenicity, increased the solubility, improved expression and/or stability, and improved pharmacokinetic and/or pharmacodynamics performance. See, e.g., Strohl, W. R. *BioDrugs* 29:215-239 (2015). For example, it is well-known that albumin, albumin fragments or albumin variants (e.g., human serum albumin and fragments or variants thereof) can be incorporated into fusion proteins and that such fusion proteins can be easily purified, stable and have an improved plasma half-life. Suitable albumin, albumin fragments and albumin variants that can be used in the sNPP1 fusion proteins are disclosed, for example in WO 2005/077042A2 and WO 03/076567A2, each of which is incorporated herein by reference in its entirety. Fusions to human transferrin are also known to improve half-life. See, e.g., Kim B J et al., *J Pharmacol Expr Ther* 334(3):682-692 (2010); and WO 2000/020746. Peptides that bind to albumin or transferrin, such as antibodies or antibody fragments, can also be used. See, e.g., EP 0486525 B1, U.S. Pat. No. 6,267,964 B1, WO 04/001064A2, WO 02/076489A1, WO 01/45746, WO 2006/004603, and WO 2008/028977. Similarly immunoglobulin Fc fusion proteins are well-known. See, e.g., Czajkowsky D M et al., *EMBO Mol Med* 4(10):1015-1028 (2012), U.S. Pat. Nos. 7,902,151; and 7,858,297, the entire teachings of which are incorporated herein by reference in their entirety. The fusion protein can also include a CTP sequence (see also, Fares et al., *Endocrinol* 2010, 151, 4410-4417; Fares et al., *Proc Natl Acad Sci* 1992, 89, 4304-4308; and Furuhashi et al., *Mol Endocrinol* 1995, 9, 54-63). Preferably, the fusion partner is the Fc of an immunoglobulin (e.g., Fc or human IgG1). The Fc can include CH1, CH2 and CH3 of human IgG1, and optionally the human IgG1 hinge region (EPKSCDKTHTCPPCP (SEQ ID NO:13)) or a portion of the human IgG1 hinge region (e.g., DKTHTCPPCP (SEQ ID NO:14) or PKSCDKTHTCPPCP (SEQ ID NO:15)) if desired. In some fusion proteins, the Fc can include CH2 and CH3 of human IgG1, or the Fc of human IgG2 or human IgG4, if desired. Preferably, the sNPP1 fusion protein comprises an NPP1 component and a peptide that increases the half-life of the fusion protein, most preferably the Fc of an immunoglobulin (e.g., Fc or human IgG1). As used herein, a "protein that increases the half-life of the fusion protein" refers to a protein that, when fused to a soluble NPP1 or biologically active fragment, increases the half-life of the soluble NPP1 polypeptide or biologically active fragment as compared to the half-life of the soluble NPP1 polypeptide, alone, or the NPP1 biologically active fragment, alone. In one embodiment, the half-life of the NPP1 fusion protein is increased 50% as compared to the half-life of the NPP1 polypeptide or biologically active fragment, alone. In another embodiment, the half-life of the NPP1 fusion protein is increased 60% as compared to the half-life of the NPP1 polypeptide or biologically active fragment, alone. In another embodiment, the half-life of the NPP1 fusion protein is increased 70% as compared to the half-life of the NPP1 polypeptide or biologically active fragment, alone. In another embodiment, the half-life of the NPP1 fusion protein is increased 80% as compared to the half-life of the NPP1 polypeptide or biologically active fragment, alone. In another embodiment, the half-life of the NPP1 fusion protein is increased 90% as compared to the half-life of the NPP1 polypeptide or biologically active fragment, alone.

In another embodiment, the half-life of the NPP1 fusion protein is increased 2 fold, 3 fold, 4 fold, 5 fold, 6 fold, 7 fold, 8 fold, 9 fold, or 10 fold as compared to the half-life of the NPP1 polypeptide or biologically active fragment, alone. Methods for determining the half-life of a protein or fusion protein are well known in the art. For example, Zhou et al., Determining Protein Half-Lives, *Methods in Molecular Biology* 2004, 284, 67-77 discloses numerous methods for testing of the half-life of a protein. If desired, the fusion protein can be conjugated to polymers or other suitable compounds that extend half-life, such as polyethylene glycol (PEG), can be conjugated to the NPP1 fusion proteins.

In one embodiment, the peptide which increases the half-life of the fusion protein is a CTP sequence (see also, Fares et al., 2010, *Endocrinol.*, 151(9):4410-4417; Fares et al., 1992, *Proc. Natl. Acad. Sci*, 89(10):4304-4308; and Furuhashi et al., 1995, Molec. Endocrinol., 9(1):54-63).

In another embodiment, the peptide which increases the half-life of the fusion protein is an Fc domain of an Ig.

Fusion partners may also be selected to target the fusion protein to desired sites of clinical or biological importance (e.g., site of calcification). For example, peptides that have high affinity to the bone are described in U.S. Pat. No. 7,323,542, the entire teachings of which are incorporated herein by reference. Peptides that can increase protein targeting to calcification sites can contain a consecutive stretch of at least about 4 acidic amino acids, for example, glutamic acids or aspartic acids. Typically, the peptide that targets the fusion protein to calcification sites will comprise between 4 and 20 consecutive acidic amino acids, for example 4, 5, 6, 7, 8, 9, 10, 11, 12, 13, 14, 15, 16, 17, 18, 19 or 20 consecutive amino acids selected from glutamic acid and aspartic acid. The peptide can consist solely of glutamic acid residues, solely of aspartic acid residues, or be a mixture of glutamic acid and aspartic acid residues. A particularly preferred moiety for targeting to sights of calcification is $Asp_{10}$ (SEQ ID NO:18).

In one embodiment, the NPP1 fusion protein of the invention comprises an NPP1 polypeptide and a moiety that increase protein targeting to calcification sites such as a consecutive stretch of acidic amino acids, for example, glutamic acids or aspartic acids.

Suitable peptide linkers for use in fusion proteins are well-known and typically adopt a flexible extended conformation and do not interfere with the function of the NPP1 component or the fusion partners. Peptide linker sequences may contain Gly, His, Asn and Ser residues in any combination. The useful peptide linkers include, without limitation, poly-Gly, poly-His, poly-Asn, or poly-Ser. Other near neutral amino acids, such as Thr and Ala can be also used in the linker sequence. Amino acid sequences which can be usefully employed as linkers include those disclosed in Maratea et al., *Gene* 1985, 40, 39-46; Murphy et al., *Proc Natl Acad Sci USA* 1986, 83, 8258-8262; U.S. Pat. Nos. 4,935,233 and 4,751,180. Other suitable linkers can be obtained from naturally occurring proteins, such as the hinge region of an immunoglobulin. A preferred synthetic linker is $(Gly_4Ser)_n$, where n is 1, 2, 3, 4, 5, 6, 7, 8, 9 or 10 (SEQ ID NO:19). Preferably, n is 3 or 4. For example, in some embodiments the linker is $(Gly_4Ser)_3$ (SEQ ID NO:16) and the fusion protein include a linker with the amino acid sequence GlyGlyGlyGlySerGlyGlyGlyGlySerGlyGlyGlyGlySer (SEQ ID NO:16). Typically, the linker is from 1 to about 50 amino acid residues in length, or 1 to about 25 amino acids in length. Frequently, the linker is between about 8 and about 20 amino acids in length.

Preferred NPP1 fusion proteins comprise from N-terminus to C-terminus an NPP1 component, optionally a linker, an Fc region of an immunoglobulin (e.g., human IgG1 Fc optionally including hinge or a portion thereof), optionally a second liner, and optionally a targeting moiety. Thus, the Fc region and the optional targeting moiety, when present, are each located C-terminally to the NPP1 component. The NPP1 component preferably comprises the cysteine-rich region and the catalytic domain of NPP1, lacks the N-terminal cytosolic and transmembrane domains, and optionally contains the C-terminal region.

A preferred fusion protein comprises, from N-terminus to C-terminus, an NPP1 component comprising the cysteine-rich domain, the catalytic domain and the C-terminal region of human NPP1; and the Fc region, including hinge, of a human immunoglobulin. Preferably, the Fc region is from human IgG1. In particular embodiments, the fusion protein has at least 80%, at least 85%, at least 90%, at least 91%, at least 92%, at least 93%, at least 94%, at least 95%, at least 96%, at least 97%, at least 98%, or at least 99% sequence identity to SEQ ID NO:3. SEQ ID NO:3 is the amino acid sequence of sNPP1-Fc fusion protein.

A preferred fusion protein of this type has the amino acid sequence of SEQ ID NO:3.

Another preferred fusion protein comprises, from N-terminus to C-terminus, an NPP1 component comprising the cysteine-rich domain, the catalytic domain and the C-terminal region of human NPP1; a linker (e.g., $(Gly_4Ser)_3$ (SEQ ID NO:16)); and the Fc region, including hinge, of a human immunoglobulin. Preferably, the Fc region is from human IgG1.

Another preferred fusion protein comprises, from N-terminus to C-terminus, an NPP1 component comprising the cysteine-rich domain, the catalytic domain and the c-terminal region of human NPP1; the Fc region, including hinge or a portion thereof, of a human immunoglobulin; and a moiety targeting the fusion protein to sites of calcification. Preferably, the Fc region is from human IgG1. Preferably, the moiety targeting the fusion protein to sites of calcification is $Asp_{10}$ (SEQ ID NO:18). More preferably, the Fc region is from human IgG1 and the moiety targeting the fusion protein to sites of calcification is $Asp_{10}$ (SEQ ID NO:18). In particular embodiments, the fusion protein has at least 80%, at least 85%, at least 90%, at least 91%, at least 92%, at least 93%, at least 94%, at least 95%, at least 96%, at least 97%, at least 98%, or at least 99% sequence identity to SEQ ID NO:4. A preferred fusion protein of this type has the amino acid sequence of SEQ ID NO:4.

Another preferred fusion protein comprises, from N-terminus to C-terminus, an NPP1 component comprising the cysteine-rich domain, the catalytic domain and the c-terminal region of human NPP1; a linker (e.g., $(Gly_4Ser)_3$ (SEQ ID NO:16)); the Fc region, including hinge or a portion thereof, of a human immunoglobulin; and a moiety targeting the fusion protein to sites of calcification. Preferably, the Fc region is from human IgG1. Preferably, the moiety targeting the fusion protein to sites of calcification is $Asp_{10}$ (SEQ ID NO:18). More preferably, the Fc region is from human IgG1 and the moiety targeting the fusion protein to sites of calcification is $Asp_{10}$ (SEQ ID NO:18).

Another preferred fusion protein comprises, from N-terminus to C-terminus, an NPP1 component comprising a portion of the cysteine-rich domain, the catalytic domain and the c-terminal region of human NPP1; optionally a linker (e.g., $(Gly_4Ser)_3$ (SEQ ID NO:16)); the Fc region, including hinge or a portion thereof, of a human immunoglobulin. Preferably, the Fc region is from human IgG1. In particular embodiments, the fusion protein has at least 80%, at least 85%, at least 90%, at least 91%, at least 92%, at least 93%, at least 94%, at least 95%, at least 96%, at least 97%, at least 98%, or at least 99% sequence identity to SEQ ID NO:9, SEQ ID NO:10, SEQ ID NO:11, or SEQ ID NO:12.

Preferred fusion protein of this type have the amino acid sequence of SEQ ID NO:9, SEQ ID NO:10, SEQ ID NO:11 or SEQ ID NO:12. In particularly preferred aspects, a fusion protein of SEQ ID NO:3 is administered in accordance with the methods described herein. In other particularly preferred aspect, a fusion protein of SEQ ID NO:4 is administered in accordance with in the methods described herein. In other particularly preferred aspect, a fusion protein of SEQ ID NO:9 is administered in accordance with in the methods described herein. In other particularly preferred aspect, a fusion protein of SEQ ID NO:10 is administered in accordance with the methods described herein. In other particularly preferred aspect, a fusion protein of SEQ ID NO:11 is administered in accordance with the methods described herein. In other particularly preferred aspect, a fusion protein of SEQ ID NO:12 is administered in accordance with the methods described herein.

Fusion proteins of the present invention can be prepared using standard methods, including recombinant techniques or chemical conjugation well known in the art. Techniques useful for isolating and characterizing the nucleic acids and proteins of the present invention are well known to those of skill in the art and standard molecular biology and biochemical manuals can be consulted to select suitable protocols for use without undue experimentation. See, for example, Sambrook et al., 1989, "Molecular Cloning: A Laboratory Manual", $2^{nd}$ ed., Cold Spring Harbor, the content of which is herein incorporated by reference in its entirety. The isolated recombinant human sNPP1, fragment, and fusion proteins thereof, can be produced in any useful protein expression system including, without limitation, cell culture (e.g., CHO cells, COS cells, HEK203), bacteria such as *Escherichia coli* (*E. coli*) and transgenic animals, including, but no limited to, mammals and avians (e.g., chickens, quail, duck and turkey). For expression, a construct that encodes the sNPP1 and includes a suitable signal sequence (e.g, from human Ig heavy chain, NPP2, NPP4, NPP7 or human serum albumin, for example) in frame with the sequence of the sNPP1 and operably linked to suitable expression control elements.

The sNPP1, including the fusion proteins, and physiologically acceptable salt forms thereof are typically formulated into a pharmaceutical composition for administration in accordance with the methods described herein. Pharmaceutical compositions typically include a pharmaceutically acceptable carrier or excipient. Compositions comprising such carriers, including composite molecules, are formulated by well-known conventional methods (see, for example, Remington's Pharmaceutical Sciences, $14^{th}$ ed., Mack Publishing Co., Easton, PA), the entire teachings of which are incorporated herein by reference. The carrier may comprise a diluent. In one embodiment, the pharmaceutical carrier can be a liquid and the fusion protein may be in the form of a solution. The pharmaceutical carrier can be wax, fat, or alcohol. In another embodiment, the pharmaceutically acceptable carrier may be a solid in the form of a powder, a lyophilized powder, or a tablet. In one embodiment, the carrier may comprise a liposome or a microcapsule. The pharmaceutical compositions can be in the form of a sterile lyophilized powder for injection upon reconstitution with a diluent. The diluent can be water for injection, bacteriostatic water for injection, or sterile saline. The lyophilized powder may be produced by freeze drying a solution of the fusion protein to produce the protein in dry form. As is known in the art, the lyophilized protein generally has increased stability and a longer shelf life than a liquid solution of the protein.

EQUIVALENTS

Those skilled in the art will recognize, or be able to ascertain using no more than routine experimentation, many equivalents of the specific embodiments described herein. Such equivalents are intended to be encompassed by the following claims. Any combination of the embodiments disclosed in the any plurality of the dependent claims or Examples is contemplated to be within the scope of the disclosure.

INCORPORATION BY REFERENCE

The disclosure of each and every U.S. and foreign patent and pending patent application and publication referred to herein is specifically incorporated herein by reference in its entirety, as are the contents of Sequence Listing and Figures.

EXAMPLES

The present invention is further exemplified by the following examples. The examples are for illustrative purpose only and are not intended, nor should they be construed as limiting the invention in any manner.

Example 1: Evaluation of hEnpp1 Treatment on Cardiovascular Hemodynamics and Function in Asj-2J Mice Experiments were conducted to determine if Enpp1 treatment improves elevated blood pressure and left ventricular hypertrophy in Asj-2J mice. Two week old Enpp1$^{asj-2J}$ mice received 2100 U/kg of hEnpp1-Fc (TSAC 2.7) every other day (EOT) subcutaneously over the course of six weeks. Vehicle-treated wild-type mice and Asj-2j mice served as controls. At seven weeks of age, the mice were shipped to third party analyst for assessment of primary and secondary outcome measures. Dosing was continued by the analyst throughout the testing period (i.e., through week 11). Primary outcome measures included: echocardiogram (cardiac dimensions, heart rate ("HR") and fractional shortening ("FS"), terminal hemodynamics (systolic arterial pressure ("SAP"), diastolic arterial pressure ("DAP"), mean arterial pressure ("MAP"), pulse pressure ("PP"), heart rate ("HR"), left ventricular pressure ("LVP")), pressure volume loops (heart compliance and contractility), and aorta and vibrissae calcification. Secondary outcome measures included Enpp1 protein, pyrophosphate (PPi), and ADAs.

Figure 2:
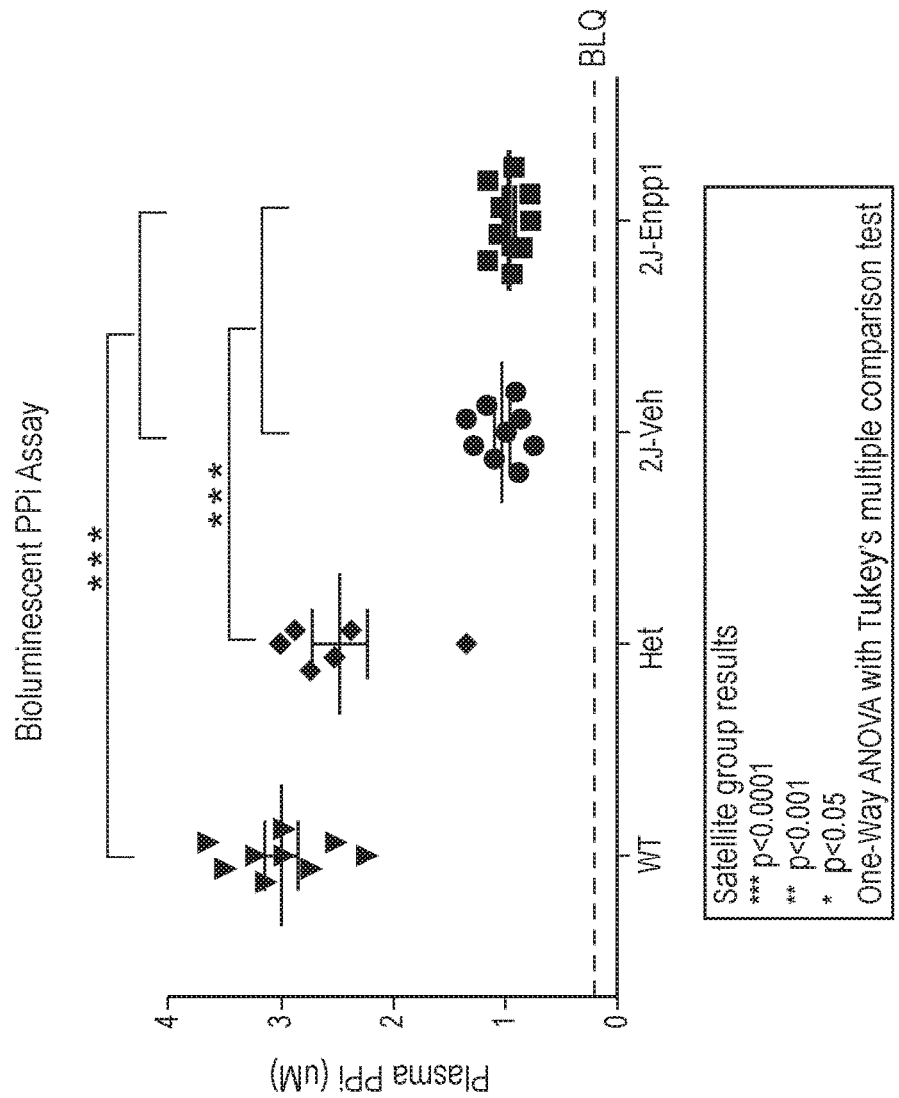
FIG. 2 shows that there was no increase in pyrophosphate (PPi) levels in ENPP1-treated 2J mice, twenty-four hours after the last dose of a six week treatment.
Figure 3C:
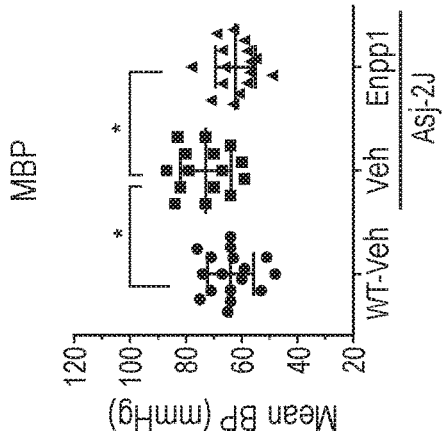
FIGS. 3A-3D show that Enpp1-treatment reduces elevated blood pressure in Asj-2J mice.
Figure 3B:
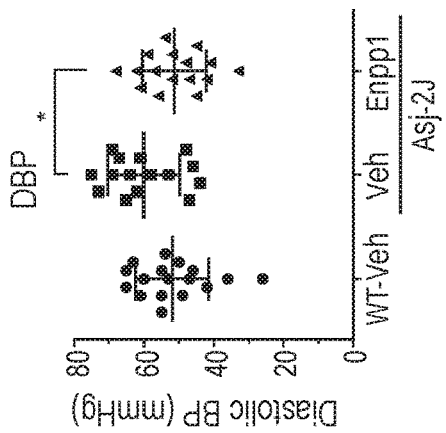
Figure 3D:
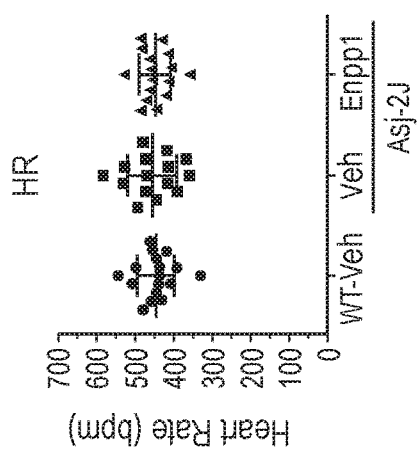
Figure 3A:
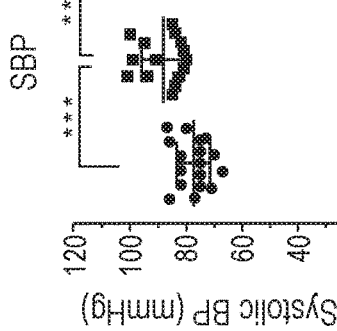
Figure 4A:
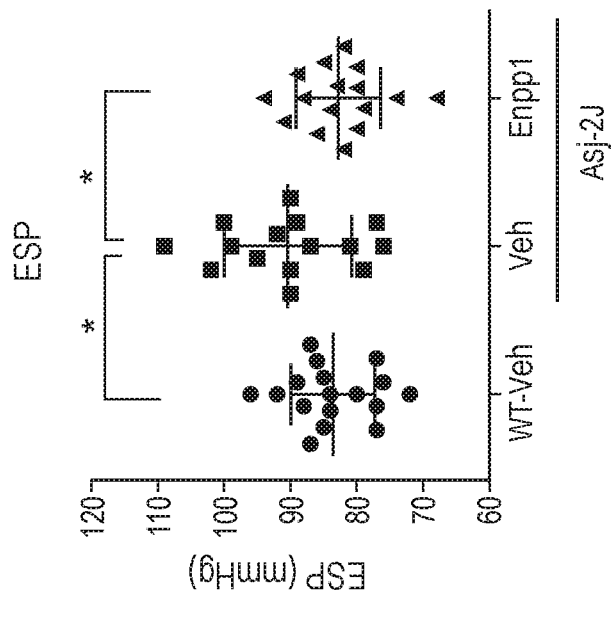
FIGS. 4A-4B show that Enpp1-treatment reduces elevated left ventricular end-diastolic pressures (EDP) and end-systolic (ESP) pressures in Asj-2J mice.
Figure 4B:
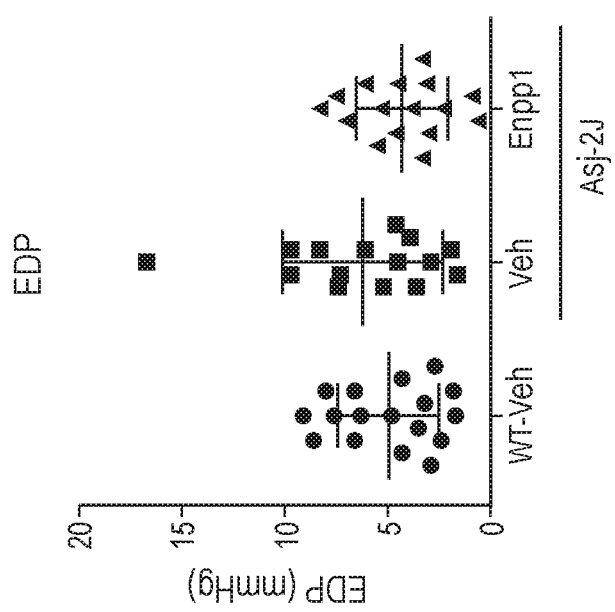

As shown in FIGS. 1A-1C, there was no reduction in calcification, no increase in plasma pyrophosphate (PPi) levels (FIG. 1D), and high plasma ADA levels (FIG. 1E) in ENPP1-treated Asj-2J mice after six weeks of treatment. As shown in FIG. 2, there was no increase in PPI levels in ENPP1-treated Asj-2J mice, twenty-four hours after the last dose of the six week treatment. However, as shown in FIGS. 3A-3D, ENPP1 treatment reduced elevated blood pressure in Asj-2J mice. In addition, as shown in FIGS. 4A-4B, ENPP1 treatment reduced elevated left ventricular end-diastolic and end-systolic pressures in ASJ-2J mice.

Pressure volume loops were used to assess intact heart function, as well as compliance (stiffness) and contractility of the heart. Pressure volume loops provide simultaneous real-time measurement of both LV pressure and LV volume during a complete cardiac cycle. "ESPVR" describes the maximum pressure that can develop in ventricle at any given LV volume (e.g., it is a measure of myocardial contractility). "EDPVR" describes the passive filling curve for the ventricle and is a measure of passive chamber stiffness (e.g., it is a measure of ventricular stiffness). "PRSW" describes the relationship between stroke work and EDV (e.g., it is a measure of myocardial contractility). As shown in FIGS. 5A-5C the pressure volume loops indicate that ENPP1 treatment reduces ventricle stiffness (EDPVR) and increases contractility (PRSW) in ASJ-2J mice.

An echocardiogram ("ECHO") is a test that uses high frequency sound waves (ultrasound) to create pictures of the heart's chambers, valves, walls and the blood vessels (aorta, arteries, veins) attached to the heart. As shown in FIGS. 6A-6J, the results of the echocardiogram suggest that Asj-2J mice do not have left ventricular hypertrophy, as there was no change in LV Diastolic Anterior/Posterior Wall Thickness, internal dimensions, End-Diastolic Area, and Estimated LV Mass.

In summary, Enpp1 treatment improved the elevated blood pressure (SBP, DBP, MBP) and left ventricular pressure observed in Asj-2J mice. HR was unaffected. The pressure volume loop data suggests that Asj-2J have increased ventricle stiffness (EDPVR) and reduced contractility (PRSW), both of which were rescued by Enpp1 treatment. ECHO analysis of Asj-2J mice (normalized to BW) indicated no change in cardiac dimensions and area, suggesting no indication of left ventricular hypertrophy. Overall, there a significant improvement in cardiovascular function was observed with Enpp1 treatment, despite no reduction in calcification This suggests that improvements in cardiovascular function could be due to calcification-independent effects, such as adenosine signaling.

Example 2: Evaluation of Feasibility of Hemodynamic Procedure in Young Asj-2J Mice It is hypothesized that if Enpp1 can improve blood pressure in 4 week old Asj-2J mice (before elevated calcification detected), Enpp1-induced improvements in blood pressure are are independent of improvements in calcification, thus suggesting a possible role of Enpp1 on adenosine signaling and myointimal proliferation. Accordingly, a pilot study is conducted to evaluate the feasibility of hemodynamic procedure in young WT and Asj-2J mice.

The primary objectives are to determine the feasibility of catheterization for the hemodynamic procedure in 4 week WT and Asj-2J mice, determine if blood pressure is elevated in 4 week old Asj-2J mice similar to 8 week old mice, and to determine if isoproterenol (b-adrenergic agonist, which increases heart rate and myocardial contractility) or phenylephrine (a-adrenergic agonist; a vasopressor that increases blood pressure, but does not affect contractility and output of cardiac muscle) challenges uncover any additional differences in responsiveness in the WT and Asj-2J mice. Primary outcome measures include: terminal hemodynamics at baseline and after isoproterenol/phenylephrine challenges (e.g., SAP, DAP, MAP, PP, HR, LVP readouts). Secondary outcome measures include ECHO as a back-up, if hemodynamics are not feasible (cardiac dimensions, HR, FS).

```
SUMMARY OF SEQUENCE LISTING
amino acid sequence of wild-type NPP1 protein
                                                  SEQ ID NO: 1
MERDGCAGGGSRGGEGGRAPREGPAGNGRDRGRSHAAEAPGDPQAAASLLAPMDVGE

EPLEKAARARTAKDPNTYKVLSLVLSVCVLTTILGCIFGLKPSCAKEVKSCKGRCFERTF

GNCRCDAACVELGNCCLDYQETCIEPEHIWTCNKFRCGEKRLTRSLCACSDDCKDKGD

CCINYSSVCQGEKSWVEEPCESINEPQCPAGFETPPTLLFSLDGFRAEYLHTWGGLLPVI

SKLKKCGTYTKNMRPVYPTKTFPNHYSIVTGLYPESHGIIDNKMYDPKMNASFSLKSKE

KFNPEWYKGEPIWVTAKYQGLKSGTFFWPGSDVEINGIFPDIYKMYNGSVPFEERILAVL

QWLQLPKDERPHFYTLYLEEPDSSGHSYGPVSSEVIKALQRVDGMVGMLMDGLKELNL

HRCLNLILISDHGMEQGSCKKYIYLNKYLGDVKNIKVIYGPAARLRPSDVPDKYYSFNYE

GIARNLSCREPNQHFKPYLKHFLPKRLHFAKSDRIEPLTFYLDPQWQLALNPSERKYCGS

GFHGSDNVFSNMQALFVGYGPGFKHGIEADTFENIEVYNLMCDLLNLTPAPNNGTHGSL

NHLLKNPVYTPKHPKEVHPLVQCPFTRNPRDNLGCSCNPSILPIEDFQTQFNLTVAEEKIIK

HETLPYGRPRVLQKENTICLLSQHQFMSGYSQDILMPLWTSYTVDRNDSFSTEDFSNCLY

QDFRIPLSPVHKCSFYKNNTKVSYGFLSPPQLNKNSSGIYSEALLTTNIVPMYQSFQVIWR

YFHDTLLRKYAEERNGVNVVSGPVFDFDYDGRCDSLENLRQKRRVIRNQEILIPTHFFIVL

TSCKDTSQTPLHCENLDTLAFILPHRTDNSESCVHGKHDSSWVEELLMLHRARITDVEHI

TGLSFYQQRKEPVSDILKLKTHLPTFSQED amino acid sequence of sNPP1 that contains cysteine-rich region,
catalytic region and c-terminal region
                                                  SEQ ID NO: 2
PSCAKEVKSCKGRCFERTFGNCRCDAACVELGNCCLDYQETCIEPEHIWTCNKFRCGEK

RLTRSLCACSDDCKDKGDCCINYSSVCQGEKSWVEEPCESINEPQCPAGFETPPTLLFSL

DGFRAEYLHTWGGLLPVISKLKKCGTYTKNMRPVYPTKTFPNHYSIVTGLYPESHGIIDN
```

-continued

KMYDPKMNASFSLKSKEKFNPEWYKGEPIWVTAKYQGLKSGTFFWPGSDVEINGIFPDI

YKMYNGSVPFEERILAVLQWLQLPKDERPHFYTLYLEEPDSSGHSYGPVSSEVIKALQR

VDGMVGMLMDGLKELNLHRCLNLILISDHGMEQGSCKKYIYLNKYLGDVKNIKVIYGP

AARLRPSDVPDKYYSFNYEGIARNLSCREPNQHFKPYLKHFLPKRLHFAKSDRIEPLTFY

LDPQWQLALNPSERKYCGSGFHGSDNVFSNMQALFVGYGPGFKHGIEADTFENIEVYN

LMCDLLNLTPAPNNGTHGSLNHLLKNPVYTPKHPKEVHPLVQCPFTRNPRDNLGCSCNP

SILPIEDFQTQFNLTVAEEKIIKHETLPYGRPRVLQKENTICLLSQHQFMSGYSQDILMPL

WTSYTVDRNDSFSTEDFSNCLYQDFRIPLSPVHKCSFYKNNTKVSYGFLSPPQLNKNSSG

IYSEALLTTNIVPMYQSFQVIWRYFHDTLLRKYAEERNGVNVVSGPVFDFDYDGRCDSL

ENLRQKRRVIRNQEILIPTHFFIVLTSCKDTSQTPLHCENLDTLAFILPHRTDNSESCVHGK

HDSSWVEELLMLHRARITDVEHITGLSFYQQRKEPVSDILKLKTHLPTFSQED amino acid sequence of sNPP1-Fc fusion protein
SEQ ID NO: 3
PSCAKEVKSCKGRCFERTFGNCRCDAACVELGNCCLDYQETCIEPEHIWTCNKFRCGEK

RLTRSLCACSDDCKDKGDCCINYSSVCQGEKSWVEEPCESINEPQCPAGFETPPTLLFSL

DGFRAEYLHTWGGLLPVISKLKKCGTYTKNMRPVYPTKTFPNHYSIVTGLYPESHGIIDN

KMYDPKMNASFSLKSKEKFNPEWYKGEPIWVTAKYQGLKSGTFFWPGSDVEINGIFPDI

YKMYNGSVPFEERILAVLQWLQLPKDERPHFYTLYLEEPDSSGHSYGPVSSEVIKALQR

VDGMVGMLMDGLKELNLHRCLNLILISDHGMEQGSCKKYIYLNKYLGDVKNIKVIYGP

AARLRPSDVPDKYYSFNYEGIARNLSCREPNQHFKPYLKHFLPKRLHFAKSDRIEPLTFY

LDPQWQLALNPSERKYCGSGFHGSDNVFSNMQALFVGYGPGFKHGIEADTFENIEVYN

LMCDLLNLTPAPNNGTHGSLNHLLKNPVYTPKHPKEVHPLVQCPFTRNPRDNLGCSCNP

SILPIEDFQTQFNLTVAEEKIIKHETLPYGRPRVLQKENTICLLSQHQFMSGYSQDILMPL

WTSYTVDRNDSFSTEDFSNCLYQDFRIPLSPVHKCSFYKNNTKVSYGFLSPPQLNKNSSG

IYSEALLTTNIVPMYQSFQVIWRYFHDTLLRKYAEERNGVNVVSGPVFDFDYDGRCDSL

ENLRQKRRVIRNQEILIPTHFFIVLTSCKDTSQTPLHCENLDTLAFILPHRTDNSESCVHGK

HDSSWVEELLMLHRARITDVEHITGLSFYQQRKEPVSDILKLKTHLPTFSQED<u>PKSCDKT</u>

<u>HTCPPCPAPEAAGAPSVFLFPPKPKDTLMISRTPEVTCVVVDVSHEDPEVKFNWYVDGV</u>

<u>EVHNAKTKPREEQYNSTYRVVSVLTVLHQDWLNGKEYKCKVSNKALPAPIEKTISKAK</u>

<u>GQPREPQVYTLPPSREEMTKNQVSLTCLVKGFYPSDIAVEWESNGQPENNYKTTPPVLD</u>

<u>SDGSFFLYSKLTVDKSRWQQGNVFSCSVMHEALHNHYTQKSLSLSPGK</u> amino acid sequence of sNPP1-Fc-D10
SEQ ID NO: 4
PSCAKEVKSCKGRCFERTFGNCRCDAACVELGNCCLDYQETCIEPEHIWTCNKFRCGEK

RLTRSLCACSDDCKDKGDCCINYSSVCQGEKSWVEEPCESINEPQCPAGFETPPTLLFSL

DGFRAEYLHTWGGLLPVISKLKKCGTYTKNMRPVYPTKTFPNHYSIVTGLYPESHGIIDN

KMYDPKMNASFSLKSKEKFNPEWYKGEPIWVTAKYQGLKSGTFFWPGSDVEINGIFPDI

YKMYNGSVPFEERILAVLQWLQLPKDERPHFYTLYLEEPDSSGHSYGPVSSEVIKALQR

VDGMVGMLMDGLKELNLHRCLNLILISDHGMEQGSCKKYIYLNKYLGDVKNIKVIYGP

AARLRPSDVPDKYYSFNYEGIARNLSCREPNQHFKPYLKHFLPKRLHFAKSDRIEPLTFY

LDPQWQLALNPSERKYCGSGFHGSDNVFSNMQALFVGYGPGFKHGIEADTFENIEVYN

LMCDLLNLTPAPNNGTHGSLNHLLKNPVYTPKHPKEVHPLVQCPFTRNPRDNLGCSCNP

SILPIEDFQTQFNLTVAEEKIIKHETLPYGRPRVLQKENTICLLSQHQFMSGYSQDILMPL

WTSYTVDRNDSFSTEDFSNCLYQDFRIPLSPVHKCSFYKNNTKVSYGFLSPPQLNKNSSG

IYSEALLTTNIVPMYQSFQVIWRYFHDTLLRKYAEERNGVNVVSGPVFDFDYDGRCDSL

ENLRQKRRVIRNQEILIPTHFFIVLTSCKDTSQTPLHCENLDTLAFILPHRTDNSESCVHGK

HDSSWVEELLMLHRARITDVEHITGLSFYQQRKEPVSDILKLKTHLPTFSQED<u>PKSCDKT</u>

<u>HTCPPCPAPEAAGAPSVFLFPPKPKDTLMISRTPEVTCVVVDVSHEDPEVKFNWYVDGV</u>

<u>EVHNAKTKPREEQYNSTYRVVSVLTVLHQDWLNGKEYKCKVSNKALPAPIEKTISKAK</u>

<u>GQPREPQVYTLPPSREEMTKNQVSLTCLVKGFYPSDIAVEWESNGQPENNYKTTPPVLD</u>

<u>SDGSFFLYSKLTVDKSRWQQGNVFSCSVMHEALHNHYTQKSLSLSPGK</u>

DDDDDDDDDD amino acid sequences of soluble NPP1 containing amino acids from 107 to 925 of SEQ ID NO: 1
SEQ ID NO: 5
SCKGRCFERTFGNCRCDAACVELGNCCLDYQETCIEPEHIWTCNKFRCGEKRLTRSLCA

CSDDCKDKGDCCINYSSVCQGEKSWVEEPCESINEPQCPAGFETPPTLLFSLDGFRAEYL

HTWGGLLPVISKLKKCGTYTKNMRPVYPTKTFPNHYSIVTGLYPESHGIIDNKMYDPKM

NASFSLKSKEKFNPEWYKGEPIWVTAKYQGLKSGTFFWPGSDVEINGIFPDIYKMYNGS

VPFEERILAVLQWLQLPKDERPHFYTLYLEEPDSSGHSYGPVSSEVIKALQRVDGMVGML

MDGLKELNLHRCLNLILISDHGMEQGSCKKYIYLNKYLGDVKNIKVIYGPAARLRPSDV

PDKYYSFNYEGIARNLSCREPNQHFKPYLKHFLPKRLHFAKSDRIEPLTFYLDPQWQLAL

NPSERKYCGSGFHGSDNVFSNMQALFVGYGPGFKHGIEADTFENIEVYNLMCDLLNLTP

APNNGTHGSLNHLLKNPVYTPKHPKEVHPLVQCPFTRNPRDNLGCSCNPSILPIEDFQTQ

FNLTVAEEKIIKHETLPYGRPRVLQKENTICLLSQHQFMSGYSQDILMPLWTSYTVDRND

SFSTEDFSNCLYQDFRIPLSPVHKCSFYKNNTKVSYGFLSPPQLNKNSSGIYSEALLTTNIV

PMYQSFQVIWRYFHDTLLRKYAEERNGVNVVSGPVFDFDYDGRCDSLENLRQKRRVIR

NQEILIPTHFFIVLTSCKDTSQTPLHCENLDTLAFILPHRTDNSESCVHGKHDSSWVEELL

MLHRARITDVEHITGLSFYQQRKEPVSDILKLKTHLPTFSQED amino acid sequence of soluble NPP1 containing amino acids from 187 to 925 of SEQ ID NO: 1
SEQ ID NO: 6
EKSWVEEPCESINEPQCPAGFETPPTLLFSLDGFRAEYLHTWGGLLPVISKLKKCGTYTK

NMRPVYPTKTFPNHYSIVTGLYPESHGIIDNKMYDPKMNASFSLKSKEKFNPEWYKGEPI

WVTAKYQGLKSGTFFWPGSDVEINGIFPDIYKMYNGSVPFEERILAVLQWLQLPKDERP

HFYTLYLEEPDSSGHSYGPVSSEVIKALQRVDGMVGMLMDGLKELNLHRCLNLILISDH

GMEQGSCKKYIYLNKYLGDVKNIKVIYGPAARLRPSDVPDKYYSFNYEGIARNLSCREP

NQHFKPYLKHFLPKRLHFAKSDRIEPLTFYLDPQWQLALNPSERKYCGSGFHGSDNVFS

NMQALFVGYGPGFKHGIEADTFENIEVYNLMCDLLNLTPAPNNGTHGSLNHLLKNPVY

TPKHPKEVHPLVQCPFTRNPRDNLGCSCNPSILPIEDFQTQFNLTVAEEKIIKHETLPYGRP

RVLQKENTICLLSQHQFMSGYSQDILMPLWTSYTVDRNDSFSTEDFSNCLYQDFRIPLSP

VHKCSFYKNNTKVSYGFLSPPQLNKNSSGIYSEALLTTNIVPMYQSFQVIWRYFHDTLLR

KYAEERNGVNVVSGPVFDFDYDGRCDSLENLRQKRRVIRNQEILIPTHFFIVLTSCKDTS

QTPLHCENLDTLAFILPHRTDNSESCVHGKHDSSWVEELLMLHRARITDVEHITGLSFYQ

QRKEPVSDILKLKTHLPTFSQED amino acid sequence of Fc region of human IgG1 including hinge region

SEQ ID NO: 7

EPKSCDKTHTCPPCPAPELLGGPSVFLFPPKPKDTLMISRTPEVTCVVVDVSHEDPEVKF

NWYVDGVEVHNAKTKPREEQYNSTYRVVSVLTVLHQDWLNGKEYKCKVSNKALPAPI

EKTISKAKGQPREPQVYTLPPSREEMTKNQVSLTCLVKGFYPSDIAVEWESNGQPENNY

KTTPPVLDSDGSFFLYSKLTVDKSRWQQGNVFSCSVMHEALHNHYTQKSLSLSPGK amino acid sequence of Fc of human IgG1 including partial hinge region

SEQ ID NO: 8

DKTHTCPPCPAPELLGGPSVFLFPPKPKDTLMISRTPEVTCVVVDVSHEDPEVKFNWYV

DGVEVHNAKTKPREEQYNSTYRVVSVLTVLHQDWLNGKEYKCKVSNKALPAPIEKTIS

KAKGQPREPQVYTLPPSREEMTKNQVSLTCLVKGFYPSDIAVEWESNGQPENNYKTTPP

VLDSDGSFFLYSKLTVDKSRWQQGNVFSCSVMHEALHNHYTQKSLSLSPGK amino acid sequence of NPP1-Fc fusion protein [(107-925)-Fc]

SEQ ID NO: 9

SCKGRCFERTFGNCRCDAACVELGNCCLDYQETCIEPEHIWTCNKFRCGEKRLTRSLCA

CSDDCKDKGDCCINYSSVCQGEKSWVEEPCESINEPQCPAGFETPPTLLFSLDGFRAEYL

HTWGGLLPVISKLKKCGTYTKNMRPVYPTKTFPNHYSIVTGLYPESHGIIDNKMYDPKM

NASFSLKSKEKFNPEWYKGEPIWVTAKYQGLKSGTFFWPGSDVEINGIFPDIYKMYNGS

VPFEERILAVLQWLQLPKDERPHFYTLYLEEPDSSGHSYGPVSSEVIKALQRVDGMVGML

MDGLKELNLHRCLNLILISDHGMEQGSCKKYIYLNKYLGDVKNIKVIYGPAARLRPSDV

PDKYYSFNYEGIARNLSCREPNQHFKPYLKHFLPKRLHFAKSDRIEPLTFYLDPQWQLAL

NPSERKYCGSGFHGSDNVFSNMQALFVGYGPGFKHGIEADTFENIEVYNLMCDLLNLTP

APNNGTHGSLNHLLKNPVYTPKHPKEVHPLVQCPFTRNPRDNLGCSCNPSILPIEDFQTQ

FNLTVAEEKIIKHETLPYGRPRVLQKENTICLLSQHQFMSGYSQDILMPLWTSYTVDRND

SFSTEDFSNCLYQDFRIPLSPVHKCSFYKNNTKVSYGFLSPPQLNKNSSGIYSEALLTTNIV

PMYQSFQVIWRYFHDTLLRKYAEERNGVNVVSGPVFDFDYDGRCDSLENLRQKRRVIR

NQEILIPTHFFIVLTSCKDTSQTPLHCENLDTLAFILPHRTDNSESCVHGKHDSSWVEELL

MLHRARITDVEHITGLSFYQQRKEPVSDILKLKTHLPTFSQEDEPKSCDKTHTCPPCPAPE

LLGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSDGSFFLYSKLT

VDKSRWQQGNVFSCSVMHEALHNHYTQKSLSLSPGK amino acid sequence of NPP1-Fc fusion protein [(107-925)-partial hinge Fc]

SEQ ID NO: 10

SCKGRCFERTFGNCRCDAACVELGNCCLDYQETCIEPEHIWTCNKFRCGEKRLTRSLCA

CSDDCKDKGDCCINYSSVCQGEKSWVEEPCESINEPQCPAGFETPPTLLFSLDGFRAEYL

HTWGGLLPVISKLKKCGTYTKNMRPVYPTKTFPNHYSIVTGLYPESHGIIDNKMYDPKM

NASFSLKSKEKFNPEWYKGEPIWVTAKYQGLKSGTFFWPGSDVEINGIFPDIYKMYNGS

VPFEERILAVLQWLQLPKDERPHFYTLYLEEPDSSGHSYGPVSSEVIKALQRVDGMVGML

MDGLKELNLHRCLNLILISDHGMEQGSCKKYIYLNKYLGDVKNIKVIYGPAARLRPSDV

PDKYYSFNYEGIARNLSCREPNQHFKPYLKHFLPKRLHFAKSDRIEPLTFYLDPQWQLAL

NPSERKYCGSGFHGSDNVFSNMQALFVGYGPGFKHGIEADTFENIEVYNLMCDLLNLTP

APNNGTHGSLNHLLKNPVYTPKHPKEVHPLVQCPFTRNPRDNLGCSCNPSILPIEDFQTQ

-continued

FNLTVAEEKIIKHETLPYGRPRVLQKENTICLLSQHQFMSGYSQDILMPLWTSYTVDRND

SFSTEDFSNCLYQDFRIPLSPVHKCSFYKNNTKVSYGFLSPPQLNKNSSGIYSEALLTTNIV

PMYQSFQVIWRYFHDTLLRKYAEERNGVNVVSGPVFDFDYDGRCDSLENLRQKRRVIR

NQEILIPTHFFIVLTSCKDTSQTPLHCENLDTLAFILPHRTDNSESCVHGKHDSSWVEELL

MLHRARITDVEHITGLSFYQQRKEPVSDILKLKTHLPTFSQEDDKTHTCPPCPAPELLGGP

SVFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQVYTLPPSR

EEMTKNQVSLTCLVKGFYPSDIAVEWESNGQPENNYKTTPPVLDSDGSFFLYSKLTVDK

SRWQQGNVFSCSVMHEALHNHYTQKSLSLSPGK amino acid sequence of NPP1-Fc fusion protein [(187-925)-Fc]
SEQ ID NO: 11
EKSWVEEPCESINEPQCPAGFETPPTLLFSLDGFRAEYLHTWGGLLPVISKLKKCGTYTK

NMRPVYPTKTFPNHYSIVTGLYPESHGIIDNKMYDPKMNASFSLKSKEKFNPEWYKGEPI

WVTAKYQGLKSGTFFWPGSDVEINGIFPDIYKMYNGSVPFEERILAVLQWLQLPKDERP

HFYTLYLEEPDSSGHSYGPVSSEVIKALQRVDGMVGMLMDGLKELNLHRCLNLILISDH

GMEQGSCKKYIYLNKYLGDVKNIKVIYGPAARLRPSDVPDKYYSFNYEGIARNLSCREP

NQHFKPYLKHFLPKRLHFAKSDRIEPLTFYLDPQWQALNPSERKYCGSGFHGSDNVFS

NMQALFVGYGPGFKHGIEADTFENIEVYNLMCDLLNLTPAPNNGTHGSLNHLLKNPVY

TPKHPKEVHPLVQCPFTRNPRDNLGCSCNPSILPIEDFQTQFNLTVAEEKIIKHETLPYGRP

RVLQKENTICLLSQHQFMSGYSQDILMPLWTSYTVDRNDSFSTEDFSNCLYQDFRIPLSP

VHKCSFYKNNTKVSYGFLSPPQLNKNSSGIYSEALLTTNIVPMYQSFQVIWRYFHDTLLR

KYAEERNGVNVVSGPVFDFDYDGRCDSLENLRQKRRVIRNQEILIPTHFFIVLTSCKDTS

QTPLHCENLDTLAFILPHRTDNSESCVHGKHDSSWVEELLMLHRARITDVEHITGLSFYQ

QRKEPVSDILKLKTHLPTFSQEDEPKSCDKTHTCPPCPAPELLGGPSVFLFPPKPKDTLMI

SRTPEVTCVVVDVSHEDPEVKFNWYVDGVEVHNAKTKPREEQYNSTYRVVSVLTVLH

QDWLNGKEYKCKVSNKALPAPIEKTISKAKGQPREPQVYTLPPSREEMTKNQVSLTCLV

KGFYPSDIAVEWESNGQPENNYKTTPPVLDSDGSFFLYSKLTVDKSRWQQGNVFSCSV

MHEALHNHYTQKSLSLSPGK amino acid sequence of NPP1-Fc fusion protein [(187-925)-partial hinge Fc]
SEQ ID NO: 12
EKSWVEEPCESINEPQCPAGFETPPTLLFSLDGFRAEYLHTWGGLLPVISKLKKCGTYTK

NMRPVYPTKTFPNHYSIVTGLYPESHGIIDNKMYDPKMNASFSLKSKEKFNPEWYKGEPI

WVTAKYQGLKSGTFFWPGSDVEINGIFPDIYKMYNGSVPFEERILAVLQWLQLPKDERP

HFYTLYLEEPDSSGHSYGPVSSEVIKALQRVDGMVGMLMDGLKELNLHRCLNLILISDH

GMEQGSCKKYIYLNKYLGDVKNIKVIYGPAARLRPSDVPDKYYSFNYEGIARNLSCREP

NQHFKPYLKHFLPKRLHFAKSDRIEPLTFYLDPQWQALNPSERKYCGSGFHGSDNVFS

NMQALFVGYGPGFKHGIEADTFENIEVYNLMCDLLNLTPAPNNGTHGSLNHLLKNPVY

TPKHPKEVHPLVQCPFTRNPRDNLGCSCNPSILPIEDFQTQFNLTVAEEKIIKHETLPYGRP

RVLQKENTICLLSQHQFMSGYSQDILMPLWTSYTVDRNDSFSTEDFSNCLYQDFRIPLSP

VHKCSFYKNNTKVSYGFLSPPQLNKNSSGIYSEALLTTNIVPMYQSFQVIWRYFHDTLLR

KYAEERNGVNVVSGPVFDFDYDGRCDSLENLRQKRRVIRNQEILIPTHFFIVLTSCKDTS

QTPLHCENLDTLAFILPHRTDNSESCVHGKHDSSWVEELLMLHRARITDVEHITGLSFYQ

-continued

QRKEPVSDILKLKTHLPTFSQEDDKTHTCPPCPAPELLGGPSVFLFPPKPKDTLMISRTPE

VTCVVVDVSHEDPEVKFNWYVDGVEVHNAKTKPREEQYNSTYRVVSVLTVLHQDWL

NGKEYKCKVSNKALPAPIEKTISKAKGQPREPQVYTLPPSREEMTKNQVSLTCLVKGFY

PSDIAVEWESNGQPENNYKTTPPVLDSDGSFFLYSKLTVDKSRWQQGNVFSCSVMHEA

LHNHYTQKSLSLSPGK human IgG1 hinge region                                    SEQ ID NO: 13

EPKSCDKTHTCPPCP portion of human IgG1 hinge region                         SEQ ID NO: 14

DKTHTCPPCP portion of human IgG1 hinge region                         SEQ ID NO: 15

PKSCDKTHTCPPCP

Linker                                                     SEQ ID NO: 16

(Gly$_4$Ser)$_3$ amino acid motif that is start of soluble NPP1 which includes
cysteine rich region                                       SEQ ID NO: 17

PSCAKE

SEQ ID NO: 18

D10 targeting moiety synthetic linker                                           19

(Gly$_4$Ser)$_n$,

---

What is claimed is:

1. A method for treating a human subject having hypertension, wherein said subject is not ENPP1 deficient, the method comprising administering to the subject one or more doses of a recombinant human soluble ectonucleotide pyrophosphatase phosphodiesterase (hsNPP1), active fragment or fusion protein thereof, wherein said administration reduces hypertension and said reduction in hypertension is independent of reduction in calcification in said subject.

2. A method for reducing hypertension in a human subject, wherein said subject is not ENPP1 deficient, the method comprising administering to the subject one or more doses of a recombinant human soluble ectonucleotide pyrophosphatase phosphodiesterase (hsNPP1), active fragment or fusion protein thereof, wherein said reduction in hypertension is independent of reduction in calcification in said subject.

3. The method of claim 1 or 2, wherein the hsNPP1 is a fusion protein.

4. The method of claim 3, wherein the fusion protein comprises an Fc region of an immunoglobulin.

5. The method of claim 3, wherein the fusion protein comprises a targeting moiety.

6. The method of claim 5, wherein said targeting moiety comprises at least eight consecutive aspartic acid or glutamic acid residues (SEQ ID NOs: 20 and 21, respectively).

7. The method of claim 3, wherein the fusion protein comprises SEQ ID NO:3, SEQ ID NO:4, SEQ ID NO:9, SEQ ID NO: 10, SEQ ID NO:11 or SEQ ID NO: 12.

8. The method of claim 1 or 2, wherein the one or more doses contains 1.0 mg/kg (+/−20%) to 20.0 mg/kg (+/−20%) NPP1.

9. The method of claim 1 or 2, wherein the one or more doses contains 1.0 mg/kg (+/−20%) to 5.0 mg/kg (+/−20%) NPP1.

10. The method of claim 1 or 2, wherein the one or more doses is 0.2 mg/kg (+/−20%), 0.5 mg/kg (+/−20%), 1 mg/kg (+/−20%), 2.0 mg/kg (+/−20%), 5.0 mg/kg (+/−20%), 6.0 mg/kg (+/−20%), 10 mg/kg (+/−20%), 15 mg/kg (+/−20%), or 20 mg/kg (+/−20%).

11. The method of claim 1 or 2, wherein two or more doses of NPP1 are administered at least 3 days, 1 week, 2 weeks or 1 month apart.

12. The method of claim 1 or 2, wherein the administration is weekly, bi-weekly, or monthly.

13. The method of claim 1 or 2, wherein the administration is intravenous, subcutaneous, or intraperitoneal.

14. The method of claim 1 or 2, wherein an additional therapeutic agent is administered to the subject.

15. The method of claim 1, wherein the treatment comprises a reduction in elevated blood pressure, normalization of blood pressure, a reduction in left ventricular end-diastolic pressure (EDP), a reduction in left ventricular end-systolic pressure (ESP), a reduction in ventricle stiffness, and/or an increase in contractility.

16. The method of claim 15, wherein the reduction in elevated blood pressure is a reduction in blood pressure higher than 140 over 90 millimeters of mercury (mmHg) to 120 over 80 mm (+/−10%) of mercury (mmHg).

17. The method of claim 1 or 2, wherein the one or more doses contains 1.0 mg/kg (+/−10%) to 20.0 mg/kg (+/−10%) NPP1.

18. The method of claim 1 or 2, wherein the one or more doses contains 1.0 mg/kg (+/−5%) to 20.0 mg/kg (+/−5%) NPP1.

19. The method of claim 1 or 2, wherein the one or more doses contains 1.0 mg/kg (+/−5%) to 20.0 mg/kg (+/−1%) NPP1.

20. The method of claim 1 or 2, wherein the one or more doses contains 1.0 mg/kg (+/−10%) to 5.0 mg/kg (+/−10%) NPP1.

21. The method of claim 1 or 2, wherein the one or more doses contains 1.0 mg/kg (+/−5%) to 5.0 mg/kg (+/−5%) NPP1.

22. The method of claim 1 or 2, wherein the one or more doses contains 1.0 mg/kg (+/−1%) to 5.0 mg/kg (+/−1%) NPP1.

23. The method of claim 1 or 2, wherein the one or more doses is 0.2 mg/kg (+/−10%), 0.5 mg/kg (+/−10%), 2.0 mg/kg 6.0 mg/kg (+/−10%), 10 mg/kg (+/−10%), or 15 mg/kg (+/−10%), or 20 mg/kg (+/−10%).

24. The method of claim 1 or 2, wherein the one or more doses is 0.2 mg/kg (+/−5%), 0.5 mg/kg (+/−5%), 2.0 mg/kg (+/−5%), 6.0 mg/kg (+/−5%), 10 mg/kg (+/−5%), or 15 mg/kg (+/−5%).

25. The method of claim 1 or 2, wherein the one or more doses is 0.2 mg/kg (+/−1%), 0.5 mg/kg (+/−1%), 2.0 mg/kg (+/−1%), 6.0 mg/kg (+/−1%), 10 mg/kg (+/−1%), or 15 mg/kg (+/−1%).

* * * * *

UNITED STATES PATENT AND TRADEMARK OFFICE
CERTIFICATE OF CORRECTION

PATENT NO. : 12,134,790 B2
APPLICATION NO. : 16/648388
DATED : November 5, 2024
INVENTOR(S) : Tayeba Khan et al.

Page 1 of 1

It is certified that error appears in the above-identified patent and that said Letters Patent is hereby corrected as shown below:

In the Claims

At Column 88, Claim number 19, Line number 22, please replace "+/-5" with -- +/-1 --

At Column 88, Claim number 23, Line number 35, please insert -- (+/– 10%) -- after "mg/kg" and before "6.0 mg/kg"

At Column 88, Claim number 23, Line number 36, please delete ", or 20mg/kg (+/–10%)"

Signed and Sealed this
Tenth Day of June, 2025

Coke Morgan Stewart
*Acting Director of the United States Patent and Trademark Office*